United States Patent
Rivera-Feliciano et al.

(10) Patent No.: US 12,097,239 B2
(45) Date of Patent: Sep. 24, 2024

(54) METHODS AND COMPOSITIONS FOR TREATING DIABETES, AND METHODS FOR ENRICHING MRNA CODING FOR SECRETED PROTEINS

(71) Applicant: President and Fellows of Harvard College, Cambridge, MA (US)

(72) Inventors: Jose Rivera-Feliciano, Brookline, MA (US); Edwin Rosado-Olivieri, Somerville, MA (US); Douglas A. Melton, Lexington, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 17/278,644

(22) PCT Filed: Sep. 23, 2019

(86) PCT No.: PCT/US2019/052517
§ 371 (c)(1),
(2) Date: Mar. 22, 2021

(87) PCT Pub. No.: WO2020/061591
PCT Pub. Date: Mar. 26, 2020

(65) Prior Publication Data
US 2021/0308215 A1 Oct. 7, 2021

Related U.S. Application Data

(60) Provisional application No. 62/734,981, filed on Sep. 21, 2018.

(51) Int. Cl.
| | | |
|---|---|---|
| A61K 38/00 | (2006.01) | |
| A61K 38/17 | (2006.01) | |
| A61P 3/10 | (2006.01) | |

(52) U.S. Cl.
CPC ............ *A61K 38/1709* (2013.01); *A61P 3/10* (2018.01)

(58) Field of Classification Search
CPC .............................. A61K 38/1709; A61P 3/10
See application file for complete search history.

(56) References Cited

U.S. PATENT DOCUMENTS

| | | | | |
|---|---|---|---|---|
| 9,827,332 B2 * | 11/2017 | Bancel | ................. | C07K 14/485 |
| 11,446,398 B2 * | 9/2022 | Barrett | ................. | C12N 5/0647 |
| 2014/0329704 A1 | 11/2014 | Melton et al. | | |

FOREIGN PATENT DOCUMENTS

| | | | |
|---|---|---|---|
| WO | 2005/100987 A1 | 10/2005 | |
| WO | WO 2005/100987 | * 10/2005 | |
| WO | WO-2016/170348 A2 | 10/2016 | |
| WO | WO-2017/060319 A1 | 4/2017 | |
| WO | WO-2017/191274 A2 | 11/2017 | |

OTHER PUBLICATIONS

Gerhard et al., Genome Research, 14: 2121-2127 (2004).*
Delgado, et al., "Open Reading Frames Associated with Cancer in the Dark Matter of the Human Genome," *Cancer Genomics & Proteomics*:201-214, (2014).
Lim, "Exploring the Genetic Landscape of Complex Diseases Using the Recessive Model," Retrieved on Jan. 15, 2020. Retrieved from the Internet https://dash.harvard.edu/bitstream/handle/1/12274464/Lim_gsas.harvard_0084L_11490.pdf?sequence+4#/page=47. pp. 1-53.
Taneera, et al., "A Systems Genetics Approach Identifies Genes and Pathways for Type 2 Diabetes in Human Islets," *Cell Metabolism*, 76:122-134, Jul. 3, 2012; and Supplemental Information pp. 1-79.
International Search Report for PCT/US2019/052517, dated Feb. 28, 2020.
Anonymous: "C1orf127—Uncharacterized Protein C1orf127—Homo Sapiens (Human)," (2015). Retrieved from the Internet: https://web.archive.org/web/20150322162931/ttps://www.uniprot.org/uniprot/Q8N9H9.
Genecards Human Gene Database: "C1orf127 Gene—GeneCards/CA127 Protein/CA127 Antibody," (2017). Retrieved from the Internet: https://web.archive.org/web/2017102003/https://www.genecards.org/cgi-bin/carddisp.pl?gene=C1orf127.
Yang, et al., "Utilizing Glycine N-Methyltransferasegene Knockout Mice as a Model for Identification of Missing Proteins in Hepatocellular Carcinoma," *Oncotarget*, 9(1):442-452, (2018).
*Homo sapiens* chromosome 1 open reading frame 127 (C1orf127), mRNA, [o nline]. Jun. 24, 2018 uploaded. NCBI Nucleotide, ACCESSION No. NM_001170754 (GI:282721089) [Retrieved on Jul. 24, 2023]. Retrieved from the internet: <URL: https://www.ncbi.nlm.nih.gov/nuccore/282721089?sat=46&satkey=16696 3998>.

* cited by examiner

*Primary Examiner* — Gyan Chandra
(74) *Attorney, Agent, or Firm* — Morse, Barnes-Brown & Pendleton, P.C.; Lisa M. Warren, Esq.; Erin E. Bryan, Esq.

(57) ABSTRACT

A previously uncharacterized gene and gene product are disclosed herein that increase blood glucose clearance independent of insulin. Also described is a methodology for enriching for mRNAs transcribing excreted and membrane bound proteins as well as a non-human animal expressing a labeled SEC61b protein.

10 Claims, 40 Drawing Sheets
Specification includes a Sequence Listing.

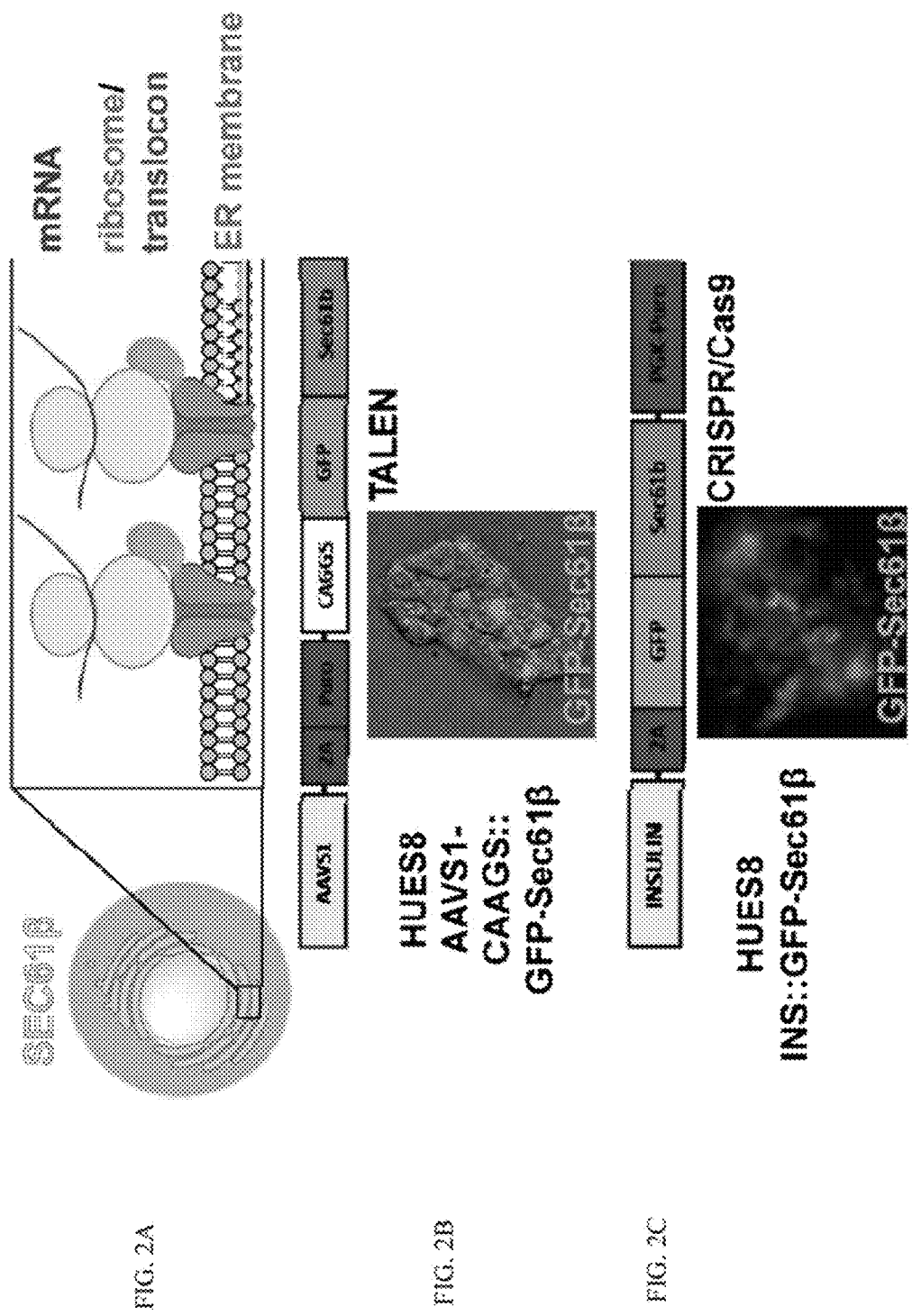

| ACCESSION | GENE | DESCRIPTION | COVERAGE | PEPTIDES |
|---|---|---|---|---|
| B4DR61 | SEC61A1 | Sec61 subunit alpha isoform 1 | 24.69 | 29 |
| Q59GX9 | RPL5 | Ribosomal protein L5 | 29.37 | 21 |
| P13667 | PDIA4 | Protein disulfide-isomerase A4 | 22.79 | 17 |
| Q9H9S3 | SEC61A2 | Sec61 subunit alpha isoform 2 | 10.92 | 4 |
| P46783 | RPS10 | 40S ribosomal protein S10 | 23.03 | 7 |
| P61254 | RPL26 | 60S ribosomal protein L26 | 20.69 | 5 |
| A8MUS3 | RPL23A | 60S ribosomal protein L23a | 16.49 | 4 |

FIG 3D

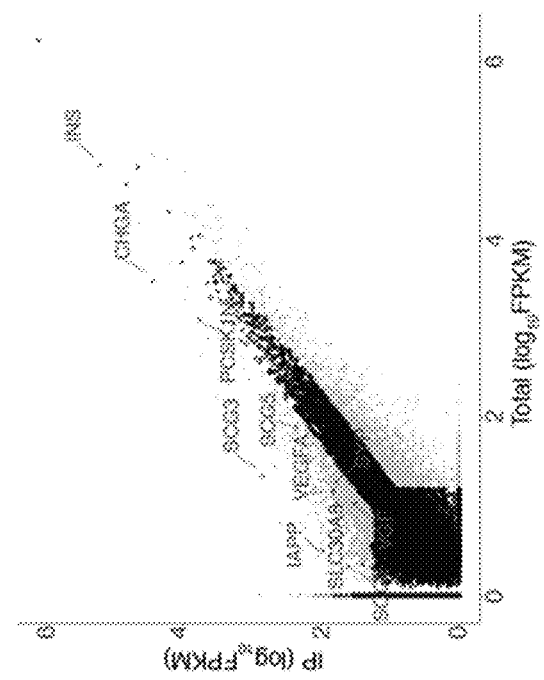
FIG. 5C
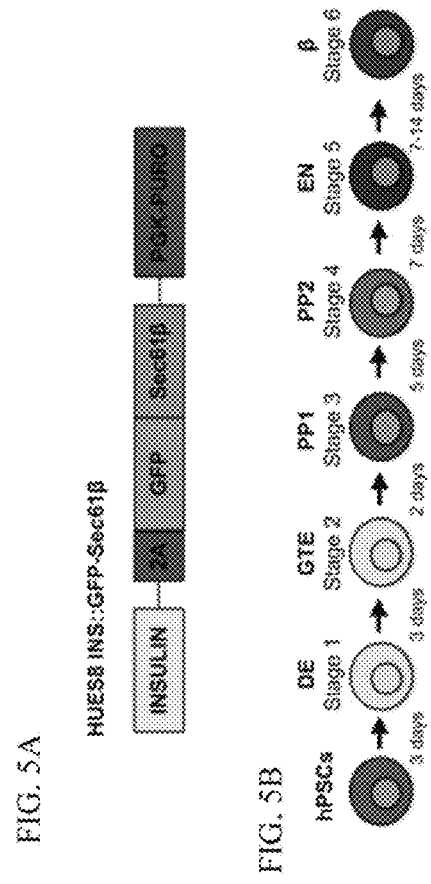
FIG. 5A
FIG. 5B

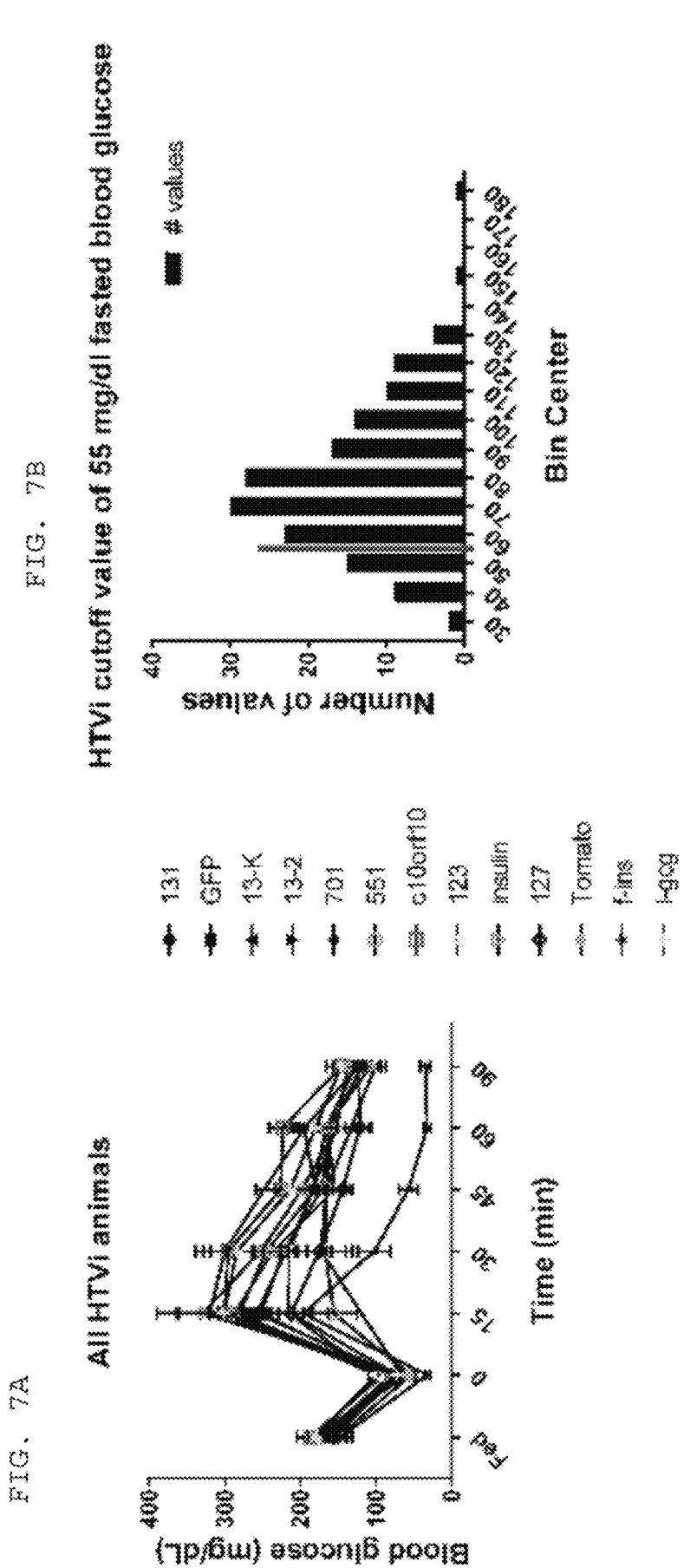

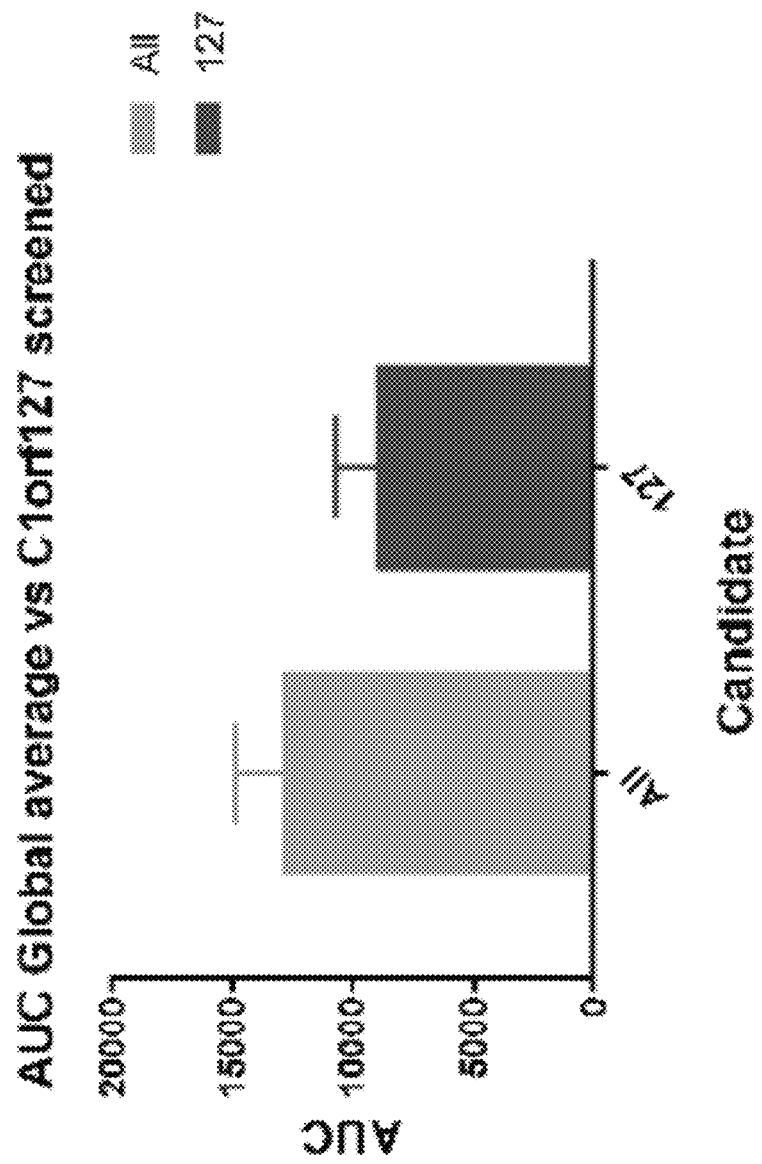

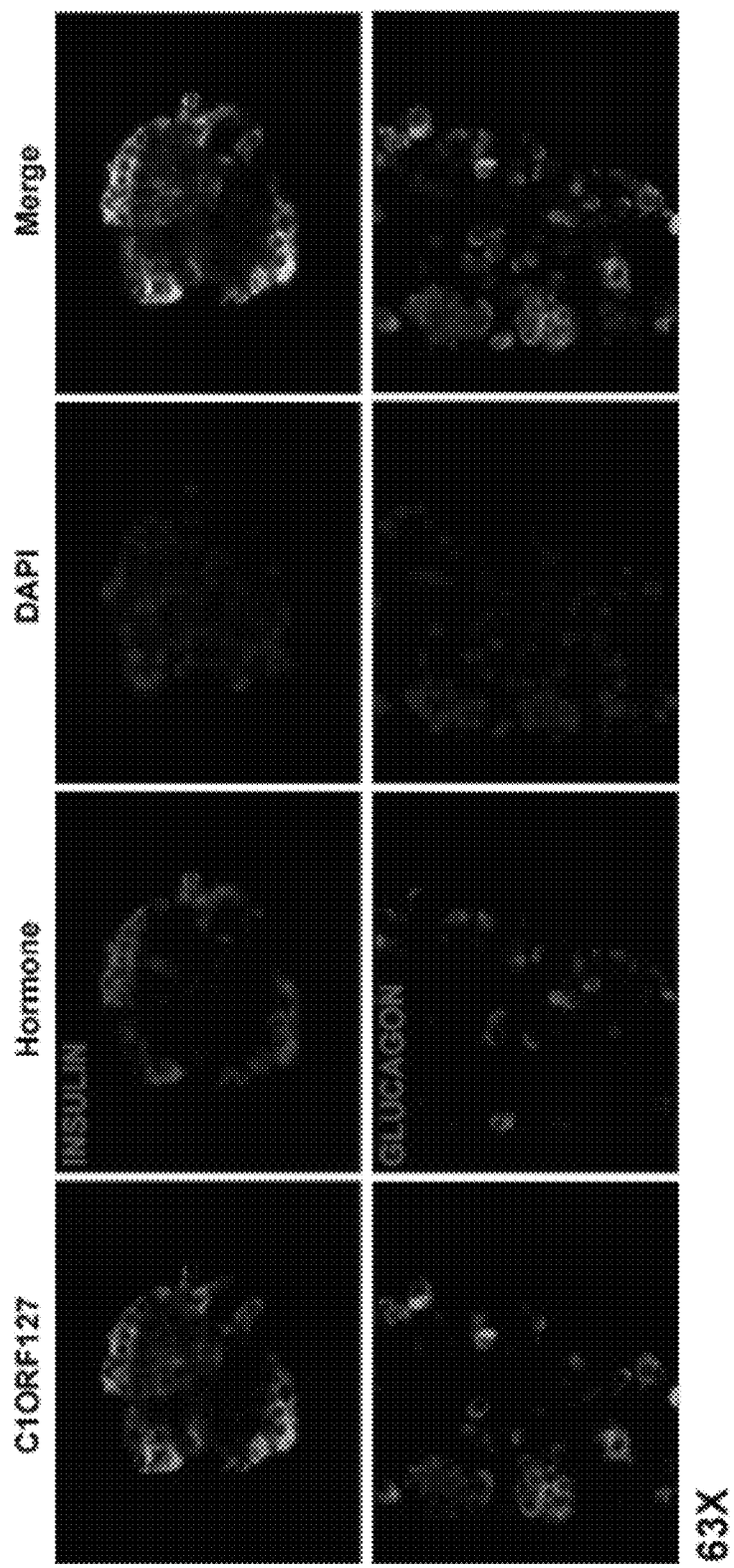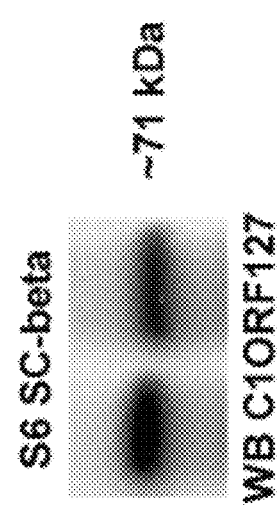
FIG. 12

METHODS AND COMPOSITIONS FOR TREATING DIABETES, AND METHODS FOR ENRICHING MRNA CODING FOR SECRETED PROTEINS

CROSS-REFERENCE TO RELATED APPLICATIONS

This application is a national stage filing under 35 U.S.C. 371 of International Application No. PCT/US2019/052517, filed Sep. 23, 2019, which claims the benefit of U.S. Provisional Application No. 62/734,981, filed on Sep. 21, 2018. The entire teachings of the above applications are incorporated herein by reference. International Application No. PCT/US2019/052517 was published under PCT Article 21(2) in English.

GOVERNMENT SUPPORT

This invention was made with government support under Grant No. 2014182349 awarded by the National Science Foundation. The government has certain rights in the invention.

BACKGROUND OF THE INVENTION

According to the World Health Organization more than 422 million people in the world have diabetes. The Endocrine Society is estimating that by 2021 the cost burden of diabetes in the United States alone will be $512 billion. Current strategies to treat diabetics include insulin injection, augmenting endogenous insulin secretion, increasing glucose absorption, or increasing glucose excretion.

Diabetes is a disease derived from multiple causative factors and characterized by elevated levels of plasma glucose (hyperglycemia) in the fasting state. There are two main forms of diabetes mellitus: (1) insulin-dependent or Type 1 diabetes (a.k.a., Juvenile Diabetes) and (2) non-insulin-dependent or Type II diabetes (a.k.a., NIDDM).

Type 1 diabetes is caused by insulin deficiency resulting from loss of pancreatic beta cells, typically as a result of autoimmune destruction of the islets of Langerhans. Thus, in patients who suffer from type 1 diabetes the amount of insulin produced by the pancreatic islet cells is too low, resulting in elevated blood glucose levels (hyperglycemia). Patients with type 1 diabetes generally require lifelong insulin treatment, but even with frequent daily injections of insulin it is difficult to adequately control blood glucose levels.

In type 2 diabetic patients, liver and muscle cells lose their normal ability to respond to normal blood insulin levels (insulin resistance), resulting in high blood glucose levels. Additionally, Type II diabetic patients exhibit impairment of beta cell function and an increase in beta cell apoptosis, causing a reduction in total beta cell mass over time. Eventually, the administration of exogenous insulin becomes necessary in type 2 diabetics.

Conventional methods for treating diabetes have included administration of fluids and insulin in the case of Type 1 diabetes and administration of various hypoglycemic agents in Type II diabetes. Unfortunately many of the known hypoglycemic agents exhibit undesirable side effects and toxicities. Thus, for both type 1 and type 2 diabetes, there is a need for new treatment modalities.

SUMMARY OF THE INVENTION

A previously uncharacterized gene and gene product are disclosed herein that increase blood glucose clearance. Surprisingly and unexpectedly, this gene product (C1ORF127 gene product) lowers blood glucose independent of insulin and does not cause hypoglycemia.

The C1ORF127 gene is predicted to code for a protein of 684 amino acids with a molecular weight of 73 kDa. It is a highly conserved protein that only exists in vertebrates. The predicted sequence lacks canonical signals for secretion or membrane insertion. C1ORF127 has an N-terminal domain of 215 amino acids that is highly conserved in vertebrates. Within this domain are two predicted glycosylation sites, one predicted phosphorylation site, five conserved Cysteine residues, and a putative endopeptidase cleavage site (prohormone convertase 2 like, PC2). Thus, like other glucose regulating hormones, C1ORF127 gene product may be processed into a heretofore unidentified smaller protein fragment with glucose-lowering activity. The cysteines may participate in protein folding or multimerization.

Identification of the gene product and its activity provide a new method for treating diabetes and other diseases involving blood glucose clearance, as well as a new avenue into understanding the causes and effects of diseases involving blood glucose clearance. Also described herein is a methodology for enriching for mRNAs transcribing excreted and membrane bound proteins.

Some aspects of the disclosure are directed to a method of treating or preventing a disorder associated with elevated blood glucose levels in a subject, comprising administering to said subject an effective amount of an agent that increases the level or activity of a C1ORF127 gene product (herein also sometimes referred to as ERseq08). In some embodiments, the agent increases the level or activity of an endogenous C1ORF127 gene product when administered to the subject. In some embodiments, the agent increases the expression of an endogenous C1ORF127 gene product when administered to the subject. In some embodiments, the agent increases the secretion of an endogenous C1ORF127 gene product when administered to the subject. In some embodiments, the agent is a C1ORF127 gene product agonist.

In some embodiments, the agent comprises a small molecule, a protein, or a nucleic acid. In some embodiments, the agent comprises a C1ORF127 gene product having at least one different post-translational modification than a native C1ORF127 gene product. In some embodiments, the agent comprises a C1ORF127 gene product having at least one substituted, deleted, or added amino acid than a native C1ORF127 gene product. In some embodiments, the agent comprises a C1ORF127 gene product having a different activity or activity level than a native C1ORF127 gene product. In some embodiments, the agent comprises a functional portion of a C1ORF127 gene product. In some embodiments, the agent comprises a C1ORF127 gene product comprising a furin cleavage site. In some embodiments, the agent comprises a C1ORF127 gene product without a PC2 cleavage site. In some embodiments, the agent comprises a C1ORF127 gene product with a furin cleavage site and without a PC2 cleavage site.

In some embodiments, the agent further comprises a pharmaceutically acceptable carrier. In some embodiments, the method further comprises administration of an additional anti-diabetic therapeutic.

In some embodiments, the agent is a cell expressing C1ORF127 gene product. In some embodiments, the cell is an islet cell or a beta-cell. In some embodiments, the cell is autologous to the subject requiring treatment. In some embodiments, the cell is stem cell-derived. In some embodiments, the stem cell-derived cell is a stem cell-derived beta cell. In some embodiments, the cell is encased in a microcapsule or semi-permeable membrane.

In some embodiments, the agent improves blood glucose clearance when administered to the subject. In some embodiments, the blood glucose clearance property of the agent is independent of insulin activity. In some embodiments, the agent does not cause hypoglycemia when administered to the subject. In some embodiments, the agent has glucose sensitizer activity when administered to the subject. In some embodiments, the agent increases the rate of glucose turnover when administered to the subject. In some embodiments, the agent increases glycolysis when administered to the subject. In some embodiments, the agent increases the rate of glycogen synthesis when administered to the subject. In some embodiments, the agent has glucagon-like activity when administered to the subject.

In some embodiments, the subject has diabetes. In some embodiments, the subject is human or murine.

In some embodiments, the agent comprises a C1ORF127 protein of SEQ ID NO: 2 or a functional portion or functional variant thereof. In some embodiments, the agent comprises a nucleic acid molecule coding for a C1ORF127 gene product, a functional portion or functional variant thereof, and wherein the nucleic acid comprises the sequence of SEQ ID NO: 1 or a portion thereof. In some embodiments, the agent comprises a nucleic acid coding for a C1ORF127 gene product, a functional portion or functional variant thereof, and the nucleic acid comprises a sequence having at least 90% homology to SEQ ID NO: 1 or a portion thereof.

In some embodiments, administration of the agent corrects a genetic defect in the subject causing aberrant expression or activity of the C1ORF127 gene product.

Some aspects of the disclosure are directed to an agent that increases the level or activity of a C1ORF127 gene product when administered to the subject.

In some embodiments, the agent increases the level or activity of an endogenous C1ORF127 gene product when administered to the subject. In some embodiments, the agent increases the expression of an endogenous C1ORF127 gene product when administered to the subject. In some embodiments, the agent increases the secretion of an endogenous C1ORF127 gene product when administered to the subject.

In some embodiments, the agent comprises a small molecule, a protein, or a nucleic acid. In some embodiments, the agent comprises a C1ORF127 gene product having at least one different post-translational modification than a native C1ORF127 gene product. In some embodiments, the agent comprises a C1ORF127 gene product having at least one substituted, deleted, or added amino acid than a native C1ORF127 gene product. In some embodiments, the agent comprises a C1ORF127 gene product having a different activity or activity level than a native C1ORF127 gene product. In some embodiments, the agent comprises a functional portion of a C1ORF127 gene product.

In some embodiments, the agent further comprises a pharmaceutically acceptable carrier. In some embodiments, the method further comprises administration of an additional anti-diabetic therapeutic.

In some embodiments, the agent improves blood glucose clearance when administered to the subject. In some embodiments, the blood glucose clearance property of the agent is independent of insulin activity. In some embodiments, the agent does not cause hypoglycemia when administered to the subject. In some embodiments, the agent has glucose sensitizer activity when administered to the subject. In some embodiments, the agent increases the rate of glucose turnover when administered to the subject. In some embodiments, the agent increases glycolysis when administered to the subject. In some embodiments, the agent increases the rate of glycogen synthesis when administered to the subject. In some embodiments, the agent has glucagon-like activity when administered to the subject.

In some embodiments, the subject has diabetes. In some embodiments, the subject is human or murine.

In some embodiments, the agent comprises a C1ORF127 protein of SEQ ID NO: 2 or a functional portion or functional variant thereof. In some embodiments, the agent comprises a nucleic acid coding for a C1ORF127 gene product, a functional portion or functional variant thereof, and wherein the nucleic acid comprises the sequence of SEQ ID NO: 1 or a portion thereof. In some embodiments, the agent comprises a nucleic acid coding for a C1ORF127 gene product, a functional portion or functional variant thereof, and the nucleic acid comprises a sequence having at least 90% homology to SEQ ID NO: 1 or a portion thereof.

Some aspects of the disclosure are related to a method of diagnosing a C1ORF127-related disorder or an increased risk for developing a C1ORF127-related disorder in a test individual, comprising determining a C1ORF127 gene product level in a sample obtained from said test individual, wherein a C1ORF127 gene product level that is increased or decreased in said test individual compared to a C1ORF127 gene product level in a normal individual is indicative of a C1ORF127-related disorder. In some embodiments, the C1ORF127 gene product level is detected in a blood sample. In some embodiments, the C1ORF127 gene product is detected with an antibody. In some embodiments, the C1ORF127-related disorder is diabetes.

Some aspects of the disclosure are related to a method of diagnosing a C1ORF127-related disorder or an increased risk for developing a C1ORF127-related disorder in a test individual, comprising screening the test individual for a mutation in C1ORF127. In some embodiments, the C1ORF127-related disorder is diabetes.

Some aspects of the disclosure are related to a method of screening for a C1ORF127 gene product receptor agonist, comprising contacting a cell responsive to a C1ORF127 gene product with a test agent and measuring cell response, wherein if the cell responds then the test agent is identified as a C1ORF127 gene product receptor agonist. In some embodiments, the cell response is glucose uptake. In some embodiments, the cell is further contacted with an insulin receptor antagonist.

Some aspects of the disclosure are related to a method of enriching for mRNAs coding for secreted and membrane bound proteins, comprising: a) providing a cell comprising a Endoplasmic Reticulum (ER) translocon comprising a label, b) performing sub-cellular fractionalization of the cell and isolating an ER fraction containing the label, and c) isolating and sequencing mRNA contained in the isolated ER fraction containing the label. In some embodiments, the ER translocon component SEC61b comprises the label. In some embodiments, the label is a fluorescent label. In some embodiments, b) comprises contacting the cell with a protein synthesis inhibitor, solubilizing the cell plasma membrane, and immunoprecipitating the ER. In some embodiments, the ER is immunoprecipitated with an antibody specific for the label. In some embodiments, the protein synthesis inhibitor is cyclohexamide. In some embodiments, the cell plasma membrane (or cell plasma membrane followed by the ER membrane) is solubilized with step-wise concentrations of detergent. In some embodiments, the detergent is digitonin, DDM, or both. In some embodiments, the mRNA is sequenced by next generation sequencing.

In some embodiments, the cell is a beta-cell. In some embodiments, the cell is an induced stem cell or is differentiated from an induced stem cell. In some embodiments, the cell is a diseased cell or exhibits an aberrant state. In some embodiments, the cell is undergoing a stress response when contacted with the protein synthesis inhibitor. In some embodiments, the cell is responding to a stimulus when contacted with the protein synthesis inhibitor.

In some embodiments, the method further comprises performing the method of enriching for mRNAs coding for secreted and membrane bound proteins as described herein on a control cell, and comparing the mRNAs isolated from the cell to the mRNAs isolated from the control cell.

Some aspects of the invention are directed to a non-human animal capable of expressing a labeled SEC61b protein. In some embodiments, expression of the labeled protein is inducible. In some embodiments, the labeled protein has Cre-dependent expression. In some embodiments, the non-human animal has inducible expression of the labeled SEC16b protein in beta-cells. The label is not limited and may be any suitable label in the art. In some embodiments, the label is a fluorescent protein. In some embodiments, the label is Green Fluorescent Protein (GFP). In some embodiments, the non-human animal is a mouse or rat. In some embodiments, the non-human animal is a model of diabetes (e.g., NOD model of type 1 diabetes, model of type 1 diabetes).

BRIEF DESCRIPTION OF THE DRAWINGS

These and other characteristics of the present invention will be more fully understood by reference to the following detailed description in conjunction with the attached drawings. The patent or application file contains at least one drawing executed in color. Copies of this patent or patent application publication with color drawings will be provided by the Office upon request and payment of the necessary fee.

FIG. 1A: GTT at Day 3 after HTV injections in ICR outbred mice demonstrated that C1ORF127 can clear glucose from the circulation faster than controls. FIG. 1B: GTT at Day 3 after HTV injections in C57Bl6 animals dosed with the insulin receptor antagonist S961. Note the elevated blood glucose levels in B. relative to A. and the potent reduction in blood glucose levels in C1ORF127 treated animals starting at 60 minutes relative to controls. In experiments not shown, the reduction in glucose mediated by C1ORF127 starts as early as 15 minutes post glucose injection.

FIGS. 2A-2C shows generation of hPSCs cell lines expression GFP-SEC61β. FIG. 2A: A GFP tag was engineered into the cytosolic domain of SEC61β to facilitate the isolation of ribosome/translocon complexes at the ER membrane. FIG. 2B: Strategy for the TALEN-mediated knock-in of CAAGS::GFP-SEC61β transgene into the AAVS1 locus and perinuclear expression of GFP in hPSCs. FIG. 2C: Strategy for the CRISPR-mediated knock-in of GFP-SEC61β into the last exon of the insulin gene. Bottom panels of FIGS. 2B-2C show GFP expression in SC-β cells differentiated using this cell line.

FIGS. 3A-3D show ER-Seq enriches for components of the translocon complexes and associated ribosomes. FIG. 3A: Sequential biochemical fractionation approach for the step-wise isolation of cytosolic, ER and nuclear components. ER fraction was subjected to immunopurification of ribosome/translocon complexes and associated RNA. FIG. 3B: Western blot of Sec61β, GFP and ribosomal protein L13a in multiple subcellular fractions after biochemical fractionation. FIG. 3C: RNA gel and identification of 18S and 28S ribosomal RNA subunits. FIG. 3D: Proteomics-based identification of proteins that are associated with translocon complexes. The Uniprot Accession ID, peptide coverage of full-length protein and number of peptides identified are listed. T: total; Cy: cytosolic fraction; Nu: nuclear fraction; Un: unbound ER fraction after immunoprecipitation; IP: immunopurified ER fraction.

FIG. 4A: Scatterplot of log-normalized microarray signal intensities of genes defected in IP and unfractionated cell extracts. Each dot represents a gene. Differentially expressed genes are colored light grey. Candidate secreted or translocon-associated factors are labeled and colored red. FIG. 4B: Pie chart of predicted subcellular localization of IP-enriched genes. FIG. 4C: Top gene ontology terms of IP-enriched genes.

FIGS. 5A-5F show ER-seq enriches for mRNAs of secreted factors expressed in SC-β cells. FIG. 5A: Diagram of the transgenic hPSC cell line that expresses GFP-SEC610 in insulin-expressing β cells. FIG. 5B: Directed differentiation protocol of for the generation of SC-β cells using the INS::GFP-SEC61β cell line. FIG. 5C: Scatterplot of log 10-normalized expression of genes detected in IP and total unfractionated RNA. Candidate genes are labeled and colored red. Differentially expressed genes are colored light grey. FIG. 5D: Pie chart of predicted localization of IP-enriched genes (fold change >2 relative to total). FIG. 5E: Log 2 enrichment of genes predicted to be part of the secretome or cytosolic/nuclear (CytoNuc) relative to total unfractionated RNA. Enrichment of IP expression relative to total RNA is shown. FIG. 5F: Top gene ontology terms of IP-enriched genes.

FIG. 6A: Diagram of the directed differentiation protocol of SC-β cells and the relevant stages at which each of the hPSC cell lines were used. FIG. 6B: Heatmap of differentially expressed genes identified by ER-seq across multiple stages of differentiation. FIG. 6C-FIG. 6D: Gene ontology analysis of genes that are preferentially expressed in SC-β cells and top terms for biological processes (FIG. 6C) and cellular components (FIG. 6D). FIG. 6E-FIG. 6F: Heatmap of endocrine-specific (FIG. 6E) and unannotated (FIG. 6F) genes across all stages of differentiation displaying a R cell-specific expression pattern. FIG. 6G: Heatmap of genes with unknown function in SC-beta cells.

FIGS. 7A-7E shows identification of C1ORF127 as a glucose lowering activity. FIG. 7A: Results from Hydrodynamic tail vein injection screen. FIG. 7B: Animals with fasting blood glucose levels below 55 mg/dl were removed from further analysis. FIG. 7C: C1ORF127 (red line) clears glucose from circulation faster than other activities tested. FIG. 7D: for clarity purposes all other treatments were averaged and displayed in grey. Insulin HTV injected animals (purple) serve as a positive control and also show a robust glucose lowering activity. FIG. 7E: quantification of the glucose lowering effect shows that the difference is statistically significant.

FIG. 8A: Protein alignments reveal the high degree of conservation of this protein during evolution. FIG. 8B: alignment of human C1ORF127 with its mouse orthologue, Gm572. Red bar, peptide region used to generate a C1ORF127 antibody used for immunofluorescence analysis and western blot (commercially available antibody). C1ORF127 is a highly conserved 73 kDa protein lacking a signal peptide. C1ORF127 is expressed in SC-beta cells and developing mouse pancreas from the inception of endocrine lineage. C1ORF127 is also expressed in adult human and mouse beta-cells.

FIG. 9A: in cadaveric human islets, C1ORF127 is expressed predominantly in beta-cells. FIG. 9B: in SC-beta C1ORF127 is predominantly expressed by SC-beta cells at later stages of differentiation.

FIG. 10A: t-SNE projection at late stages of the SC-beta differentiation protocol. C1ORF127 is co-expressed by SC-beta cells, SC-enterochromaffin cells, and in endocrine progenitors. FIG. 10B: the mouse orthologue of C1ORF127, Gm572 is expressed by endocrine progenitors.

FIG. 12 shows Immunofluorescence and Western Blot analysis of C1ORF127. Top immunofluorescence, using a commercially available antibody to C1ORF127 it is shown that C1ORF127 is expressed by beta-cells in islets from human cadavers. Note high co-localization with INSULIN staining and absence from GLUCAGON expressing cells. Bottom, Western blot, Extracts from SC-beta cells express C1ORF127 at its predicted molecular weight.

FIG. 13A: Gene expression analysis from the GTEx consortium shows expression in Cerebellum and Muscle. FIG. 13B confirms both sites of expression by immunofluorescence staining. C1ORF127 colocalizes with Laminin in muscle and with Tuj1 in cerebellum.

FIG. 18A: GTT at Day 3 after HTV injections in ICR outbred mice demonstrated that ER-seq08 can clear glucose from the circulation faster than controls. All time points are significantly different. FIG. 18B: Area under the curve measurements from A demonstrating a significant improvement in glucose clearance in ER-seq08-injected mice relative to controls. FIG. 18C: Blood glucose levels in ER-seq08-injected animals before and after a 16 hour fast, notice there is no significant change in blood glucose levels relative to controls.

FIG. 19A: C1ORF127 primary structure with Purple bar: evolutionary conserved domain of unknown function; PC2 site: putative endopeptidase cleavage site-commonly present in peptide hormones (i.e. INSULIN, GLUCAGON, and AMYLIN); Red bar: A custom rabbit polyclonal antibody generated to the region in red recognizes the full length protein (73 kDa) and a protein of ~57 kDa. This 57 kDa species correlates with the presumptive PC2 cleavage site. FIG. 19B: is a western blot: total protein extracts were made from human cadaveric islets from non-diabetic (ND) and type 2 diabetic (T2D) patients. Antibody specificity was determined by competition with the peptide used to immunize the rabbits. Although it is expected that the glucose lowering activity of C1ORF127 resides in the conserved domain of unknown function (purple box), the activity may reside on the remainder (57 kDa region). C1ORF127 is also expressed by delta and gamma cells in the Islets of Langerhans and in muscle and cerebellum. Although, it is speculated that the glucose lowering activity of C1ORF127 is unique to beta-cells, other C1ORF127 expression depots may also have glucose modulating activities.

FIG. 25A: construct used for mES targeting. mES positive clones were infected with Cre-virus to show excision of the loxp cassette and marking of the ER. FIG. 25B: tail tip fibroblasts from Green-ER mice crossed to a ubiquitous reporter. Note stereotypical ER-staining. FIG. 25C: beta-cell Green-ER mice demonstrate tissue-specific recombination in Insulin producing cells and appropriate sub-cellular localization.

FIG. 27A: Blood glucose levels in C1ORF127 tail vein injected Streptozotocin (STZ) ablated animals. These animals were fasted overnight and administered with glucose, then their blood glucose level was monitored. This larger cohort showed the same glucose clearance phenotype as previous. FIG. 27B: Eight weeks later, the same cohort was again tail vein injected with either C1orf127 (ERseq08) or tdTomato. Three days later, these mice were fasted overnight, and treated with S961 at 2-hours before glucose injection and at the time of glucose injection. Their blood glucose levels were monitored. The Streptozotocin ablation, while enough to cause severe diabetes in the mice, leaves a small population of insulin-producing beta-cells. The S961 insulin-antagonist treatment of the ablated animals shows that residual insulin is not responsible for the glucose clearance phenotype. NOTE: Both experiments utilized a glucometer with a maximal reading of 750 mg/dl, instead of the previous maximum of 600 mg/dl.

DETAILED DESCRIPTION OF THE INVENTION

Figure 1A:
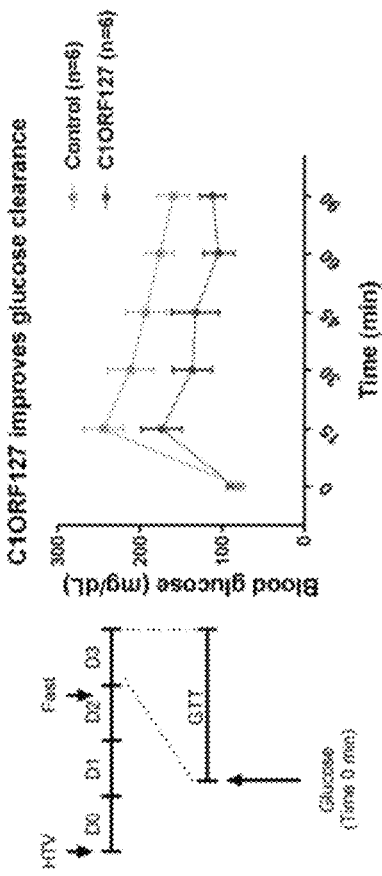
FIGS. 1A-1B show that C1ORF127 improves glucose clearance independent of insulin action. Glucose Tolerance Tests (GTT—2.0 mg/dl glucose bolus) were performed on the third day after hydrodynamic tail vein injections (HTV).

Embodiments of the inventions described herein arise from a novel method of enriching for mRNAs associated with the endoplasmic reticulum and thus likely coding for secreted proteins. When performing this method on beta-cells, a previously uncharacterized mRNA was isolated. When a nucleic acid sequence coding for the gene product of this mRNA (the C1ORF127 gene product) was expressed in mice, the mice had improved blood glucose clearance independent of insulin. The C1ORF127 gene product therefore provides a new methodology for treatment of diseases and conditions involving blood glucose clearance, such as diabetes.

Methods of Treating or Preventing Disorders Associated with Elevated Blood Glucose Levels Some aspects of the disclosure are related to a method of treating or preventing a disorder associated with elevated blood glucose levels in a subject, comprising administering to said subject an effective amount of an agent that modulates the level or activity of a C1ORF127 gene product.

As used herein a disorder associated with elevated blood glucose levels is any disorder wherein the subject has elevated blood glucose levels. In some embodiments, the disorder is diabetes (e.g., Type I diabetes or Type II diabetes), metabolic syndrome, glucose intolerance, or obesity.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments, the subject is a mammal, e.g., a primate, e.g., a human. The terms, "patient", "individual" and "subject" are used interchangeably herein. Preferably, the subject is a mammal. The mammal can be a human, non-human primate, mouse, rat, dog, cat, horse, or cow, but are not limited to these examples. Mammals other than humans can be advantageously used, for example, as subjects that represent animal models of, for example, diabetes. In addition, the methods described herein can be used to treat domesticated animals and/or pets. A subject can be male or female.

A subject can be one who has been previously diagnosed with or identified as suffering from or having a condition in need of treatment (e.g., diabetes) or one or more complications related to such a condition, and optionally, but need not have already undergone treatment for a condition or the one or more complications related to the condition. Alternatively, a subject can also be one who has not been previously diagnosed as having a condition in need of treatment or one or more complications related to such a condition. Rather, a subject can include one who exhibits one or more risk factors for a condition or one or more complications related to a condition. A "subject in need" of treatment for a particular condition can be a subject having that condition, diagnosed as having that condition, or at increased risk of developing that condition relative to a given reference population.

The term "agent" as used herein means any compound or substance such as, but not limited to, a small molecule, nucleic acid, polypeptide, peptide, drug, ion, etc. An "agent" can be any chemical, entity or moiety, including without limitation synthetic and naturally-occurring proteinaceous and non-proteinaceous entities. In some embodiments, an agent is nucleic acid, nucleic acid analogues, proteins, antibodies, peptides, aptamers, oligomer of nucleic acids, amino acids, or carbohydrates including without limitation proteins, oligonucleotides, ribozymes, DNAzymes, glycoproteins, siRNAs, lipoproteins, aptamers, and modifications and combinations thereof etc. In some embodiments, the agent is selected from the group consisting of a nucleic acid, a small molecule, a polypeptide, and a peptide. In certain embodiments, agents are small molecule having a chemical moiety. For example, chemical moieties included unsubstituted or substituted alkyl, aromatic, or heterocyclyl moieties including macrolides, leptomycins and related natural products or analogues thereof. Compounds can be known to have a desired activity and/or property, or can be selected from a library of diverse compounds.

"Small molecule" is defined as a molecule with a molecular weight that is less than 10 kD, typically less than 2 kD, and preferably less than 1 kD. Small molecules include, but are not limited to, inorganic molecules, organic molecules, organic molecules containing an inorganic component, molecules comprising a radioactive atom, synthetic molecules, peptide mimetics, and antibody mimetics. As a therapeutic, a small molecule may be more permeable to cells, less susceptible to degradation, and less apt to elicit an immune response than large molecules.

As used herein, the term "polypeptide" or "protein" is used to designate a series of amino acid residues connected to the other by peptide bonds between the alpha-amino and carboxy groups of adjacent residues. The term "polypeptide" refers to a polymer of protein amino acids, including modified amino acids (e.g., phosphorylated, glycated, glycosylated, etc.) and amino acid analogs, regardless of its size or function. The term "peptide" is often used in reference to small polypeptides, but usage of this term in the art overlaps with "protein" or "polypeptide." Exemplary polypeptides include gene products, naturally occurring proteins, homologs, orthologs, paralogs, fragments and other equivalents, as well as both naturally and non-naturally occurring variants, fragments, and analogs of the foregoing.

The term "nucleic acid" refers to polynucleotides such as deoxyribonucleic acid (DNA) and ribonucleic acid (RNA). The terms "nucleic acid" and "polynucleotide" are used interchangeably herein and should be understood to include double-stranded polynucleotides, single-stranded (such as sense or antisense) polynucleotides, and partially double-stranded polynucleotides. A nucleic acid often comprises standard nucleotides typically found in naturally occurring DNA or RNA (which can include modifications such as methylated nucleobases), joined by phosphodiester bonds. In some embodiments a nucleic acid may comprise one or more non-standard nucleotides, which may be naturally occurring or non-naturally occurring (i.e., artificial; not found in nature) in various embodiments and/or may contain a modified sugar or modified backbone linkage. Nucleic acid modifications (e.g., base, sugar, and/or backbone modifications), non-standard nucleotides or nucleosides, etc., such as those known in the art as being useful in the context of RNA interference (RNAi), aptamer, CRISPR technology, polypeptide production, reprogramming, or antisense-based molecules for research or therapeutic purposes may be incorporated in various embodiments. Such modifications may, for example, increase stability (e.g., by reducing sensitivity to cleavage by nucleases), decrease clearance in vivo, increase cell uptake, or confer other properties that improve the translation, potency, efficacy, specificity, or otherwise render the nucleic acid more suitable for an intended use. Various non-limiting examples of nucleic acid modifications are described in, e.g., Deleavey G F, et al., Chemical modification of siRNA. Curr. Protoc. Nucleic Acid Chem. 2009; 39:16.3.1-16.3.22; Crooke, ST (ed.) Antisense drug technology: principles, strategies, and applications, Boca Raton: CRC Press, 2008; Kurreck, J. (ed.) Therapeutic oligonucleotides, RSC biomolecular sciences. Cambridge: Royal Society of Chemistry, 2008; U.S. Pat. Nos. 4,469,863; 5,536,821; 5,541,306; 5,637,683; 5,637,684; 5,700,922; 5,717,083; 5,719,262; 5,739,308; 5,773,601; 5,886,165; 5,929, 226; 5,977,296; 6,140,482; 6,455,308 and/or in PCT application publications WO 00/56746 and WO 01/14398. Different modifications may be used in the two strands of a double-stranded nucleic acid. A nucleic acid may be modified uniformly or on only a portion thereof and/or may contain multiple different modifications. Where the length of a nucleic acid or nucleic acid region is given in terms of a number of nucleotides (nt) it should be understood that the number refers to the number of nucleotides in a single-stranded nucleic acid or in each strand of a double-stranded nucleic acid unless otherwise indicated. An "oligonucleotide" is a relatively short nucleic acid, typically between about 5 and about 100 nt long.

The term "modulates C1ORF127 gene product level or activity" refers to upregulation (activation or increasing activity) or downregulation (inhibition) of a gene product (e.g., C1ORF127 protein) level, activity or function. In one embodiment, the modulation occurs by directly increasing or inhibiting the activity of a gene product, i.e., via direct physical interaction with the gene product. In one embodiment, the activity of the gene product is modulated indirectly, for example, in signaling, by activating or inhibiting an upstream effector of the gene product activity. In some embodiments, the agent increases the level or activity of endogenous C1ORF127 gene product when administered to a subject. In some embodiments, the agent increases the expression of endogenous C1ORF127 gene product when administered to a subject. In some embodiments, the agent increases the secretion of endogenous C1ORF127 gene product when administered to a subject. In some embodiments, the agent is an agonist of endogenous C1ORF127 gene product.

The terms "decrease," "reduce," "reduced," "reduction," "decrease," and "inhibit" are all used herein generally to mean a decrease by a statistically significant amount relative to a reference. However, for avoidance of doubt, "reduce," "reduction" or "decrease" or "inhibit" typically means a decrease by at least 10% as compared to a reference level and can include, for example, a decrease by at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, up to and including, for example, the complete absence of the given entity or parameter as compared to the reference level, or any decrease between 10-99% as compared to the absence of a given treatment.

The terms "increased," "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90%, or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or more as compared to a reference level.

As used herein, "treat," "treatment," or "treating" when used in reference to a disease, disorder or medical condition, refer to therapeutic treatments for a condition, wherein the object is to reverse, alleviate, ameliorate, inhibit, slow down or stop the progression or severity of a symptom or condition. The term "treating" includes reducing or alleviating at least one adverse effect or symptom of a condition. Treatment is generally "effective" if one or more symptoms or clinical markers are reduced. Alternatively, treatment is "effective" if the progression of a condition is reduced or halted. That is, "treatment" includes not just the improvement of symptoms or markers, but also a cessation or at least slowing of progress or worsening of symptoms that would be expected in the absence of treatment.

The methods described herein may lead to a reduction in the severity or the alleviation of one or more symptoms of the disorder. Symptoms of diabetes include, for example, elevated fasting blood glucose levels, blood pressure at or above 140/90 mm/Hg; abnormal blood fat levels, such as high-density lipoproteins (HDL) less than or equal to 35 mg/dL, or triglycerides greater than or equal to 250 mg/dL (mg/dL=milligrams per deciliter of blood). Other symptoms of diabetes include for example frequent urination, excessive thirst, extreme hunger, unusual weight loss, increased fatigue, irritability, or blurry vision.

In some embodiments, the methods disclosed herein delays the onset of diabetes. Delaying the onset of diabetes in a subject refers to delay of onset of at least one symptom of diabetes, e.g., hyperglycemia, hyperinsulinemia, diabetic retinopathy, diabetic nephropathy, blindness, memory loss, renal failure, cardiovascular disease (including coronary artery disease, peripheral artery disease, cerebrovascular disease, atherosclerosis, and hypertension), neuropathy, autonomic dysfunction, hyperglycemic hyperosmolar coma, or combinations thereof, for at least 1 week, at least 2 weeks, at least 1 month, at least 2 months, at least 6 months, at least 1 year, at least 2 years, at least 5 years, at least 10 years, at least 20 years, at least 30 years, at least 40 years or more, and can include the entire lifespan of the subject.

As used herein, "prevent" when used in reference to a disease, disorder or medical condition, refers to reducing or eliminating the likelihood of development of the disease, disorder or medical condition.

As used herein, the term "administering," refers to the placement of the agent as disclosed herein into a subject by a method or route which results in delivery to a site of action. The agent can be administered by any appropriate route which results in an effective treatment in the subject. Thus administration via the intravenous route is specifically contemplated. However, with appropriate formulation, other routes are contemplated, including, for example, intranasally, intraarterially; intra-coronary arterially; orally, by inhalation, intraperitoneally, intramuscularly, subcutaneously, intracavity, or by other means known by those skilled in the art. The agents are administered in a manner compatible with the dosage formulation, and in a therapeutically effective amount. The quantity to be administered and timing depends on the subject to be treated, capacity of the subject's system to utilize the active ingredient, and degree of therapeutic effect desired.

A "therapeutically effective amount" is an amount of an agent that is sufficient to produce a statistically significant, measurable change in, for example, blood glucose clearance. Such effective amounts can be gauged in clinical trials as well as animal studies. A treatment is considered "effective treatment," as the term is used herein, if any one or all of the signs or symptoms are improved or ameliorated, e.g., by at least 10% following treatment with an agent as described herein. Efficacy can also be measured by a failure of an individual to worsen as assessed by hospitalization or need for medical interventions (i.e., progression of the disease is halted). Methods of measuring these indicators are known to those of skill.

In some embodiments, the agent comprises a small molecule, a protein, or a nucleic acid. In particular aspects, desirable agents (e.g., compounds) increase levels or activity (e.g., by increasing expression and/or secretion) of C1ORF127 gene product (e.g., C1ORF127 protein). Suitable compounds/agents include, but are not limited to, chemical compounds and mixtures of chemical compounds, e.g., small organic or inorganic molecules; saccharides; oligosaccharides; polysaccharides; biological macromolecules, e.g., peptides, proteins, and peptide analogs and derivatives; peptidomimetics; nucleic acids; nucleic acid analogs and derivatives; extracts made from biological materials such as bacteria, plants, fungi, or animal cells or tissues; naturally occurring or synthetic compositions; peptides; aptamers; and antibodies, or fragments thereof.

A compound/agent can be a nucleic acid RNA or DNA, and can be either single or double stranded. Example nucleic acid compounds include, but are not limited to, a nucleic acid encoding a protein activator or inhibitor (e.g. transcriptional activators or inhibitors), oligonucleotides, nucleic acid analogues (e.g. peptide-nucleic acid (PNA), pseudo-complementary PNA (pc-PNA), locked nucleic acid (LNA) etc.), antisense molecules, ribozymes, small inhibitory or activating nucleic acid sequences (e.g., RNAi, shRNAi, siRNA, micro RNAi (mRNAi), antisense oligonucleotides etc.)

A protein and/or peptide agent can be any protein that modulates gene expression or protein activity. Non-limiting examples include mutated proteins; therapeutic proteins and truncated proteins, e.g. wherein the protein is normally absent or expressed at lower levels in the target cell. Proteins can also be selected from genetically engineered proteins, peptides, synthetic peptides, recombinant proteins, chimeric proteins, antibodies, midibodies, minibodies, triabodies, humanized proteins, humanized antibodies, chimeric antibodies, modified proteins and fragments thereof. A compound or agent that increases expression of a gene or increases the level or activity of a protein encoded by a gene is also known as an activator or activating compound. A compound or agent that decreases expression of a gene or decreases the level or activity of a protein encoded by a gene is also known as an inhibitor or inhibiting compound. In some embodiments, a protein or polypeptide agent may be a functional variant or functional fragment of native C1ORF127 gene product.

In some embodiments, C1ORF127 has a nucleotide sequence of SEQ ID NO: 1:

ATGGGGTTGGAGCGGAGTGATCGCTACATAATGAAGTGTCCGATGCTAAG

GTCAAGGCTGGGTCAGGAAAGCGTCCACTGTGGGCCCATGTTCATCCAGG

TCTCCCGGCCCCTGCCCCTGTGGAGGGACAATAGACAGACTCCATGGCTG

CTGTCCCTTCGAGGGGAGCTGGTGGCTTCTCTTGAAGACGCCAGCCTGAT

GGGACTGTATGTGGACATGAATGCCACCACTGTCACCGTCCAAAGCCCGA

GACAAGGCCTTCTTCAGAGGTGGGAGGTGCTGAACACCTCTGCTGAGCTC

CTGCCACTATGGCTGGTGAGCGGTCACCATGCCTATTCTTTAGAAGCTGC

TTGCCCACCGGTGTCATTCCAGCCAGAGTCGGAGGTCTTAGTTCACATCC

CCAAGCAGAGACTGGGTCTAGTCAAAAGAGGTTCCTACATTGAGGAAACC

CTGAGCCTCAGATTCCTCCGAGTCCACCAGTCCAACATCTTTATGGTGAC

TGAGAACAAGGACTTTGTGGTGGTCAGCATTCCGGCGGCCGGGGTGCTCC

AGGTCCAGCGATGCCAAGAAGTCGGAGGAACCCCGGGAACACAAGCTTTC

TATAGGGTAGACCTGAGCCTGGAATTTGCCGAGATGGCTGCCCCGGTCCT

CTGGACAGTGGAGAGCTTCTTCCAGTGTGTGGGTTCAGGAACAGAGTCGC

-continued

CTGCCTCAACTGCTGCACTGAGGACCACTCCCTCCCCACCATCCCCAGGA

CCAGAGACCCCTCCAGCGGGAGTGCCACCTGCTGCTTCCTCCCAGGTGTG

GGCTGCAGGACCAGCTGCCCAGGAATGGCTTTCTCGGGACCTCCTGCACC

GGCCTTCCGACGCACTGGCCAAAAAGGGGCTTGGACCATTCCTGCAAACA

GCCAAACCGGCGAGAAGAGGCCAGACATCTGCCTCCATTCTCCCCAGAGT

GGTGCAAGCTCAGCGAGGTCCCCAGCCTCCCCCAGGGGAAGCAGGGATCC

CTGGACACCCCACACCTCCAGCCACGCTCCCCTCGGAGCCTGTAGAGGGT

GTCCAGGCTAGTCCCTGGCGGCCACGTCCAGTCTTGCCAACGCACCCGGC

TCTGACCCTGCCCGTGTCCTCAGATGCCTCCTCTCCTTCACCGCCAGCCC

CGAGGCCTGAACGACCTGAATCACTTCTGGTCTCAGGACCATCTGTCACC

CTGACTGAAGGTCTAGGAACTGTGAGGCCTGAACAGGACCCCGCCAAGTC

TCCAGGAAGTCCCCTCCTGCTGAGAGGCTTGTCAAGCGGGGATGTGGCTG

CACCTGAGCCCATCATGGGGGAGCCCGGCCAAGCCAGTGAGGAGTTCCAG

CCATTGGCGAGGCCCTGGCGGGCCACACTGGCTGCAGAGGAGCTGGTTTC

TCACCGTTCTCCCGGAGAGCCCCAGGAAACGTGCTCTGGAACGGAGGTGG

AGAGGCCACGCCAGACAGGGCCTGGTCTCCCCAGGGAGGGGGCCAGGGGG

CACATGGACCTTTCATCCTCAGAACCAAGCCAGGACATAGAGGGGCCGGG

ACTCTCCATCCTGCCAGCGAGGGATGCCACATTCTCCACCCCAAGTGTGA

GGCAGCCAGACCCCAGTGCCTGGCTGAGTTCAGGACCTGAACTCACCGGG

ATGCCCAGGGTGAGGCTGGCAGCGCCCCTGGCAGTTCTTCCTATGGAACC

TCTGCCACCAGAACCTGTTCGCCCAGCAGCTCTTCTGACACCCGAAGCCT

CATCTGTGGGAGGGCCAGACCAGGCCCGATACCTGGAGTCAGCCCCTGGC

TGGCCTGTGGGCCAGGAGGAGTGGGGGGTTGCACACACGTCCAGCCCTCC

ATCCACGCAAACCCTGAGCCTGTGGGCTCCCACAGGAGTGTTGCTACCCA

GCCTGGTGGAGCTTGAATACCCCTTCCAGGCTGGCCGGGGGGCCTCACTC

CAGCAGGAGCTGACAGAGCCCACCTTGGCCCTCAGTGCTGAAAGCCACAG

GCCTCCTGAGCTTCAAGACAGTGTGGAGGGGCTTTCTGAGAGGCCCTCAC

GC.

In some embodiments, a C1ORF127 has a nucleotide sequence having at least about 80%, 85%, 90%, 91%, 92%, 93%, 94%, 95%, 96%, 97%, 98%, or 99% identity to SEQ ID NO: 1.

In some embodiments, a C1ORF127 gene product has an amino acid sequence of SEQ ID NO: 2:

MGLERSDRYIMKCPMLRSRLGQESVHCGPMFIQVSRPLPLWRDNRQTPWL

LSLRGELVASLEDASLMGLYVDMNATTVTVQSPRQGLLQRWEVLNTSAEL

LPLWLVSGHHAYSLEAACPPVSFQPESEVLVHIPKQRLGLVKRGSYIEET

LSLRFLRVHQSNIFMVTENKDFVVVSIPAAGVLQVQRCQEVGGTPGTQAF

YRVDLSLEFAEMAAPVLWTVESFFQCVGSGTESPASTAALRTTPSPPSPG

PETPPAGVPPAASSQVWAAGPAAQEWLSRDLLHRPSDALAKKGLGPFLQT

AKPARRGQTSASILPRVVQAQRGPQPPPGEAGIPGHPTPPATLPSEPVEG

VQASPWRPRPVLPTHPALTLPVSSDASSPSPPAPRPERPESLLVSGPSVT

-continued

LTEGLGTVRPEQDPAKSPGSPLLLRGLSSGDVAAPEPIMGEPGQASEEFQ

PLARPWRATLAAEELVSHRSPGEPQETCSGTEVERPRQTGPGLPREGARG

HMDLSSSEPSQDIEGPGLSILPARDATFSTPSVRQPDPSAWLSSGPELTG

MPRVRLAAPLAVLPMEPLPPEPVRPAALLTPEASSVGGPDQARYLESAPG

WPVGQEEWGVAHTSSPPSTQTLSLWAPTGVLLPSLVELEYPFQAGRGASL

QQELTEPTLALSAESHRPPELQDSVEGLSERPSR.

In some embodiments, C1ORF127 gene product has an amino acid sequence having at least about 80%, 85%, 90%, 91%, 92%, 93%, 94%, 95%, 96%, 97%, 98%, or 99% identity to SEQ ID NO: 2.

In some embodiments, the agent comprises a conserved domain of the C1ORF127 gene product or a functional portion or functional variant thereof. In some embodiments, the conserved domain has the amino acid sequence of SEQ ID NO: 3:

KCPMLRSRLGQESVHCGPMFIQVSRPLPLWRDNRQTPWLLSLRGELVASL

EDASLMGLYVDMNATTVTVQSPRQGLLQRWEVLNTSAELLPLWLVSGHHA

YSLEAACPPVSFQPESEVLVHIPKQRLGLVKRGSYIEETLSLRFLRVHQS

NIFMVTENKDEVVVSIPAAGVLQVQRCQEVGGTPGTQAFYRVDLSLEFAE

MAAPVLWTVESFFQC

In some embodiments, the agent comprises a portion of the conserved domain corresponding to SEQ ID NO: 4 or a functional portion or functional variant thereof:

GSYIEETLSLRFLRVHQSNIFMVTENKDFVVVSIPAAGVLQVQRCQEVGG

TPGTQAFYRVDLSLEFAEMAAPVLWTVESFFQC

In some embodiments, the agent comprises an approximately 57 kDa protein produced by cleavage of the C1ORF127 gene product or a functional portion or functional variant thereof. In some embodiments, the approximately 57 kDa protein has the amino acid sequence of SEQ ID NO: 5:

GSYIEETLSLRFLRVHQSNIFMVTENKDFVVVSIPAAGVLQVQRCQEVGG

TPGTQAFYRVDLSLEFAEMAAPVLWTVESFFQCVGSGTESPASTAALRTT

PSPPSPGPETPPAGVPPAASSQVWAAGPAAQEWLSRDLLHRPSDALAKKG

LGPFLQTAKPARRGQTSASILPRVVQAQRGPQPPPGEAGIPGHPTPPATL

PSEPVEGVQASPWRPRPVLPTHPALTLPVSSDASSPSPPAPRPERPESLL

VSGPSVTLTEGLGTVRPEQDPAKSPGSPLLLRGLSSGDVAAPEPIMGEPG

QASEEFQPLARPWRATLAAEELVSHRSPGEPQETCSGTEVERPRQTGPGL

PREGARGHMDLSSSEPSQDIEGPGLSILPARDATFSTPSVRQPDPSAWLS

SGPELTGMPRVRLAAPLAVLPMEPLPPEPVRPAALLTPEASSVGGPDQAR

YLESAPGWPVGQEEWGVAHTSSPPSTQTLSLWAPTGVLLPSLVELEYPFQ

AGRGASLQQELTEPTLALSAESHRPPELQDSVEGLSERPSR

In some embodiments, the C1ORF127 gene product has an amino acid sequence that has at least about 80%, 85%, 90%, 91%, 92%, 93%, 94%, 95%, 96%, 97%, 98%, or 99% identity to SEQ ID NO: 3, SEQ ID NO: 4, or SEQ ID NO: 5.

In some embodiments, the agent comprises a nucleotide sequence that codes for the C1ORF127 gene product of SEQ ID NO: 3, SEQ ID NO: 4, or SEQ ID NO: 5, or a functional portion or functional variant thereof. In some embodiments, the agent comprises a nucleotide sequence that codes for a polypeptide that has at least about 80%, 85%, 90%, 91%, 92%, 93%, 94%, 95%, 96%, 97%, 98%, or 99% identity to SEQ ID NO: 3, SEQ ID NO: 4, or SEQ ID NO: 5, or a functional portion or functional variant thereof.

In some embodiments, the agent comprises C1ORF127 or a C1ORF127 gene product (e.g., C1ORF127 protein). In some embodiments, the agent is a C1ORF127 gene product having at least one different post-translational modification than a native C1ORF127 gene product. Such modifications include, but are not limited to, acetylation, carboxylation, glycosylation (e.g., O-linked oligosaccharides, N-linked oligosaccharides, etc.), phosphorylation, lipidation, and acylation. In some embodiments, the agent comprises a C1ORF127 gene product having at least one substituted, deleted, or added amino acid than a native C1ORF127 gene product. In some embodiments, the C1ORF127 gene product has 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more substituted, deleted, or added amino acids than a native C1ORF127 gene product. In some embodiments, the C1ORF127 gene product has 1, 2, 3, 4, or 5 less cysteines than native C1ORF127 gene product. In some embodiments, the 1, 2, 3, 4, or 5 less cysteines correspond to the conserved cysteines as shown in SEQ ID NO: 3.

In some embodiments, the C1ORF127 gene product is differently phosphorylated than naturally occurring C1ORF127 gene product. In some embodiments, the C1ORF127 gene product has one less phosphorylation than naturally occurring C1ORF127 gene product. In some embodiments, the C1ORF127 gene product has one more phosphorylation than naturally occurring C1ORF127 gene product. In some embodiments, the different phosphorylation is present in the portion of C1ORF127 gene product corresponding to SEQ ID NO: 4 or SEQ ID NO: 5 (e.g., in a putative phosphorylation site in SEQ ID NO: 4 or SEQ ID NO: 5).

In some embodiments, the C1ORF127 gene product is differently glycosylated than naturally occurring C1ORF127 gene product. In some embodiments, the C1ORF127 gene product has one less glycosylation than naturally occurring C1ORF127 gene product. In some embodiments, the C1ORF127 gene product has two less glycosylations than naturally occurring C1ORF127 gene product. In some embodiments, the C1ORF127 gene product has one more glycosylation than naturally occurring C1ORF127 gene product. In some embodiments, the C1ORF127 gene product has two more glycosylations than naturally occurring C1ORF127 gene product. In some embodiments, the different glycosylation is present in the portion of C1ORF127 gene product corresponding to SEQ ID NO: 4 or SEQ ID NO: 5 (e.g., in a putative glycosylation site in SEQ ID NO: 4 or SEQ ID NO: 5).

In some embodiments, the C1ORF127 gene product is a dimer, trimer, or multimer. In some embodiments, the C1ORF127 gene product is a homodimer, homotrimer, or homomultimer. In some embodiments, the C1ORF127 gene product exists in a different multimerization state than naturally occurring C1ORF127 gene product.

In some embodiments, the agent comprises a C1ORF127 gene product having a different composition, activity or activity level than native C1ORF127 gene product. In some embodiments, the C1ORF127 gene product has a blood glucose clearance activity that is about 1.1-fold, 1.2-fold, 1.3-fold, 1.4-fold, 1.5-fold, 1.6-fold, 1.7-fold, 1.8-fold, 2.0-fold, 2.5-fold, 3.0-fold, or more than a native C1ORF127 gene product. In some embodiments, the C1ORF127 gene product has a blood glucose clearance activity that is about 1%, 2.5%, 5%, 7.5%, 10%, 20%, 30%, 40%, 50% or less than a native C1ORF127 gene product. In some embodiments, the agent comprises a functional portion (i.e., functional fragment) of a C1ORF127 gene product. In some embodiments, the agent comprises a functional fragment of C1ORF127 gene product corresponding to SEQ ID NO: 3, SEQ ID NO: 4, or SEQ ID NO: 5, or a polypeptide sequence having at least about 80%, 85%, 90%, 91%, 92%, 93%, 94%, 95%, 96%, 97%, 98%, or 99% identity to SEQ ID NO: 3, SEQ ID NO: 4, or SEQ ID NO: 5.

In some embodiments, the agent comprises a C1ORF127 gene product comprising a furin cleavage site. In some embodiments, the agent comprises a C1ORF127 gene product without a PC2 cleavage site (e.g., LVKRG in SEQ ID NO: 2). In some embodiments, the agent comprises a C1ORF127 gene product with a furin cleavage site and without a PC2 cleavage site.

In some embodiments, the agent is a cell expressing C1ORF127 gene product. In some embodiments, the cell is an islet cell or a beta-cell. In some embodiments, the cell is a pancreatic delta cells. In some embodiments, the cell is autologous to the subject requiring treatment. In some embodiments, the cell is stem cell derived. In some embodiments, the stem cell derived cell is a stem cell derived beta cell. Methods of deriving beta cells are taught in the art. See, e.g., WO 2015/002724 published Jan. 8, 2015, herein incorporated by reference in its entirety. In some embodiments, the cell is encased in a microcapsule or semi-permeable membrane.

Aspects of the disclosure involve microcapsules comprising isolated populations of cells described herein, e.g., cells expressing a C1ORF127 gene product or functional variant or functional fragment thereof. Microcapsules are well known in the art. Suitable examples of microcapsules are described in the literature (e.g., Jahansouz et al., "Evolution of β-Cell Replacement Therapy in Diabetes Mellitus: Islet Cell Transplantation" *Journal of Transplantation* 2011; Volume 2011, Article ID 247959; Orive et al., "Application of cell encapsulation for controlled delivery of biological therapeutics", *Advanced Drug Delivery Reviews* (2013), http://dx.doi.org/10.1016/j.addr.2013.07.009; Hernandez et al., "Microcapsules and microcarriers for in situ cell delivery", *Advanced Drug Delivery Reviews* 2010; 62:711-730; Murua et al., "Cell microencapsulation technology: Towards clinical application", *Journal of Controlled Release* 2008; 132: 76-83; and Zanin et al., "The development of encapsulated cell technologies as therapies for neurological and sensory diseases", *Journal of Controlled Release* 2012; 160:3-13). Microcapsules can be formulated in a variety of ways. Exemplary microcapsules comprise an alginate core surrounded by a polycation layer covered by an outer alignate membrane. The polycation membrane forms a semipermeable membrane, which imparts stability and biocompatibility. Examples of polycations include, without limitation, poly-L-lysine, poly-L-ornithine, chitosan, lactose modified chitosan, and photopolymerized biomaterials. In some embodiments, the alginate core is modified, for example, to produce a scaffold comprising an alginate core having covalently conjugated oligopeptides with an RGD sequence (arginine, glycine, aspartic acid). In some embodiments, the alginate core is modified, for example, to produce a covalently reinforced microcapsule having a chemoenzymatically engineered alginate of enhanced stability. In some embodiments, the alginate core is modified, for example, to produce membrane-mimetic films assembled by in-situ polymerization of acrylate functionalized phospholipids. In some embodiments, microcapsules are composed of enzymatically modified alginates using epimerases. In some embodiments, microcapsules comprise covalent links between adjacent layers of the microcapsule membrane. In some embodiment, the microcapsule comprises a subsieve-size capsule comprising aliginate coupled with phenol moieties. In some embodiments, the microcapsule comprises a scaffold comprising alginate-agarose. In some embodiments, the cell is modified with PEG before being encapsulated within alginate. In some embodiments, the isolated populations of cells are encapsulated in photoreactive liposomes and alginate. It should be appreciate that the alginate employed in the microcapsules can be replaced with other suitable biomaterials, including, without limitation, PEG, chitosan, PES hollow fibers, collagen, hyaluronic acid, dextran with RGD, EHD and PEGDA, PMBV and PVA, PGSAS, agarose, agarose with gelatin, PLGA, and multi-layer embodiments of these.

In some embodiments, the agent further comprises a pharmaceutically acceptable carrier or excipient. As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the agents/compositions is contemplated. Supplementary active compounds can also be incorporated into the agents/compositions.

In some embodiments, the methods disclosed herein further comprises administration to the subject of one or more additional anti-diabetic therapeutics (e.g., Acarbose (Precose), Albiglutide (Tanzeum), Alogliptin (Nesina), Alogliptin and metformin (Kazano), Alogliptin and pioglitazone (Oseni), Bromocriptine mesylate (Cycloset, Parlodel), Canaglifozin (Invokana), Canagliflozin and metformin (Invokamet), Dapagliflozin (Farxiga), Dapagliflozin and metformin (Xigduo XR), Dulaglutide (Trulicity), Empagliflozin (Jardiance), Empagliflozin and linagliptin (Glyxambi), Empagliflozin and metformin (Synjardy), Exenatide Byetta), Glimepiride (Amaryl), Glyburide (DiaBeta, Glynase), Glyburide and metformin (Glucovance) Insulin aspart (NovoLog), Insulin degludec (Tresiba), Insulin glargine (Basaglar, Lantus, Toujeo), Insulin Isophane (Humulin N, Novolin N), Insulin Isophane/regular insulin (Humulin 70/30, Novolin 70/30), Insulin lispro (Humalog), Linagliptin (Tradjenta), Liraglutide (Victoza), Metformin (Glucophage), Miglitol (Glyset), Nateglinide (Starlix), Pioglitazone (Actos), Repaglinide (Prandin), Rosiglitazone Avandia), Rosiglitazone and glimepiride (Avandaryl), Rosiglitazone and metformin (Avandamet), Saxagliptin (Onglyza), Semaglutide (Ozempic), or Sitagliptin (Januvia)).

In some embodiments, administration of the agent improves blood glucose clearance. In some embodiments, administration of the agent returns blood glucose levels from a pathological level to a non-pathological level (e.g., from a hyperglycemic state to a normal state). In some embodiments, administration of the agent reduces blood glucose levels by about 5%, 10%, 15%, 20%, 25%, 30%, 35%, 40%, 45%, or more. In some embodiments, administration of the agent reduces blood glucose levels to about less than 140 mg/dL, about less than 100 mg/dL, about 60-90 mg/dL, or about 70-80 mg/dL. In some embodiments, administration of the agent does not cause hypoglycemia in the subject (e.g., a blood sugar of less than about 70 mg/dL, a blood sugar of less than about 60 mg/dL, or to a blood sugar level wherein the subject does not exhibit signs of hypoglycemia). In some embodiments, the blood glucose clearance property of the agent is independent of insulin activity.

In some embodiments, the agent has glucose sensitizer activity when administered to the subject. In some embodiments, the agent increases insulin activity, production or secretion when administered to a subject. In some embodiments, administration of the agent increases insulin activity, production or secretion by about 5%, 10%, 20%, 30%, 40%, 50%, 75%, 100%, or more. In some embodiments, administration of the agent increases insulin activity, production or secretion by about 1.1-fold, 1.2-fold, 1.3-fold, 1.4-fold, 1.5-fold, 1.6-fold, 2-fold, 2.5-fold, 3-fold, 3.5-fold, 5-fold, 10-fold, 50-fold, or more.

In some embodiments, the agent increases the rate of glucose turnover when administered to the subject. In some embodiments, administration of the agent increases glucose turnover by about 5%, 10%, 20%, 30%, 40%, 50%, 75%, 100%, or more. In some embodiments, administration of the agent increases glucose turnover about 1.1-fold, 1.2-fold, 1.3-fold, 1.4-fold, 1.5-fold, 1.6-fold, 2-fold, 2.5-fold, 3-fold, 3.5-fold, 5-fold, 10-fold, 50-fold, or more.

In some embodiments, the agent increases glycolysis when administered to the subject. In some embodiments, the agent increases the rate of glycolysis when administered to the subject. In some embodiments, administration of the agent increases glycolysis by about 5%, 10%, 20%, 30%, 40%, 50%, 75%, 100%, or more. In some embodiments, administration of the agent increases glycolysis about 1.1-fold, 1.2-fold, 1.3-fold, 1.4-fold, 1.5-fold, 1.6-fold, 2-fold, 2.5-fold, 3-fold, 3.5-fold, 5-fold, 10-fold, 50-fold, or more.

In some embodiments, the agent increases the rate of glycogen synthesis when administered to the subject. In some embodiments, the agent increases the rate of glycogen synthesis when administered to the subject. In some embodiments, administration of the agent increases glycogen synthesis by about 5%, 10%, 20%, 30%, 40%, 50%, 75%, 100%, or more. In some embodiments, administration of the agent increases glycogen synthesis about 1.1-fold, 1.2-fold, 1.3-fold, 1.4-fold, 1.5-fold, 1.6-fold, 2-fold, 2.5-fold, 3-fold, 3.5-fold, 5-fold, 10-fold, 50-fold, or more. In some embodiments, the agent has glucagon-like activity when administered to the subject.

In some embodiments, the subject has diabetes (e.g., Type I diabetes or Type II diabetes), metabolic syndrome, glucose intolerance, or obesity. In some embodiments, the subject has diabetes. In some embodiments, the subject's genome comprises a mutant or variant form of C1ORF127. In some embodiments, the variant is one of the following: 1_11014118_C_T, 1_11015165_A_G, 1_11008102_G_A, 1_11009679_G_A, 1_11007881_G_T, 1_11008778_T_A,C, 1_11008799_G_C, 1_11008417_G_A, 1_11008127_C_T, 1_11009703_C_T, 1_11008594_A_T, 1_11007997_C_T, 1_11024271_G_T,A, 1_11008685_T_C, 1_11009716_C_G, 1_11009844 G_A, 1_11008417_G_A, 1_11036248_G_A, 1_11024271_G_T,A, 1_11009844_G_A, 1_11008799_G_C, 1_11008778_T_A,C, 1_11008685_T_C, 1_11014118_C_T, 1_11009716_C_G, 1_11008102_G_A, 1_11007895_G_T, 1_11008127_C_T, 1_11009703_C_T, 1_11008594_A_T, 1_11009679_G_A, 1_11014127_C_T, 1_11008844_C_G,T, 1_11015165_A_G, 1_11009703_C_T, 1_11009679_G_A, 1_11008594_A_T, 1_11008102_GA, 1_11009844_G_A, 1_11007895_G_T, 1_11008127_C_T, 1_11008417_G_A, 1_11007724_C_T, 1_11024271_G_T,A, 1_11008778_T_A,C, 1_11009716_C_G, 1_11015165_A_G, 1_11014118_C_T, 1_11008799_G_C, 1_11007881_G_T, 1_11008685_T_C, 1_11007997_C_T, 1_11015165_A_G, 1_11008102_G_A, 1_11008685_T_C, 1_11008799_G_C, 1_11008127_C_T, 1_11009679_G_A, 1_11014118_C_T, 1_11009703_C_T, 1_11007724_C_T, 1_11008594_A_T, 1_11009716_C_G, 1_11007895 G_T, 1_11007881_G_T, 1_11008778_T_A,C, 1_11024271_G_T, A, or 1_11007997_C_T.

In some embodiments, the C1ORF127 variant is associated with diabetes and high BMI. In some embodiments, the C1ORF127 variant associated with diabetes and high BMI is 1_11033415_G_A. In some embodiments, the C1ORF127 variant is associated with elevated fasting glucose levels. In some embodiments, the C1ORF127 variant associated with elevated fasting glucose levels is 1_11014118_C_T. In some embodiments, the variant is associated with type 1 diabetes. In some embodiments, the variant is associated with type 2 diabetes. In some embodiments, the variant is associated with high BMI.

In some embodiments, administration of the agent corrects a genetic defect in the subject causing aberrant expression or activity of the C1ORF127 gene product. In some embodiments, the genetic defect is a C1ORF127 variant as identified herein. In some embodiments, the genetic defect is variant 1_11033415_G_A. In some embodiments, the genetic defect is variant 1_11014118_C_T. In some embodiments, the agent comprises a targetable nuclease. In some embodiments, the agent further comprises gRNA targeting the nuclease to the genetic defect. In some embodiments, the agent further comprises a donor nucleic acid for correcting the defect by homology directed repair (HDR) after the generation of a DNA break at the defect site by the targetable nuclease.

Targetable nucleases (e.g., site specific nucleases) generate DNA breaks in the genome at a selected target site and can be used to produce precise genomic modifications. DNA breaks, e.g., double-stranded DNA breaks, can be repaired by various DNA repair pathways. Homologous recombination (HR) mediated repair (also termed homology-directed repair (HDR)) uses homologous donor DNA as a template to repair the break. If the sequence of the donor DNA differs from the genomic sequence, this process leads to the introduction of sequence changes into the genome. Precise modifications to the genome can be made by providing donor DNA comprising an appropriate sequence. Modifications that can be generated using targetable nucleases include insertions, deletions, or substitutions of one or more nucleotides, or introducing an exogenous DNA segment such as an expression cassette (a nucleic acid comprising a sequence to be expressed and appropriate expression control elements, such as a promoter, to cause the sequence to be expressed in a cell) or tag at a selected location in the genome.

There are currently four main types of targetable nuclease in use: zinc finger nucleases (ZFNs), transcription activator-like effector nucleases (TALENs), and RNA-guided nucleases (RGNs) such as the Cas proteins of the CRISPR/Cas Type II system, and engineered meganucleases. ZFNs and TALENs comprise the nuclease domain of the restriction enzyme FokI (or an engineered variant thereof) fused to a site-specific DNA binding domain (DBD) that is appropriately designed to target the protein to a selected DNA sequence. In the case of ZFNs, the DNA binding domain comprises a zinc finger DBD. In the case of TALENs, the site-specific DBD is designed based on the DNA recognition code employed by transcription activator-like effectors (TALEs), a family of site-specific DNA binding proteins found in plant-pathogenic bacteria such as *Xanthomonas* species. The Clustered Regularly Interspaced Short Palindromic Repeats (CRISPR) Type II system is a bacterial adaptive immune system that has been modified for use as an RNA-guided endonuclease technology for genome engineering. The bacterial system comprises two endogenous bacterial RNAs called crRNA and tracrRNA and a CRISPR-associated (Cas) nuclease, e.g., Cas9. The tracrRNA has partial complementarity to the crRNA and forms a complex with it. The Cas protein is guided to the target sequence by the crRNA/tracrRNA complex, which forms a RNA/DNA hybrid between the crRNA sequence and the homologous sequence in the target. For use in genome modification, the crRNA and tracrRNA components are often combined into a single chimeric guide RNA (sgRNA or gRNA) in which the targeting specificity of the crRNA and the properties of the tracrRNA are combined into a single transcript that localizes the Cas protein to the target sequence so that the Cas protein can cleave the DNA. The sgRNA often comprises an approximately 20 nucleotide guide sequence complementary to the desired target sequence followed by about 80 nt of hybrid crRNA/tracrRNA. One of ordinary skill in the art appreciates that the guide RNA need not be perfectly complementary to the target sequence. For example, in some embodiments it may have one or two mismatches.

In some embodiments, one or more guide sequences (e.g., guide RNA, gRNA) is a naturally occurring RNA sequence, a modified RNA sequence (e.g., a RNA sequence comprising one or more modified bases), a synthetic RNA sequence, or a combination thereof. As used herein a "modified RNA" is an RNA comprising one or more modifications (e.g., RNA comprising one or more non-standard and/or non-naturally occurring bases and/or modifications to the backbone, internucleoside linkage(s) and/or sugar). Methods of modifying bases of RNA are well known in the art. Examples of such modified bases include those contained in the nucleosides 5-methylcytidine (5mC), pseudouridine (Ψ), 5-methyluridine, 2'0-methyluridine, 2-thiouridine, N-6 methyladenosine, hypoxanthine, dihydrouridine (D), inosine (I), and 7-methylguanosine (m7G). It should be noted that any number of bases, sugars, or backbone linkages in a RNA sequence can be modified in various embodiments. It should further be understood that combinations of different modifications may be used. In some embodiments an RNA comprises one or more modifications selected from: phosphorothioate, 2'-OMe, 2'-F, 2'-constrained ethyl (2'-cEt), 2'-OMe 3' phosphorothioate (MS), and 2'-OMe 3-thioPACE (MSP) modifications. In some embodiments a modification may stabilize the RNA and/or increase its binding affinity to a complementary sequence.

In some embodiments, the one or more guide sequences comprise at least one locked nucleic acid (LNA) unit, such as 1, 2, 3, 4, 5, 6, 7, or 8 LNA units, such as from about 3-7 or 4-8 LNA units, or 3, 4, 5, 6 or 7 LNA units. In some embodiments, all the nucleotides of the one or more guide sequences are LNA. In some embodiments, the one or more guide sequences may comprise both beta-D-oxy-LNA, and one or more of the following LNA units: thio-LNA, amino-LNA, oxy-LNA, and/or ENA in either the beta-D or alpha-L configurations or combinations thereof. In some embodiments all LNA cytosine units are 5'methyl-cytosine.

In some embodiments, the one or more guide sequences is a morpholino. Morpholinos are typically synthetic molecules, of about 25 bases in length and bind to complementary sequences of RNA by standard nucleic acid base-pairing. Morpholinos have standard nucleic acid bases, but those bases are bound to morpholine rings instead of deoxyribose rings and are linked through phosphorodiamidate groups instead of phosphates.

In some embodiments, a guide sequence can vary in length from about 8 base pairs (bp) to about 200 bp. In some embodiments, each of one or more guide sequences can be about 9 to about 190 bp; about 10 to about 150 bp; about 15 to about 120 bp; about 20 to about 100 bp; about 30 to about 90 bp; about 40 to about 80 bp; about 50 to about 70 bp in length.

Chemical modifications and methods of synthesizing guide RNAs (guide sequences) are known in the art. See WO/2016/164356, herein incorporated by reference in its entirety.

The portion of each genomic sequence (e.g., target sequence of interest, gene of interest, genetic defect) to which each guide sequence is complementary or homologous to can also vary in size. In particular aspects, the portion of each genomic sequence to which the guide sequence is complementary or homologous to can be about 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38 39, 40, 41, 42, 43, 44, 45, 46 47, 48, 49, 50, 51, 52, 53, 54, 55, 56, 57, 58, 59 60, 61, 62, 63, 64, 65, 66, 67, 68, 69, 70, 71, 72, 73, 74, 75, 76, 77, 78, 79, 80 81, 82, 83, 84, 85, 86, 87 88, 89, 90, 81, 92, 93, 94, 95, 96, 97, 98, or 100 nucleotides (contiguous nucleotides) in length. In some embodiments, each guide sequence can be at least about 70%, 75%, 80%, 85%, 90%, 95%, 100%, etc. identical, complementary or similar to the portion of each genomic sequence. In some embodiments, each guide sequence is completely or partially identical, complementary or similar to each genomic sequence. For example, each guide sequence can differ from perfect complementarity or homology to the portion of the genomic sequence by about 1, 2, 3, 4, 5, 6, 7, 8, 9, 10, 11, 12, 13, 14, 15, 16, 17, 18, 19, 20, etc. nucleotides. In some embodiments, one or more guide sequences are perfectly complementary or homologous (100%) across at least about 10 to about 25 (e.g., about 20) nucleotides of the genomic sequence.

The genomic target sequence (e.g., genomic locus of interest, gene of interest, target sequence of interest, genetic defect) should also be immediately followed by a Protospacer Adjacent Motif (PAM) sequence. The PAM sequence is present in the DNA target sequence but not in a guide sequence. The Cas protein will be directed to any DNA sequence with the correct target sequence followed by the PAM sequence. The PAM sequence varies depending on the species of bacteria from which the Cas protein was derived. In some embodiments, the targetable nuclease comprises a Cas9 protein. For example, Cas9 from *Streptococcus pyogenes* (Sp), *Neisseria meningitides*, *Staphylococcus aureus*, *Streptococcus thermophiles*, or *Treponema denticola* may be used. The PAM sequences for these Cas9 proteins are NGG, NNNNGATT, NNAGAA, NAAAAC, respectively. A number of engineered variants of the site-specific nucleases have been developed and may be used in certain embodiments. For example, engineered variants of Cas9 and FokI are known in the art. Furthermore, it will be understood that a biologically active fragment or variant can be used. Other variations include the use of hybrid targetable nucleases. For example, in CRISPR RNA-guided FokI nucleases (RFNs) the FokI nuclease domain is fused to the amino-terminal end of a catalytically inactive Cas9 protein (dCas9) protein. RFNs act as dimers and utilize two guide RNAs (Tsai, Q S, et al., *Nat Biotechnol.* 2014; 32(6): 569-576). Site-specific nucleases that produce a single-stranded DNA break are also of use for genome editing. Such nucleases, sometimes termed "nickases" can be generated by introducing a mutation (e.g., an alanine substitution) at key catalytic residues in one of the two nuclease domains of a targetable nuclease that comprises two nuclease domains (such as ZFNs, TALENs, and Cas proteins). Examples of such mutations include D10A, N863A, and H840A in SpCas9 or at homologous positions in other Cas9 proteins. A nick can stimulate HDR at low efficiency in some cell types. Two nickases, targeted to a pair of sequences that are near each other and on opposite strands can create a single-stranded break on each strand ("double nicking"), effectively generating a DSB, which can be repaired by HDR using a donor DNA template (Ran, F. A. et al. Cell 154, 1380-1389 (2013).

The term "donor nucleic acid" or "donor" refers to an exogenous nucleic acid segment that, when provided to a cell, e.g., along with a targetable nuclease, can be used as a template for DNA repair by homologous recombination and thereby cause site-specific genome modification (sometimes termed "genome editing"). The modifications can include insertions, deletions, or substitutions of one or more nucleotides, or introducing an exogenous DNA segment such as an expression cassette or tag at a selected location in the genome. A donor nucleic acid typically comprises sequences that have homology to the region of the genome at which the genomic modification is to be made. The donor may contain one or more single base changes, insertions, deletions, or other alterations with respect to the genomic sequence, so long as it has sufficient homology to allow for homology-directed repair. In the present invention, the donor nucleic acid is the nucleic acid sequence comprising the reporter gene and WPRE flanked by the homology arms. The homology arms are homologous to genomic sequences flanking a location in genomic DNA at which the insertion is to be made (e.g., DNA break). One of ordinary skill in the art also appreciates that the homology need not extend all the way to the DNA break. For example, in some embodiments the homology begins no more than 100 bp away from the break, e.g., between 1 and 100 bp away, e.g., 1-50 bp away, e.g., 1-15 bp away, from the break.

Donor nucleic acid can be provided, for example, in the form of DNA plasmids, PCR products, or chemically synthesized oligonucleotides, and may be double-stranded or single-stranded in various embodiments. The size of the donor nucleic can vary from as small as about 40 base pairs (bp) to about 10 kilobases (kb), or more. In some embodiments the donor nucleic is between about 1 kb and about 5 kb long.

Those of ordinary skill in the art are aware of methods for performing site-specific genome modification using targetable nucleases and will be able to apply such methods to repair a genetic defect associated with aberrant expression or activity of C1ORF127 as taught herein. Those of ordinary skill in the art can, for example, design appropriate guide RNAs, TALENs, or ZFNs to generate a DNA break at a selected location in the genome, can design a targeting vector (e.g., comprising homology arms) to promote HDR at a DNA break generated by a targetable nuclease, and are aware of appropriate methods that can be used to introduce a targetable nuclease into cells and, where appropriate, a donor nucleic acid, and/or guide RNA. A targetable nuclease may be targeted to a unique site in the genome of a mammalian cell by appropriate design of the nuclease or guide RNA. A nuclease or guide RNA may be introduced into cells by introducing a nucleic acid that encodes it into the cell. Standard methods such as plasmid DNA transfection, viral vector delivery, transfection with synthetic mRNA (e.g., capped, polyadenylated mRNA), or microinjection can be used. If DNA encoding the nuclease or guide RNA is introduced, the coding sequences should be operably linked to appropriate regulatory elements for expression, such as a promoter and termination signal. In some embodiments a sequence encoding a guide RNA is operably linked to an RNA polymerase III promoter such as U6 or tRNA promoter. In some embodiments one or more guide RNAs and Cas protein coding sequences are transcribed from the same nucleic acid (e.g., plasmid). In some embodiments multiple guide RNAs are transcribed from the same plasmid or from different plasmids or are otherwise introduced into the cell. The multiple guide RNAs may direct Cas9 to different target sequences in the genome, allowing for multiplexed genome editing. In some embodiments a nuclease protein (e.g., Cas9) may comprise or be modified to comprise a nuclear localization signal (e.g., SV40 NLS). A nuclease protein may be introduced into cells, e.g., using protein transduction. Nuclease proteins, guide RNAs, or both, may be introduced using microinjection. Methods of using targetable nucleases, e.g., to perform genome editing, are described in numerous publications, such as *Methods in Enzymology*, Doudna J A, Sontheimer E J. (eds), The use of CRISPR/Cas9, ZFNs, and TALENs in generating site-specific genome alterations. Methods Enzymol. 2014, Vol. 546 (Elsevier); Carroll, D., Genome Editing with Targetable Nucleases, Annu. Rev. Biochem. 2014. 83:409-39, and references in either of these. See also U.S. Pat. Pub. Nos. 20140068797, 20140186919, 20140170753 and/or PCT/US2014/034387 (WO/2014/172470). Each of these references is incorporated by reference in its entirety.

Agents and Compositions

Some aspects of the disclosure are related to agents that increase the level or activity of a C1ORF127 gene product when administered to a subject. The agents may be any agent as described herein. The C1ORF127 gene product may be any C1ORF127 gene product as described herein. In some embodiments, the agent increases the level or activity of endogenous C1ORF127 gene product when administered to a subject. In some embodiments, the agent modulates (e.g., increases or decreases) the expression of endogenous C1ORF127 gene product when administered to a subject. The agent may increase or decrease expression by any amount and is not limited. In some embodiments, the agent increases expression by about 1.1-fold, 1.2-fold, 1.3-fold, 1.4-fold, 1.5-fold, 1.6-fold, 1.7-fold, 1.8-fold, 2.0-fold, 2.5-fold, 3.0-fold, 5-fold, or more. In some embodiments, the agent increases expression or decreases expression by about 1%, 2.5%, 5%, 7.5%, 10%, 20%, 30%, 40%, 50%, 60%, 70%, 80%, 90%, 100%, 125%, 150%, 200%, 300%, 500%, or more.

In some embodiments, the agent modulates (e.g., increases or decreases) the secretion of endogenous C1ORF127 gene product when administered to a subject. The agent may increase or decrease secretion by any amount and is not limited. In some embodiments, the agent increases secretion by about 1.1-fold, 1.2-fold, 1.3-fold, 1.4-fold, 1.5-fold, 1.6-fold, 1.7-fold, 1.8-fold, 2.0-fold, 2.5-fold, 3.0-fold, 5-fold, or more. In some embodiments, the agent increases secretion or decreases secretion by about 1%, 2.5%, 5%, 7.5%, 10%, 20%, 30%, 40%, 50%, 60%, 70%, 80%, 90%, 100%, 125%, 150%, 200%, 300%, 500%, or more.

In some embodiments, the agent comprises a small molecule, a protein, or a nucleic acid. In some embodiments, the agent comprises C1ORF127 gene product having at least one different post-translational modification than native C1ORF127 gene product. In some embodiments, the agent comprises C1ORF127 gene product having at least one substituted, deleted, or added amino acid than native C1ORF127 gene product. In some embodiments, the agent comprises C1ORF127 gene product having a different activity or activity level than native C1ORF127 gene product. In some embodiments, wherein the agent comprises a functional portion of the C1ORF127 gene product.

In some embodiments, the agent further comprises a pharmaceutically acceptable carrier or excipient. The pharmaceutically acceptable carrier or excipient is not limited and may be any pharmaceutically acceptable carrier or excipient described herein.

Therapeutic compositions containing at least one agent can be conventionally administered in a unit dose, for example. The term "unit dose" when used in reference to a therapeutic composition refers to physically discrete units suitable as unitary dosage for the subject, each unit containing a predetermined quantity of active material calculated to produce the desired therapeutic effect in association with the required physiologically acceptable diluent, i.e., carrier, or vehicle.

The dosage ranges for the agent depends upon the potency, and are amounts large enough to produce the desired effect e.g., improve blood glucose clearance. The dosage should not be so large as to cause unacceptable adverse side effects. Generally, the dosage will vary with the age, condition, and sex of the patient and can be determined by one of skill in the art. The dosage can also be adjusted by the individual physician in the event of any complication. Typically, the dosage can range from 0.001 mg/kg body weight to 0.5 mg/kg body weight. In one embodiment, the dose range is from 5 µg/kg body weight to 30 µg/kg body weight.

Administration of the doses recited above can be repeated. In some embodiments, the doses are given once a day, or multiple times a day, for example, but not limited to, three times a day. In some embodiments, the doses recited above are administered daily for weeks or months. The duration of treatment depends upon the subject's clinical progress and responsiveness to therapy.

Precise amounts of active ingredient required to be administered depend on the judgment of the practitioner and are particular to each individual. However, suitable dosage ranges for systemic application are disclosed herein and depend on the route of administration. Suitable regimes for administration are also variable, but are typified by an initial administration followed by repeated doses at one or more intervals by a subsequent administration. Alternatively, continuous intravenous infusion sufficient to maintain concentrations in the blood in the ranges specified for in vivo therapies are contemplated. In some embodiments, the dosage range is sufficient to maintain concentrations in the blood in the range found in the blood of a population of normal, healthy human subjects.

In some embodiments, the agent comprises an additional anti-diabetic therapeutic. The additional anti-diabetic therapeutic is not limited and may be any anti-diabetic therapeutic described herein. The additional anti-diabetic therapeutic may be administered together or separately. In some embodiments, the additional anti-diabetic therapeutic is in a single dosage form. In some embodiments, the additional anti-diabetic therapeutic is in a separate dosage form.

In some embodiments, the agent improves blood glucose clearance when administered to a subject. In some embodiments, the agent does not cause hypoglycemia when administered to a subject.

In some embodiments, the subject has diabetes (e.g., Type I diabetes or Type II diabetes), metabolic syndrome, glucose intolerance, or obesity. In some embodiments, the subject has diabetes. In some embodiments, the subject is human or murine.

In some embodiments, the agent comprises a C1ORF127 gene product of SEQ ID NO: 2 or a functional portion or functional variant thereof. In some embodiments, the agent comprises a nucleic acid coding for a C1ORF127 gene product, a functional portion, or functional variant thereof, wherein the nucleic acid comprises the sequence of SEQ ID NO: 1 or a portion thereof. In some embodiments, the agent comprises a nucleic acid coding for a C1ORF127 gene product a functional portion or functional variant thereof, wherein the nucleic acid comprises a sequence having at least 80%, 85%, 90%, 91%, 92%, 93%, 94%, 95%, 96%, 97%, 98%, or 99% homology to SEQ ID NO: 1 or a portion thereof.

In some embodiments, the agent corrects a genetic defect in the subject causing aberrant expression or activity of the C1ORF127 gene product. In some embodiments, the agent comprises a targetable nuclease as described herein. In some embodiments, the agent comprises guide RNA and, optionally, donor nucleic acid as described herein.

Methods of Diagnosing

Some aspects of the disclosure are directed to methods of diagnosing a C1ORF127-related disorder or an increased risk for developing a C1ORF127-related disorder in a test individual, comprising determining a C1ORF127 gene product level in a sample obtained from said test individual, wherein a C1ORF127 gene product level that is increased or decreased in said test individual compared to a C1ORF127 gene product level in a normal individual is indicative of a C1ORF127-related disorder. The test individual may be any subject described herein.

The level of C1ORF127 which is indicative of a C1ORF127-related condition may be defined as the decreased level present in samples from individuals known to have a C1ORF127-related disorder over the C1ORF127 level in samples from individuals known to be free of a C1ORF127-related disorder. The level of C1ORF127 may be, for example, at least 1.1 fold, 1.2 fold, 1.3 fold, 1.4 fold, 1.5 fold, 1.6 fold, 1.7 fold, 1.8 fold, 1.9 fold, 2.0 fold, 2.1 fold, 2.2 fold, 2.3 fold, 2.4 fold, 2.5 fold, 2.6 fold, 2.7 fold, 2.8 fold, 2.9 fold, 3.0 fold, 3.1 fold, 3.2 fold, 3.3 fold, 3.4 fold, 3.5 fold, 3.6 fold, 3.7 fold, 3.8 fold, 3.9 fold, 4.0 fold, 4.1 fold, 4.2 fold, 4.3 fold, 4.4 fold, 4.5 fold, 4.6 fold, 4.7 fold, 4.8 fold, 4.9 fold, 5.0 fold, 5.1 fold, 5.2 fold, 5.3 fold, 5.4 fold, 5.5 fold, 5.6 fold, 5.7 fold, 5.8 fold, 5.9 fold, 6.0 fold, 10 fold, 15 fold, 20 fold, 50 fold or 100 fold higher or lower in a sample from an individual with a C1ORF127-related disorder.

The C1ORF127 gene product (e.g., protein) is detected and/or quantified in the sample using any of a number of well recognized immunological binding assays (see, e.g., U.S. Pat. Nos. 4,366,241; 4,376,110; 4,517,288; and 4,837,168). For a review of general immunoassays, see also Methods in Cell Biology Volume 37: Antibodies in Cell Biology, Asai, ed. Academic Press, Inc. New York (1993); Basic and Clinical Immunology 7th Edition, Stites & Terr, eds. (1991).

In some embodiments, the C1ORF127 gene product in the sample can also be detected and quantified using immunoblot (Western blot) analysis. Immunoblotting generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with antibodies that specifically bind the C1ORF127 gene product. The anti-C1ORF127 gene product antibodies specifically bind to C1ORF127 gene product on the solid support. These antibodies may be directly labeled or alternatively may be subsequently detected using labeled antibodies (e.g., labeled sheep anti-mouse antibodies) that specifically bind to the anti-C1ORF127 gene product antibody.

In some embodiments, quantitative assays of C1ORF127 gene product are deemed to show a positive result, e.g., elevated or decreased C1ORF127 gene product level, when the measured C1ORF127 gene product level is greater or less than the level measured or known for a control sample (e.g. either a level known or measured for a normal healthy individual or a "baseline/reference" level determined at a different time for the same individual. In a particularly preferred embodiment, the assay is deemed to show a positive result when the difference between sample and "control" is statistically significant (e.g. at the 85% or greater, preferably at the 90% or greater, more preferably at the 95% or greater and most preferably at the 98% or greater confidence level).

In some embodiments, the C1ORF127 gene product level is detected in a blood sample. Methods of obtaining and processing the blood sample are known in the art and are not limited herein.

Some aspects of the disclosure are directed to methods of diagnosing a C1ORF127-related disorder or an increased risk for developing a C1ORF127-related disorder in a test individual, comprising screening the test individual for a mutation in C1ORF127. Methods of detecting genetic mutations are known in the art and not limited. In some embodiments, the C1ORF127-related disorder is diabetes.

Methods of Screening

Some aspects of the disclosure are directed to methods of screening for a C1ORF127 gene product receptor agonist, comprising contacting a cell responsive to the C1ORF127 gene product with a test agent and determining the response of the cell, wherein if the cell responds then the test agent is identified as a C1ORF127 gene product receptor agonist. In some embodiments, the cell response is glucose uptake. In some embodiments, the cell is further contacted with an insulin receptor antagonist. In some embodiments, the insulin receptor antagonist is S961. In some embodiments, an animal (e.g., a subject as described herein) having the cell is used.

Methods for Enriching for mRNAs Coding for Secreted and Membrane Bound Proteins

Some aspects of the disclosures are related to methods of enriching for mRNAs coding for secreted and membrane bound proteins, comprising: providing a cell comprising a Endoplasmic Reticulum (ER) translocon having a label, performing sub-cellular fractionalization of the cell and isolating an ER fraction containing the label, and isolating and sequencing mRNA contained in the isolated ER fraction containing the label.

The component of the ER translocon having a label is not limited. In some embodiments, the labeled ER translocon component is Sec61, the oligosaccharyl transferase complex, the TRAP complex, or the membrane protein TRAM. In some embodiments, the ER translocon component SEC61b has the label.

Methods of adding a label to an ER translocon component are not limited. In some embodiments, the cell is genetically modified to express a label with the translocon component. The methods of genetic modification of the cell are not limited and any known in the art. In some embodiments, the cell is genetically using a targetable nuclease as described herein. In some embodiments, the label is a fluorescent label. In some embodiments the fluorescent label is a green fluorescent protein, red fluorescent protein, or infrared fluorescent protein.

In some embodiments, the label is transiently expressed or only under certain cellular conditions. In some embodiments, the certain conditions are the present of a site specific recombinase (e.g. Cre/Lox). For instance, the label can be added to the genome along with a stop codon flanked by LoxP. Upon activation/addition of Cre, the stop codon would be removed during recombination and the label expressed along with the translocon component.

The term "site-specific recombinase" (also referred to simply as a "recombinase" herein) refers to a protein that can recognize and catalyze the recombination of DNA between specific sequences in a DNA molecule. Such sequences may be referred to as "recombination sequences" or "recombination sites" for that particular recombinase. Tyrosine recombinases and serine recombinases are the two main families of site-specific recombinase. Examples of site-specific recombinase systems include the Cre/Lox system (Cre recombinase mediates recombination between loxP), the Flp/Frt system (Flp recombinase mediates recombination between FRT sites), and the PhiC31 system (PhiC31 recombinase mediates DNA recombination at sequences known as attB and attP sites). Recombinase systems similar to Cre include the Dre-rox, VCre/VloxP, and SCre/SloxP systems (Anastassiadis K, et al. (2009) Dis Model Mech 2(9-10):508-515; Suzuki E, Nakayama M (2011) Nucl. Acids Res. (2011) 39 (8): e49. It should be understood that reference to a particular recombinase system is intended to encompass the various engineered and mutant forms of the recombinases and recombination sites and codon-optimized forms of the coding sequences known in the art. DNA placed between two loxP sites is said to be "floxed". A gene may be modified by the insertion of two loxP sites that allow the excision of the floxed gene segment through Cre-mediated recombination. In some embodiments, expression of Cre may be under control of a cell type specific, cell state specific, or inducible expression control element (e.g., cell type specific, cell state specific, or inducible promoter) or Cre activity may be regulated by a small molecule. For example, Cre may be fused to a ligand binding domain of a receptor (e.g., a steroid hormone receptor) so that its activity is regulated by receptor ligands. Cre-ER(T) or Cre-ER(T2) recombinases may be used, which comprise a fusion protein between a mutated ligand binding domain of the human estrogen receptor (ER) and Cre, the activity of which can be induced by, e.g., 4-hydroxy-tamoxifen. Placing Lox sequences appropriately allows a variety of genomic manipulations.

In some embodiments, step b) of the method comprises contacting the cell with a protein synthesis inhibitor, solubilizing the cell plasma membrane, and immunoprecipitating the ER.

The protein synthesis inhibitor is not limited and may be any suitable protein synthesis inhibitor that keeps the labeled translocon associated with the ER. In some embodiments, the protein synthesis inhibitor blocks translational elongation. In some embodiments, the protein synthesis inhibitor is one identified in Chan et. al., Eukaryotic protein synthesis inhibitors identified by comparison of cytotoxicity profiles, RNA 2004. 10: 528-543. In some embodiments, the protein synthesis inhibitor is cyclohexamide.

In some embodiments, the cell plasma membrane is solubilized with step-wise concentrations of detergent. In some embodiments, the plasma membrane followed by the ER membrane are solubilized in a step-wise manner. Any suitable detergent or combinations of detergents known in the art may be used and are not limited. Methods of solubilizing plasma membrane can be practiced by those skilled in the art. In some embodiments, the detergent is digitonin and/or n-Dodecyl-B-D-Maltoside (DDM).

Methods of immunoprecipitation are also not limited and may be by any suitable method known in the art. In some embodiments, the ER is immunoprecipitated with an antibody specific for the label or for the labeled translocon component. In some embodiments, the label is GFP and the antibody is an anti-GFP antibody. In some embodiments, the antibody is attached to a magnetic bead or other substrate.

The method of sequencing the mRNA is not limited and may be any suitable method known in the art. In some embodiments, the mRNA is sequenced by next generation sequencing.

The cell of the methods and compositions described herein is not limited and may be any suitable cell. In some embodiments, the cell is a stem cell (e.g., an embryonic stem cell, a mammalian embryonic stem cell, a human embryonic stem cell, a murine embryonic stem cell). In some embodiments, the cell is an embryonic stem cell. In some embodiments, the cell is an induced pluripotent stem cell.

In some embodiments, cells include somatic cells, stem cells, mitotic or post-mitotic cells, neurons, fibroblasts, or zygotes. Stem cells may include totipotent, pluripotent, multipotent, oligopotent and unipotent stem cells. Specific examples of stem cells include embryonic stem cells, fetal stem cells, adult stem cells, and induced pluripotent stem cells (iPSCs) (e.g., see U.S. Published Application Nos. 2010/0144031, 2011/0076678, 2011/0088107, 2012/0028821 all of which are incorporated herein by reference).

Somatic cells may be primary cells (non-immortalized cells), such as those freshly isolated from an animal, or may be derived from a cell line capable of prolonged proliferation in culture (e.g., for longer than 3 months) or indefinite proliferation (immortalized cells). Adult somatic cells may be obtained from individuals, e.g., human subjects, and cultured according to standard cell culture protocols available to those of ordinary skill in the art. Somatic cells of use in aspects of the invention include mammalian cells, such as, for example, human cells, non-human primate cells, or rodent (e.g., mouse, rat) cells. They may be obtained by well-known methods from various organs, e.g., skin, lung, pancreas, liver, stomach, intestine, heart, breast, reproductive organs, muscle, blood, bladder, kidney, urethra and other urinary organs, etc., generally from any organ or tissue containing live somatic cells. Mammalian somatic cells useful in various embodiments include, for example, fibroblasts, Sertoli cells, granulosa cells, neurons, pancreatic cells, epidermal cells, epithelial cells, endothelial cells, hepatocytes, hair follicle cells, keratinocytes, hematopoietic cells, melanocytes, chondrocytes, lymphocytes (B and T lymphocytes), macrophages, monocytes, mononuclear cells, cardiac muscle cells, skeletal muscle cells, etc. In some embodiments, the cell is a beta-cell.

In some embodiments, the cell is a diseased cell or exhibits a pathological state. In some embodiments, the cell is differentiated cell from an induced pluripotent stem cell. In some embodiments, the induced pluripotent stem cell is derived from a subject having a disease or condition of interest. In some embodiments, the induced pluripotent stem cell is from a subject having diabetes or a risk of developing diabetes.

The diseases and conditions are not limited. In some embodiments, the diseases or conditions are selected from a metabolic disease, a cardiovascular disease, a circulatory or vascular disease, a neurological disease, a gastrointestinal disease (e.g., inflammatory bowel disease, Crohn's disease), and a disease associated with aging.

In some embodiments, the cell is undergoing a stress response (e.g., hypoxia, hyperglycemia, hypoglycemia, hypoxia/reperfusion).

In some embodiments, the cell is responding to a stimulus when contacted with a protein synthesis inhibitor. In some embodiments, the stimulus is a hormone (e.g., insulin). In some embodiments, the stimulus is an environmental condition (e.g., low oxygen, reperfusion). In some embodiments, the stimulus is insulin.

In some embodiments, the method further comprises performing the method of enriching for mRNAs coding for secreted and membrane bound proteins on a control cell, and comparing the mRNA's isolated from the cell to the mRNA's isolated from the control cell.

Applications of ER-Seq:

1. ER-seq can be used to compare in-vitro generated beta-cells from non-diabetic and diabetic patients to find novel disease biomarkers by specifically isolating RNAs that code for secreted proteins and comparing them among the two test groups.

2. ER-seq can be used to identify secreted peptide biomarkers produced by dysfunctional beta cells.

3. Induce stress response in vitro to identify biomarkers for beta-cell dysfunction 4. By generating assays that look for the elimination of the secreted distressed protein, we can find ways to protect beta-cells at the onset of T1D.

5. Marking other cells and discovering their complement of secreted proteins.

Non-Human Animals

Some aspects of the invention are directed to a non-human animal capable of expressing a labeled SEC61b protein. In some embodiments, expression of the labeled protein is inducible. In some embodiments, the labeled protein has Cre-dependent expression. In some embodiments, the non-human animal has inducible expression of the labeled SEC16b protein in beta-cells. The label is not limited and may be any suitable label in the art. In some embodiments, the label is a fluorescent protein. In some embodiments, the label is Green Fluorescent Protein (GFP). In some embodiments, the non-human animal is a mouse or rat. In some embodiments, the non-human animal is a model of diabetes (e.g., NOD model of type 1 diabetes, model of type 1 diabetes).

The practice of the present invention will typically employ, unless otherwise indicated, conventional techniques of cell biology, cell culture, molecular biology, transgenic biology, microbiology, recombinant nucleic acid (e.g., DNA) technology, immunology, and RNA interference (RNAi) which are within the skill of the art. Non-limiting descriptions of certain of these techniques are found in the following publications: Ausubel, F., et al., (eds.), Current Protocols in Molecular Biology, Current Protocols in Immunology, Current Protocols in Protein Science, and Current Protocols in Cell Biology, all John Wiley & Sons, N.Y., edition as of December 2008; Sambrook, Russell, and Sambrook, Molecular Cloning: A Laboratory Manual, 3rd ed., Cold Spring Harbor Laboratory Press, Cold Spring Harbor, 2001; Harlow, E. and Lane, D., Antibodies—A Laboratory Manual, Cold Spring Harbor Laboratory Press, Cold Spring Harbor, 1988; Freshney, R. I., "Culture of Animal Cells, A Manual of Basic Technique", 5th ed., John Wiley & Sons, Hoboken, N.J., 2005. Non-limiting information regarding therapeutic agents and human diseases is found in Goodman and Gilman's The Pharmacological Basis of Therapeutics, 11th Ed., McGraw Hill, 2005, Katzung, B. (ed.) Basic and Clinical Pharmacology, McGraw-Hill/Appleton & Lange; 10th ed. (2006) or 11th edition (July 2009). Non-limiting information regarding genes and genetic disorders is found in McKusick, V. A.: Mendelian Inheritance in Man. A Catalog of Human Genes and Genetic Disorders. Baltimore: Johns Hopkins University Press, 1998 (12th edition) or the more recent online database: Online Mendelian Inheritance in Man, OMIM™. McKusick-Nathans Institute of Genetic Medicine, Johns Hopkins University (Baltimore, Md.) and National Center for Biotechnology Information, National Library of Medicine (Bethesda, Md.), as of May 1, 2010, ncbi.nlm.nih.gov/omim/ and in Online Mendelian Inheritance in Animals (OMIA), a database of genes, inherited disorders and traits in animal species (other than human and mouse), at omia.angis.org.au/contact.shtml. All patents, patent applications, and other publications (e.g., scientific articles, books, websites, and databases) mentioned herein are incorporated by reference in their entirety. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

Specific examples of certain aspects of the inventions disclosed herein are set forth below in the Examples.

One skilled in the art readily appreciates that the present invention is well adapted to carry out the objects and obtain the ends and advantages mentioned, as well as those inherent therein. The details of the description and the examples herein are representative of certain embodiments, are exemplary, and are not intended as limitations on the scope of the invention. Modifications therein and other uses will occur to those skilled in the art. These modifications are encompassed within the spirit of the invention. It will be readily apparent to a person skilled in the art that varying substitutions and modifications may be made to the invention disclosed herein without departing from the scope and spirit of the invention.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention provides all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. It is contemplated that all embodiments described herein are applicable to all different aspects of the invention where appropriate. It is also contemplated that any of the embodiments or aspects can be freely combined with one or more other such embodiments or aspects whenever appropriate. Where elements are presented as lists, e.g., in Markush group or similar format, it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. For example, any one or more nucleic acids, polypeptides, cells, species or types of organism, disorders, subjects, or combinations thereof, can be excluded.

Where the claims or description relate to a composition of matter, e.g., a nucleic acid, polypeptide, cell, or non-human transgenic animal, it is to be understood that methods of making or using the composition of matter according to any of the methods disclosed herein, and methods of using the composition of matter for any of the purposes disclosed herein are aspects of the invention, unless otherwise indicated or unless it would be evident to one of ordinary skill in the art that a contradiction or inconsistency would arise. Where the claims or description relate to a method, e.g., it is to be understood that methods of making compositions useful for performing the method, and products produced according to the method, are aspects of the invention, unless otherwise indicated or unless it would be evident to one of ordinary skill in the art that a contradiction or inconsistency would arise.

Where ranges are given herein, the invention includes embodiments in which the endpoints are included, embodiments in which both endpoints are excluded, and embodiments in which one endpoint is included and the other is excluded. It should be assumed that both endpoints are included unless indicated otherwise. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. It is also understood that where a series of numerical values is stated herein, the invention includes embodiments that relate analogously to any intervening value or range defined by any two values in the series, and that the lowest value may be taken as a minimum and the greatest value may be taken as a maximum. Numerical values, as used herein, include values expressed as percentages. For any embodiment of the invention in which a numerical value is prefaced by "about" or "approximately", the invention includes an embodiment in which the exact value is recited. For any embodiment of the invention in which a numerical value is not prefaced by "about" or "approximately", the invention includes an embodiment in which the value is prefaced by "about" or "approximately". "Approximately" or "about" generally includes numbers that fall within a range of 1% or in some embodiments within a range of 5% of a number or in some embodiments within a range of 10% of a number in either direction (greater than or less than the number) unless otherwise stated or otherwise evident from the context (except where such number would impermissibly exceed 100% of a possible value). It should be understood that, unless clearly indicated to the contrary, in any methods claimed herein that include more than one act, the order of the acts of the method is not necessarily limited to the order in which the acts of the method are recited, but the invention includes embodiments in which the order is so limited. It should also be understood that unless otherwise indicated or evident from the context, any product or composition described herein may be considered "isolated".

EXAMPLES

Example 1

Research Goal: To Find Novel Hormones to Cure Diabetes

A protocol to direct the differentiation of human embryonic or induced pluripotent stem cells into functional, insulin expressing beta-cells was developed previously[1]. These Stem Cell-derived beta-cells (SC-beta) can be used to study the development of beta-cells, beta cell function and physiology and they have the potential to treat diabetes by cell transplantation.

Hormones, including insulin, are secreted proteins with potent roles in controlling metabolism, cellular differentiation, and disease. mRNAs encoding secreted or transmembrane proteins transit through the rough endoplasmic reticulum. To identify novel secreted and transmembrane proteins, a technique called Endoplasmic Reticulum Sequencing (ER-seq) has been developed that enriches RNAs of secreted/transmembrane proteins by physically isolating actively translating ribosomes at the surface of the endoplasmic reticulum. To find novel hormones that regulate glucose metabolism, the ER-seq method was applied to SC-beta cells and the associated mRNA sequenced.

Next, differential gene expression and gene ontology analysis were performed to find all known secreted activities in SC-beta cells. In doing so, the technology was validated by identifying, among many other secreted proteins, the INSULIN gene. Eight genes without ascribed function or annotation were analyzed. Since these novel genes are made by SC-beta cells and may code for secreted proteins, it was reasoned that, like insulin, some of these novel genes might have a metabolic role.

These eight genes were transiently expressed from plasmid DNA at high levels in the liver of mice by hydrodynamic tail vein (HTV) injection of plasmid DNA[2]. To assess if any of these eight genes affected glucose homoeostasis, three days after injection, at the time of high expression from liver, a glucose tolerance test was performed.

One of the eight human genes injected, C1ORF127, cleared glucose from the blood circulation faster than controls (FIG. 1A). The reduction in glucose levels is significant and reproducible: to date, and was successfully tested C1ORF127 glucose lowering activity in over fifty mice. Additionally, it was found that C1ORF127 is able to reduce blood glucose levels in diet-induced obese mice, a model for Type2 diabetes.

Figure 1B:
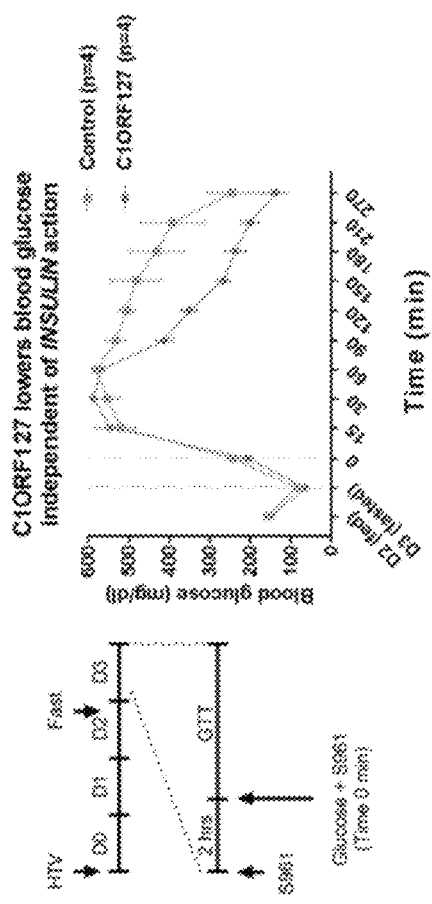

Since C1ORF127 is expressed in INSULIN producing beta-cells, it was asked if its glucose lowering activity was dependent on insulin action. To test this point, a potent and specific peptide inhibitor, and antagonist of the insulin receptor, S961[3] was used. When S961 is administered acutely to mice they quickly become hyperglycemic demonstrating the efficacy of S961 at inhibiting the insulin receptor and preventing glucose uptake into muscle and fat, thereby resulting in a net accumulation of glucose in the circulation. HTV injections of C1ORF127 and control DNA and on day three performed a glucose tolerance test. For this experiment, S961 was added at two timepoints; first, two hours before the injection of glucose; and second, with the glucose bolus at the beginning of the test. As seen in FIG. 1B, C1ORF127 can clear glucose from the circulation faster than controls. This data strongly suggests that C1ORF127 removes glucose from the circulation independent of insulin action. Notably, in these experiments, C1ORF127 lowers blood glucose levels without causing hypoglycemia, a problem with all known drugs that work to promote INSULIN secretion (Time 0 min in FIG. 1A and D3 fasted in FIG. 1B).

The C1ORF127 gene is predicted to code for a protein of 684 amino acids (MW 73 kDa). It is a highly conserved transcript among vertebrates that lacks canonical signals for secretion or membrane insertion. Its expression has been confirmed in SC-beta cells and cadaveric human Islets by immunofluorescence microscopy. Using internal expression databases, C1ORF127 was found to be expressed primarily in beta-cells and at lower levels in somatostatin-expressing (pancreatic delta) cells. In humans, C1ORF127 is also expressed in muscle and cerebellum. Its mouse orthologue, Gm572, is expressed exclusively in beta- and delta- (somatostatin) expressing cells. By Western blot, the protein is found to be expressed at the predicted molecular weight in SC-beta and cadaveric human islets. Moreover, the Type 2 Diabetes knowledge portal (a curated disease risk repository) was search and identified mutations in C1ORF127 that might be critical for the development or progression of Type 2 diabetes[4].

REFERENCES

1. Pagliuca F W and Millman J R, et. al., Generation of functional human pancreatic β cells in vitro. Cell. 2014 Oct. 9; 159(2):428-39
2. Chen C A, et. al., In vivo screening for secreted proteins that modulate glucose handling identifies interleukin-6 family members as potent hypoglycemic agents. PLoS One. 2012; 7(9): e44600.
3. Schaffer L, et. al., A novel high-affinity peptide antagonist to the insulin receptor. Biochem Biophys Res Commun. 2008 Nov. 14; 376(2):380-3.
4. Type 2 Diabetes Knowledge Portal. 2018 Sep. 10 www.type2diabetesgenetics.org/home/portalHome Example 2

The biogenesis of hormones is directed by endoplasmic reticulum (ER)-localized ribosomes actively translating their mRNAs at the translocon complex (Mandon et al., 2013; Ogg et al., 1995; Rapoport et al., 2007). Most studies identifying novel secreted factors and hormones have relied on algorithms that predict canonical topogenic signals (Diehn et al., 2000; Emanuelsson et al., 2007; Kall et al., 2004; Meinken et al., 2015, Petersen et al., 2011). Although informative, these computational predictions do not efficiently account for a significant fraction of genes that are part of this functional class (Jan et al., 2014). Recent efforts to characterize the complement of mRNAs of secreted factors relied on the biochemical isolation of ER-localized ribosomes (Jan et al., 2014; Fazl et al., 2019; Reid et al., 2014). However, these efforts have been limited to yeast and cancer cells in vitro (Jan et al., 2014; Fazl et al., 2019; Reid et al., 2014). Here is described a protocol called ER-seq for the biochemical isolation of ribosome/translocon complexes in human pluripotent stem cells (hPSCs) and differentiated progeny. This protocol was applied to SC-β cells and identified a previously uncharacterized gene, C1ORF127, that promotes glucose clearance independent of insulin action.

Development of a Biochemical Fractionation Method for the Isolation of Ribosome-Translocon Complexes As the biogenesis of secreted factors and hormones occurs in ER-localized ribosome/translocon complexes, it was reasoned that the isolation of translocon-associated mRNAs will effectively enrich for mRNAs of secreted factors and may serve as a proxy for their expression in a cell (Jan et al., 2014). To isolate translocon complexes, hPSC cell lines were generated that express a subunit of the translocon complex, Sec61β, fused to GFP either constitutively or in insulin-expressing β cells (FIG. 2A). To achieve ubiquitous and constitutive expression in hPCSs and differentiated progeny, TALEN-mediated genome editing technology was used to knock-in the GFP-SEC61β fusion protein into the AAVS1 locus under the control of a ubiquitously-expressed artificially-engineered CAAGS promoter (CAAGS::GFP-SEC61β; FIG. 2B). Similarly, to express this transgene in insulin-expressing β cells, CRISPR was used to knock-in the GFP-SEC61β fusion transgene into the last exon of the endogenous insulin gene (INS::GFP-SEC61β; FIG. 2C). In hPSCs and SC-β cells, the expression of the transgene was perinuclear as expected for an ER-localized protein (FIGS. 2B-2C).

Figure 3A:
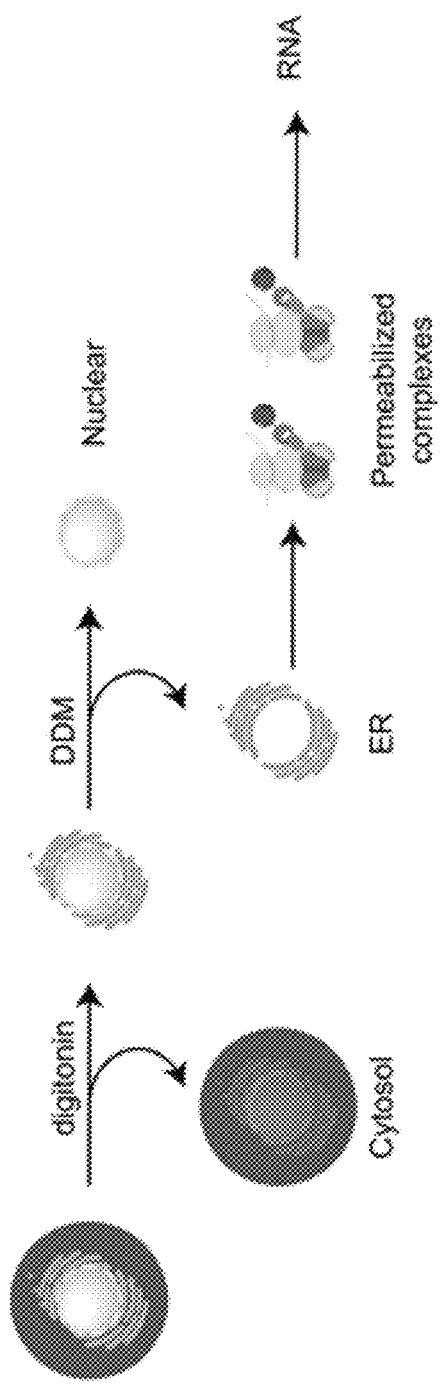
Figure 3C:
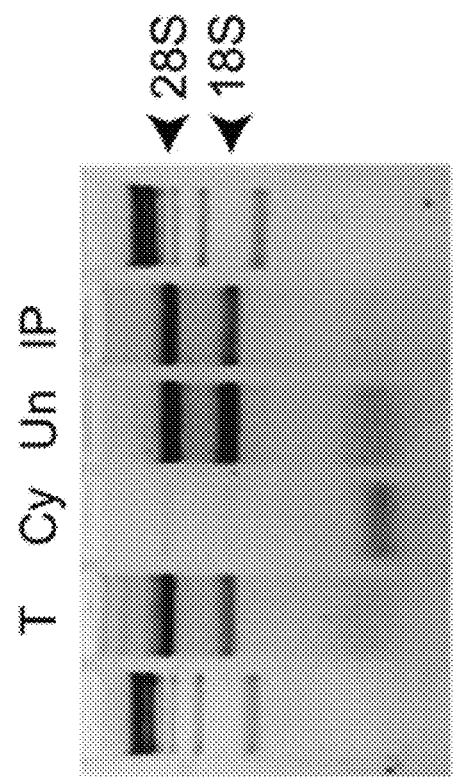
Figure 3B:
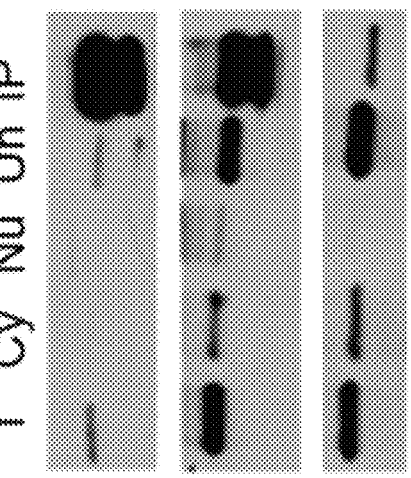

Protocols that rely on the differential solubility of cellular membranes to permeabilize the plasma and ER membranes in a step-wise manner were developed (FIG. 4.2A). First, digitonin was used to permeabilize the plasma membrane and retrieve the cytoplasmic fraction. To the insoluble fraction, n-Dodecyl-B-D-Maltoside (DDM) was added in a hypotonic buffer to permeabilize the ER membrane and luminal components which was called the ER fraction (Nichitta et al. 2014). After ER permeabilization, the ER fraction was subjected to immunoprecipitation with anti-GFP magnetic beads to purify ribosome/translocon complexes and associated mRNAs (FIG. 3A). This protocol was applied to self-renewing hPCSs and detected a significant enrichment in Sec61β and GFP protein expression in the immunopurified (IP) fraction relative to unfractionated cell extracts as assayed by western blot (FIG. 3B). Importantly, the ribosomal protein subunit L13a and ribosomal RNA subunits 28S and 18S were also co-purified (FIGS. 3B-C). The immunopurified ER fraction was subjected to mass spectrometry and detected peptides of the translocon subunit SEC61a, translocon-associated protein disulfide isomerase (PDI) and multiple ribosomal protein subunits (FIG. 3D). In all, the biochemical protocol allows for a robust and effective enrichment of ribosome/translocon complexes.

ER-Seq Robustly Enriches for mRNAs of Secreted Factors in hPSCs and SC-β Cells.

Figure 4A:
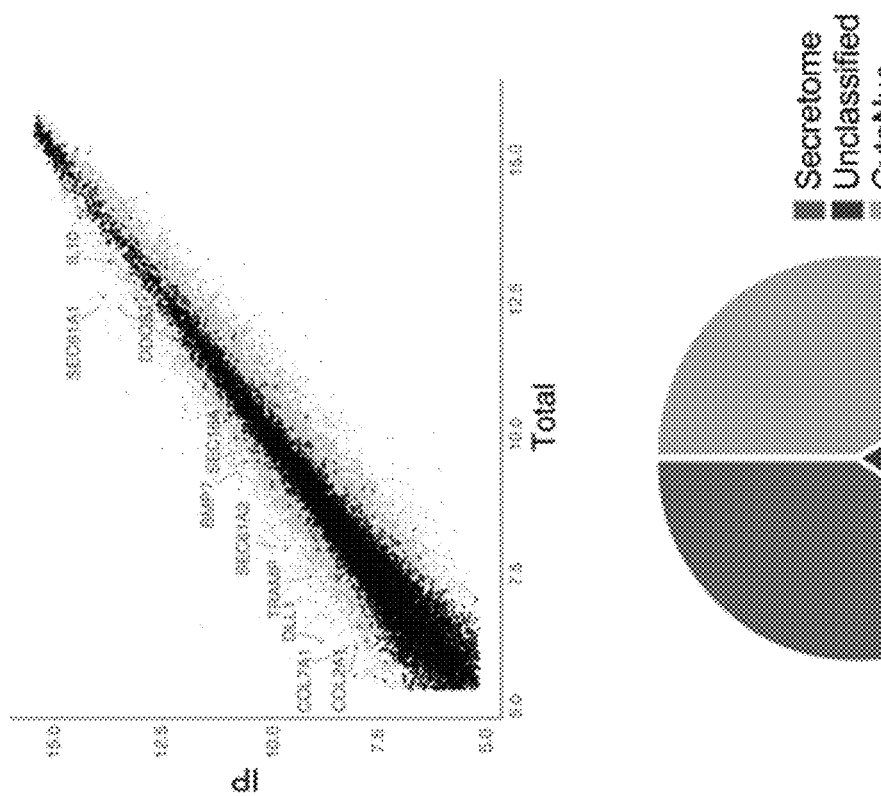
FIGS. 4A-4C show selective enrichment of mRNAs encoding for factors involved in ER-related processes in self renewing Human Embryonic stem cells.
Figure 4B:
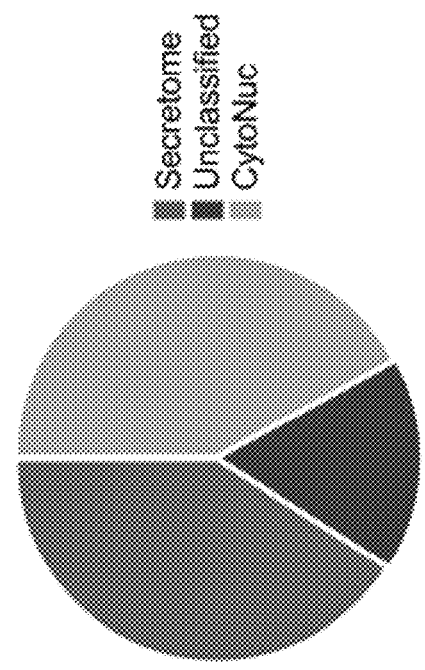
Figure 4C:
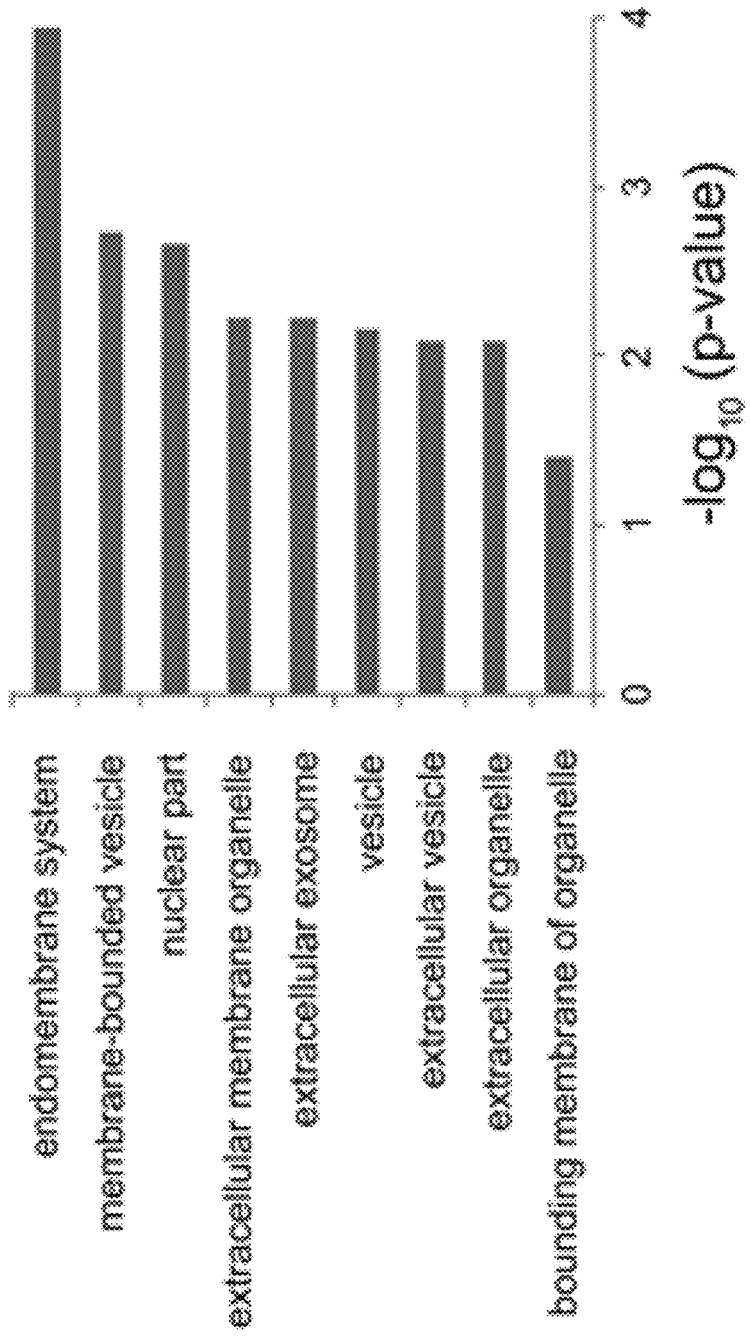

To determine whether this approach effectively enriches for mRNAs that code for secreted factors and membrane proteins, microarray analysis on translocon-associated mRNAs purified from hPSCs was performed. Compared to mRNAs collected from total unfractionated cell extracts, an enrichment of mRNAs encoding for the ER factors Sec61α and DDOST as well as secreted factors such as BMP7, DLL1, COL2A1, COL7A1, among others, was detected (FIG. 4A). Out of 3174 genes that are enriched in the IP fraction relative to total mRNA, 989 genes (31.1%) were detected that are predicted to be secreted factors or membrane proteins based on canonical topogenic signal peptide prediction (FIG. 4B). Based on gene ontology analysis of genes enriched in the IP fraction, there is a significant enrichment of genes that are part of the endomembrane system, vesicles and extracellular components in the IP fraction (FIG. 4C). 650 genes were also detected that are enriched in the IP fraction that are unannotated and have no predicted localization signal. As around 10% of all genes expressed in most cell types are predicted to be secreted (Uhlén et al., 2015), computational analysis suggests this approach effectively enriches for mRNAs of secreted factors expressed in hPSCs.

Figure 5E:
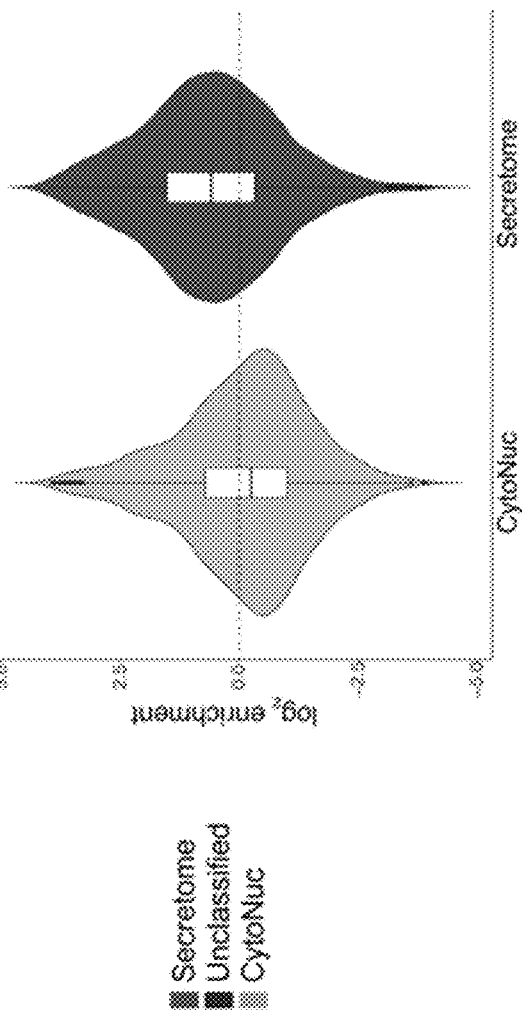
Figure 5D:
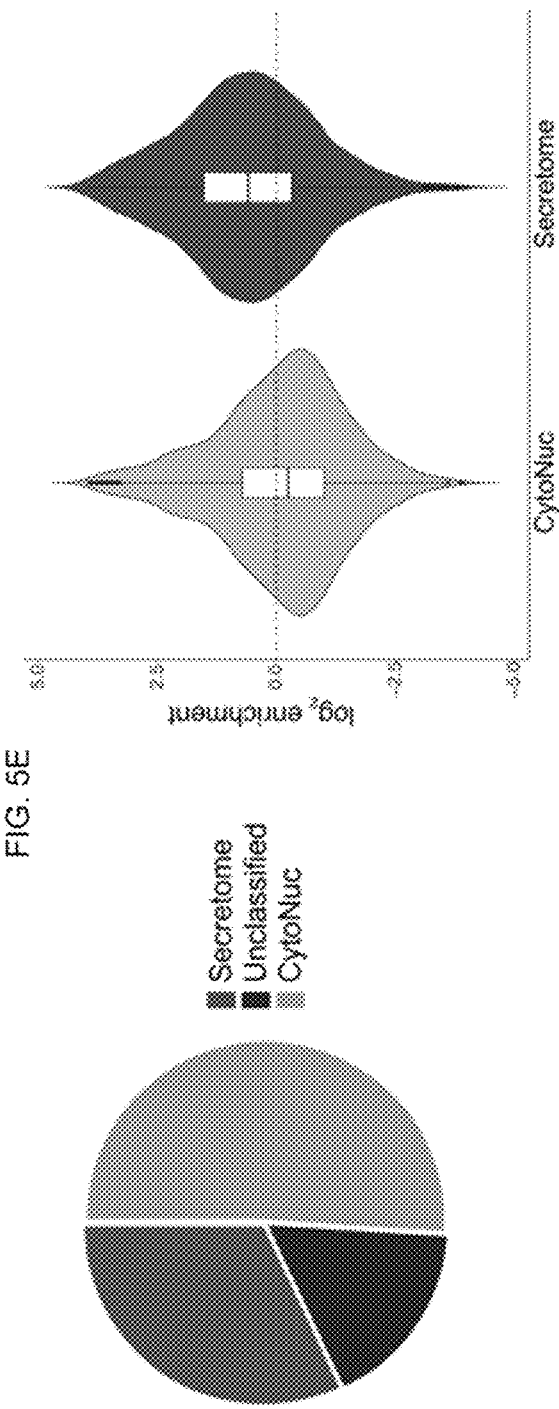
Figure 5F:
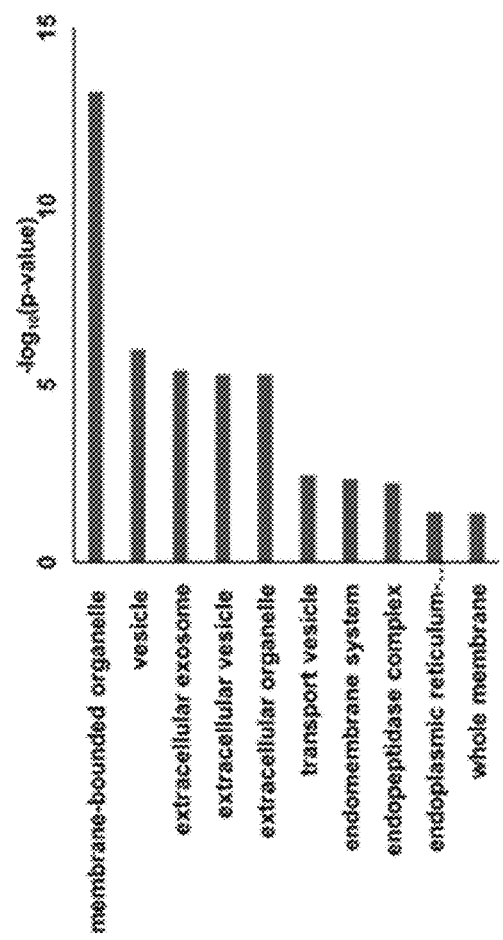

The efficacy of the ER-seq protocol at enriching for mRNAs coding for secreted factors in highly secretory β cells was next determined. To this end, an in vitro directed differentiation protocol (Pagliuca et al., 2014) to generate SC-β cells from hPSCs using the INS::GFP-SEC61β cell line (FIG. 5A-B) was used. This allowed for isolation of ribosome/translocon complexes from β cells in a heterogeneous mixture of cell types and RNA-sequencing on translocon-associated mRNAs. The protocol was applied to SC-β cells and, by RNA-sequencing of translocon-associated mRNAs, identified a significant enrichment of hormones such as insulin and amylin (IAPP), angiogenic factors VEGFA and VGF, as well as other genes involved in insulin secretion such as chromogranin A (CHGA), secretogranins (SCG2, SCG3, SCG5), and synapthophysin (SYP) (FIG. 5C). 2,732 genes were identified that are enriched in the IP fraction relative to total unfractionated RNA (fold change >2). 874 of this set of genes (32%) are predicted to be secreted factors or membrane proteins based on computational topogenic signal prediction (Kall et al., 2005) (FIG. 5D). 17% of the IP-enriched genes did not have a predicted subcellular localization pattern and were not annotated as nuclear, cytoplasmic, secreted or membrane-localized. Among factors predicted to be part of the secretome of the cell, a robust enrichment of their mRNAs in the IP fraction relative to total RNA (FIG. 5E) was detected. Genes that are annotated as nuclear and/or cytoplasmic were depleted in the IP fraction (FIG. 5E). Accordingly, gene ontology analysis of IP-enriched genes suggests an enrichment in factors that are part of the endomembrane system, ER and extracellular part of the cells (FIG. 5F). Overall, computational analysis suggests an effective enrichment and quantification of mRNAs of secreted factors by ER-seq.

Stage-Specific Expression Patterns of Translocon-Associated mRNAs

Figure 6A:
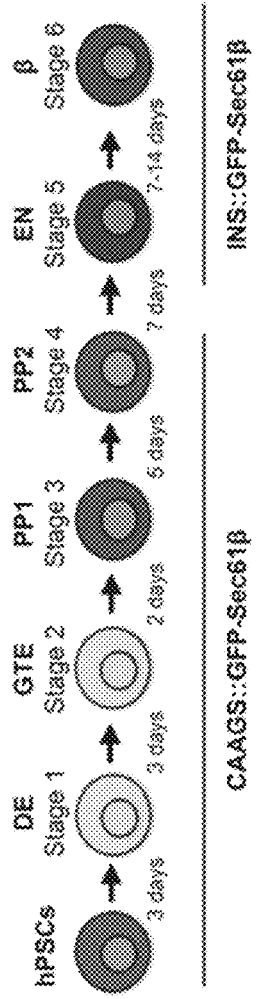
FIGS. 6A-6G shows stage-specific expression patterns of translocon-associated mRNAs.
Figure 6B:
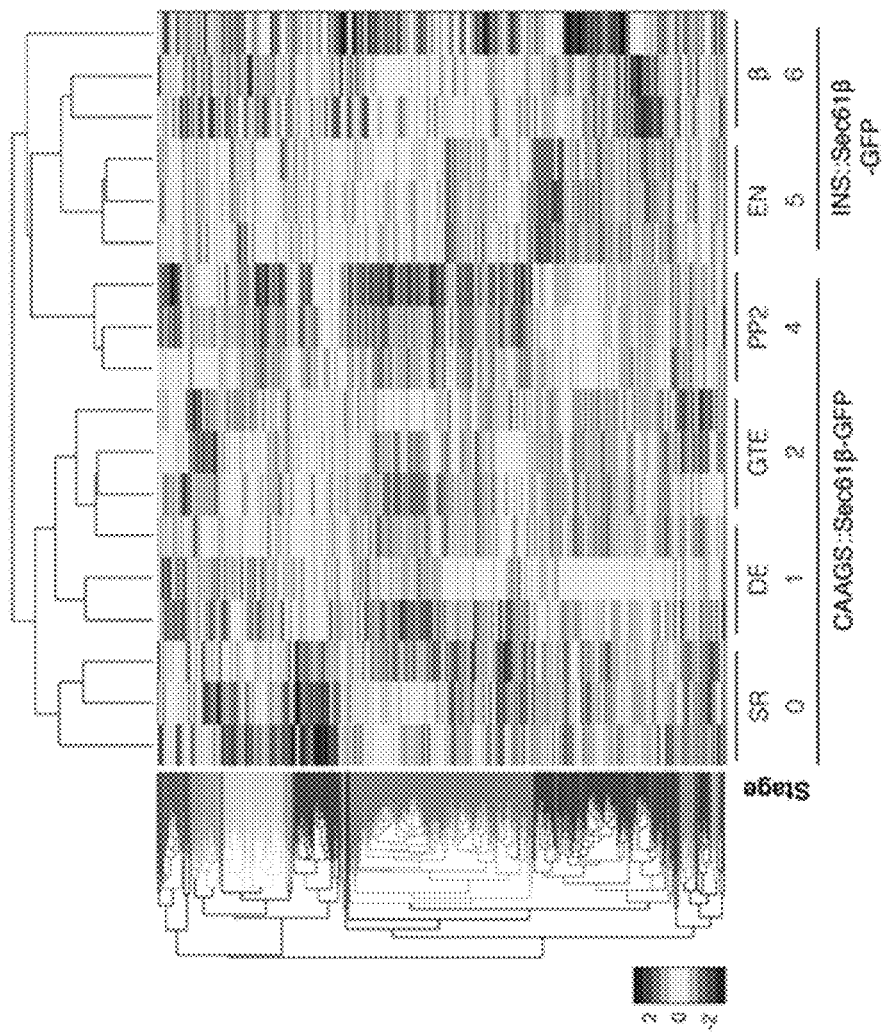
Figure 6C:
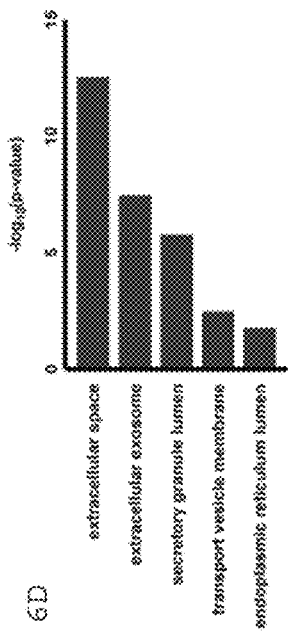
Figure 6D:
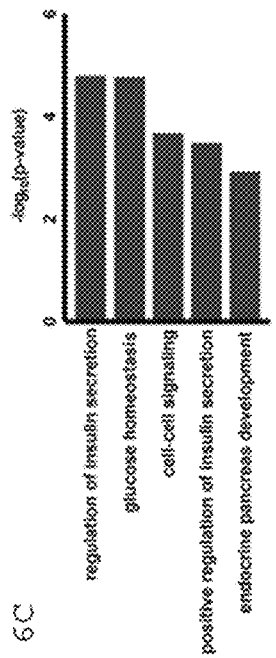
Figure 6E:
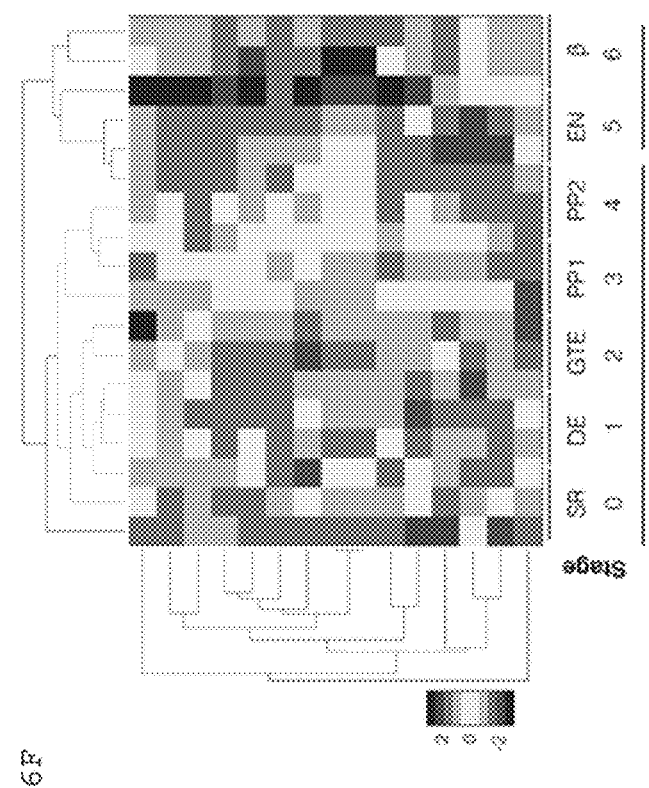
Figure 6F:
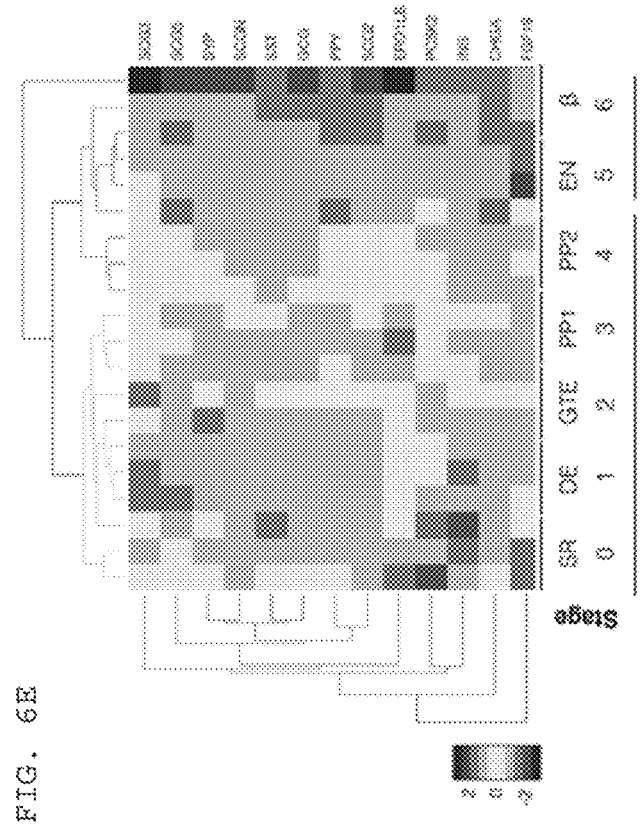
Figure 6G:
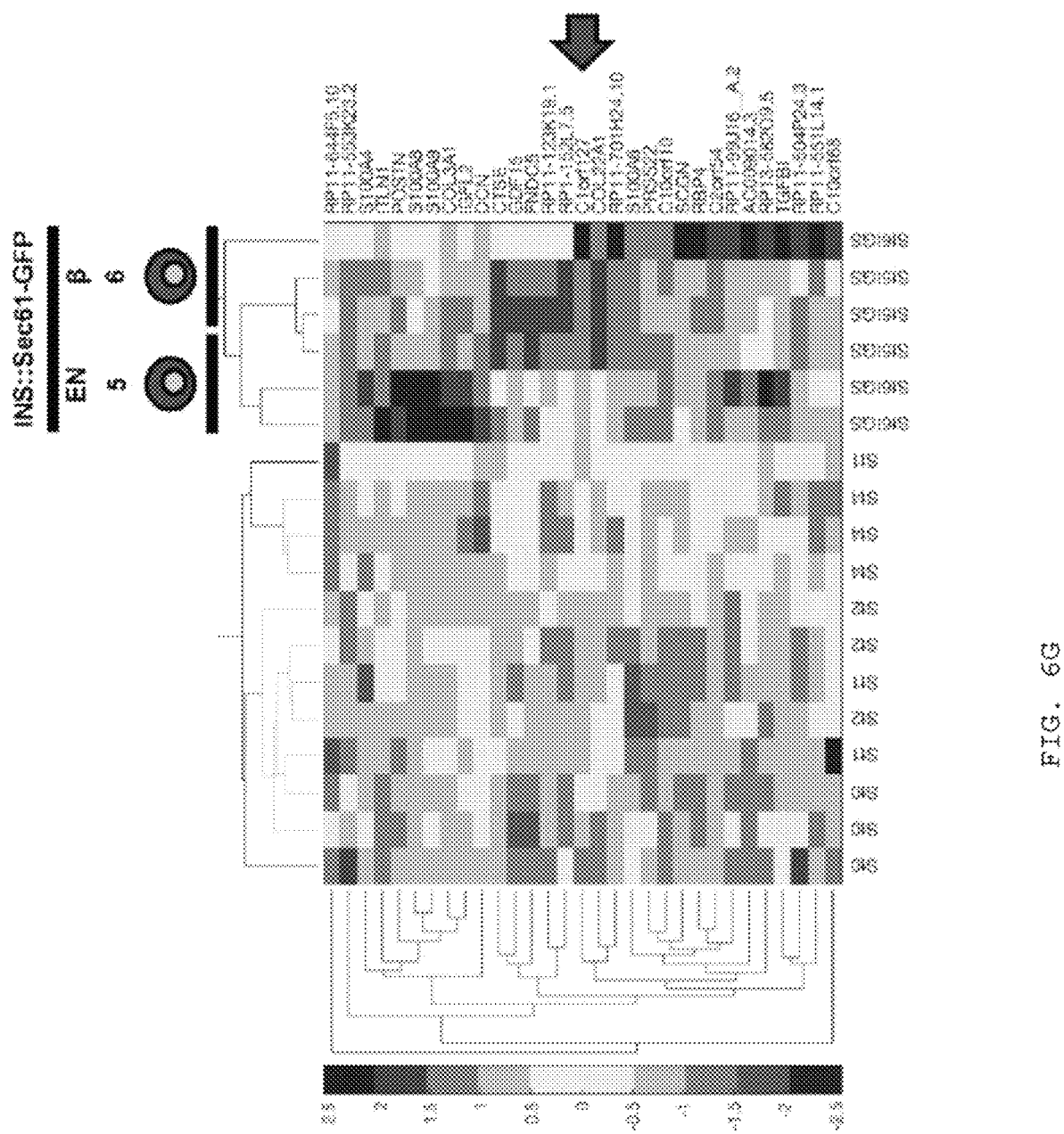
Figure 7C:
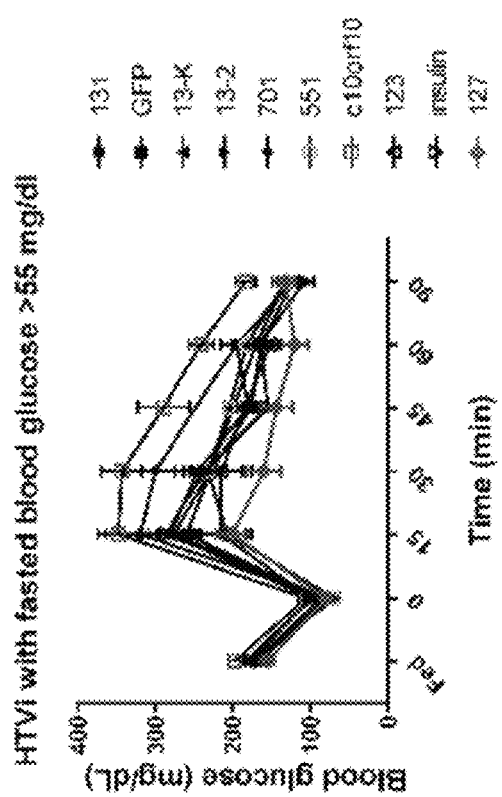
Figure 7D:
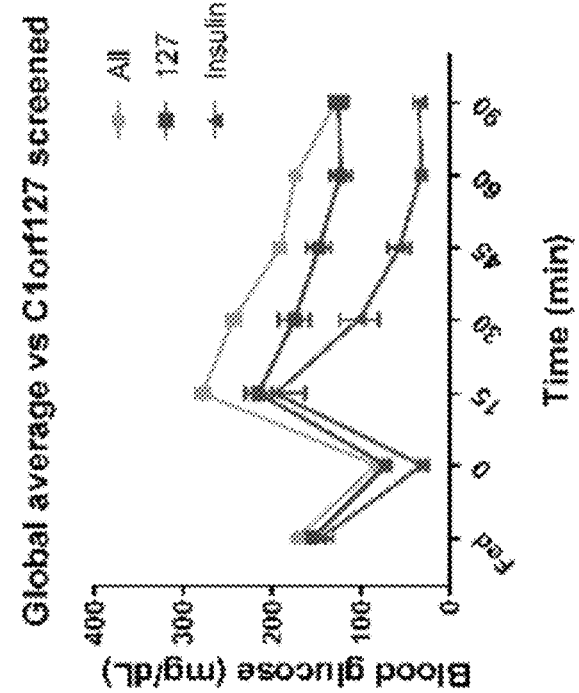
Figure 8A:
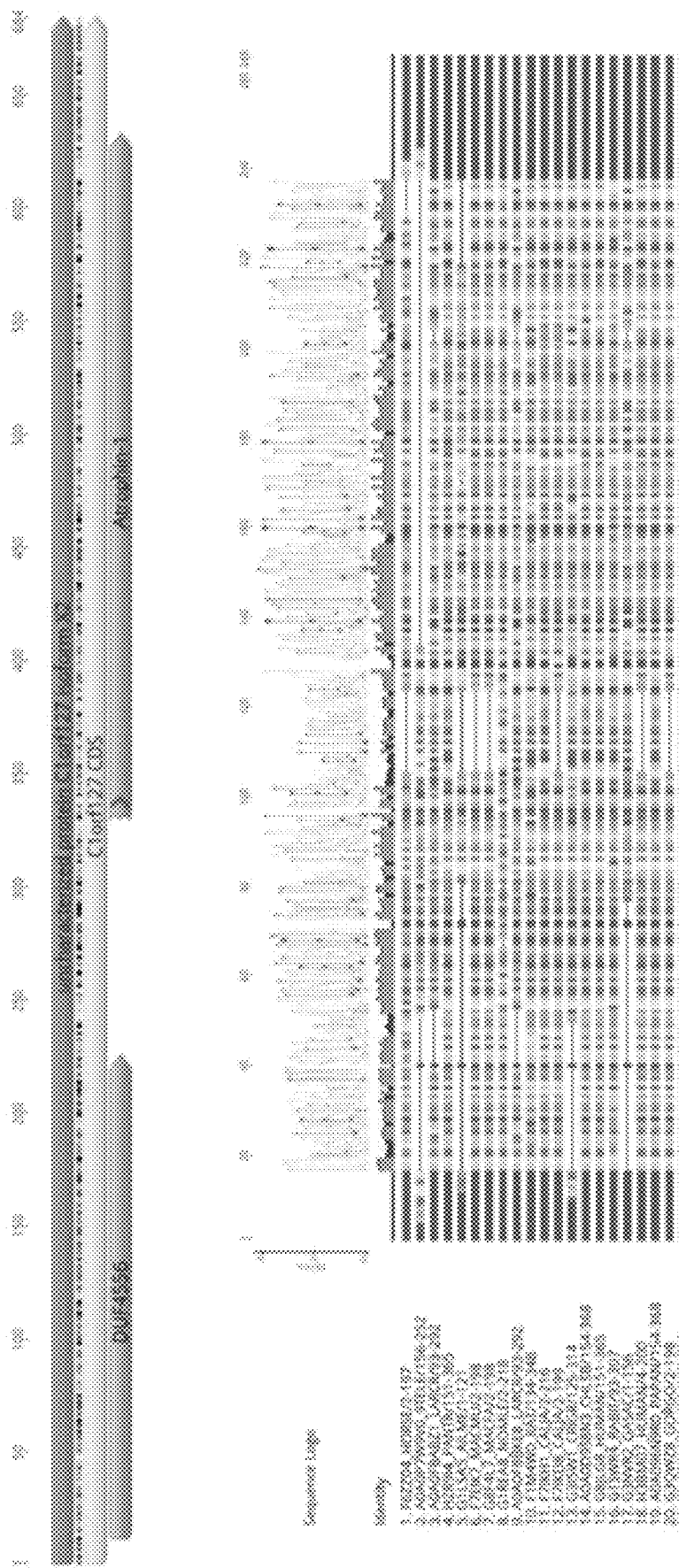
FIGS. 8A-8B show C1ORF127 is well conserved among vertebrates.
Figure 8A:
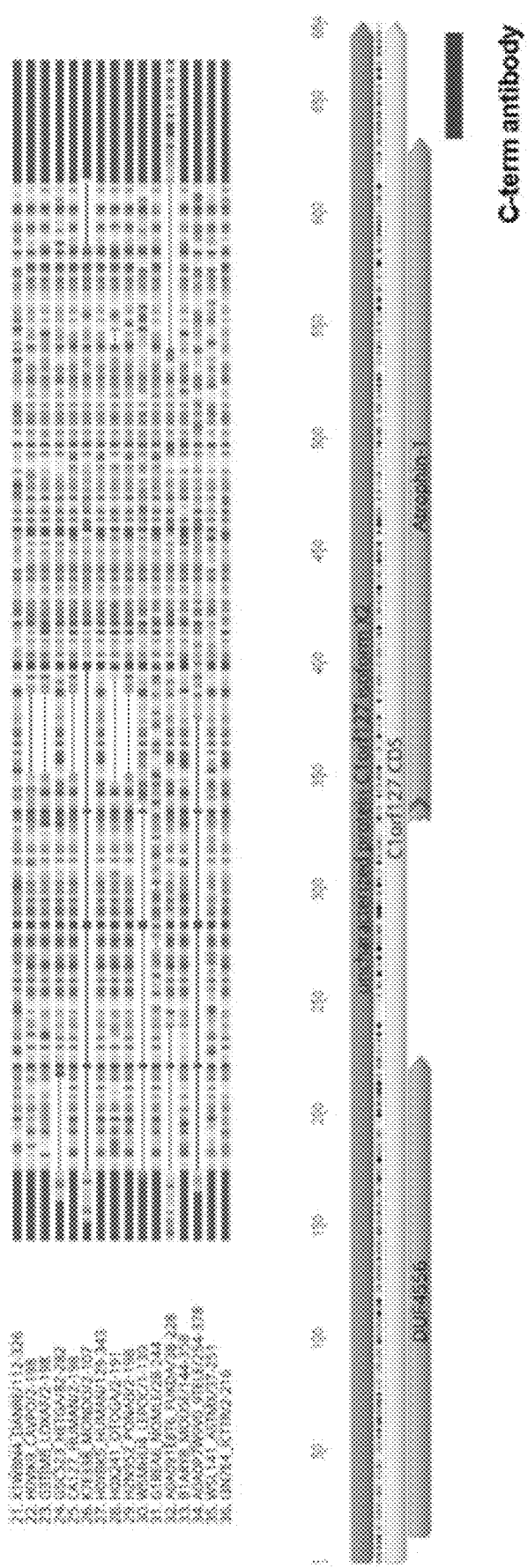
Figure 8B:
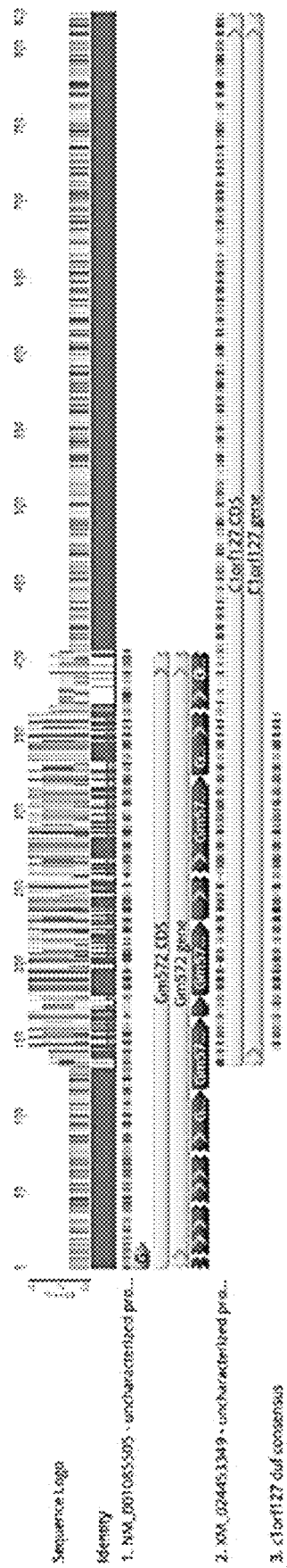
Figure 9A:
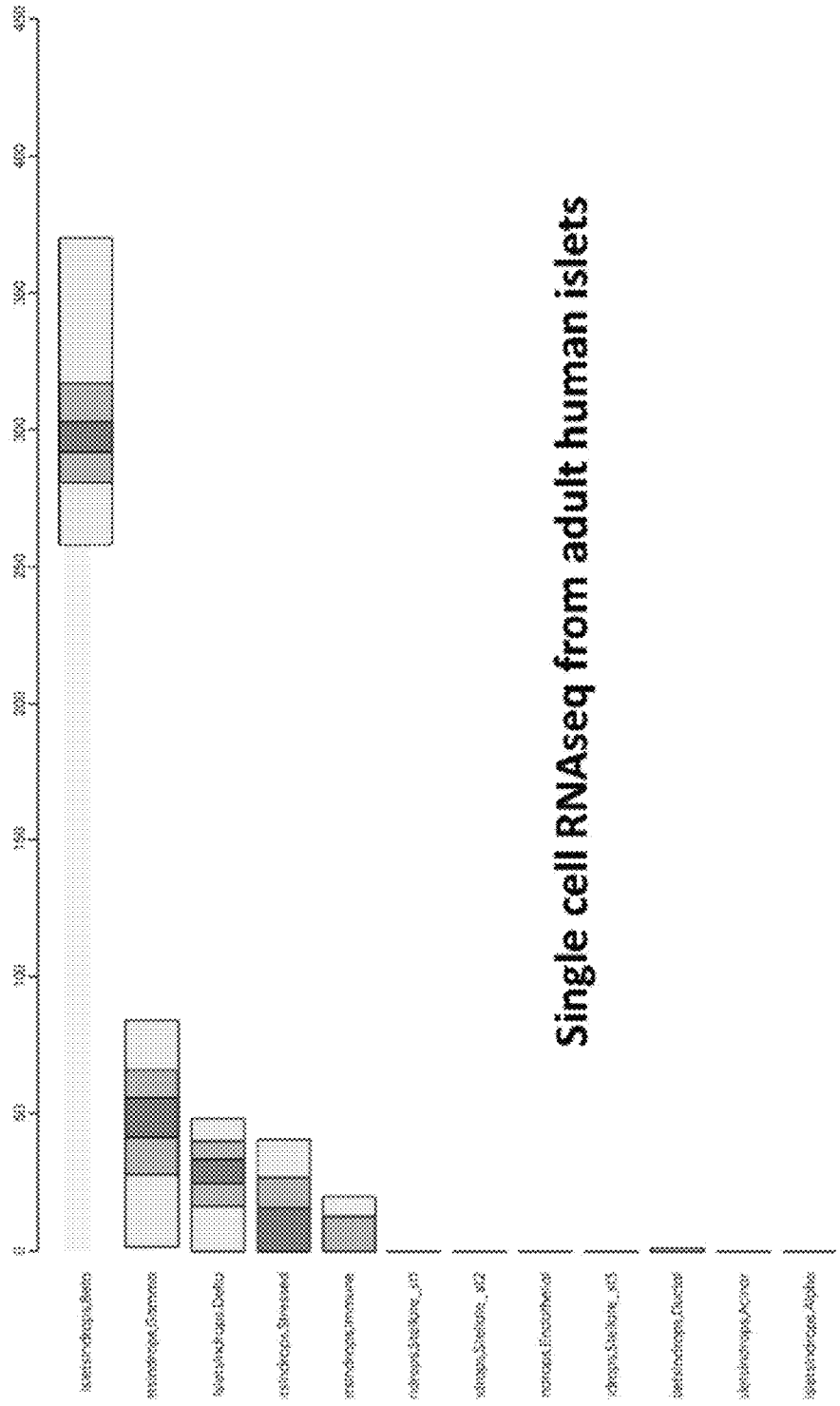
FIG. 9A-9B show C1ORF127 gene expression.
Figure 9B:
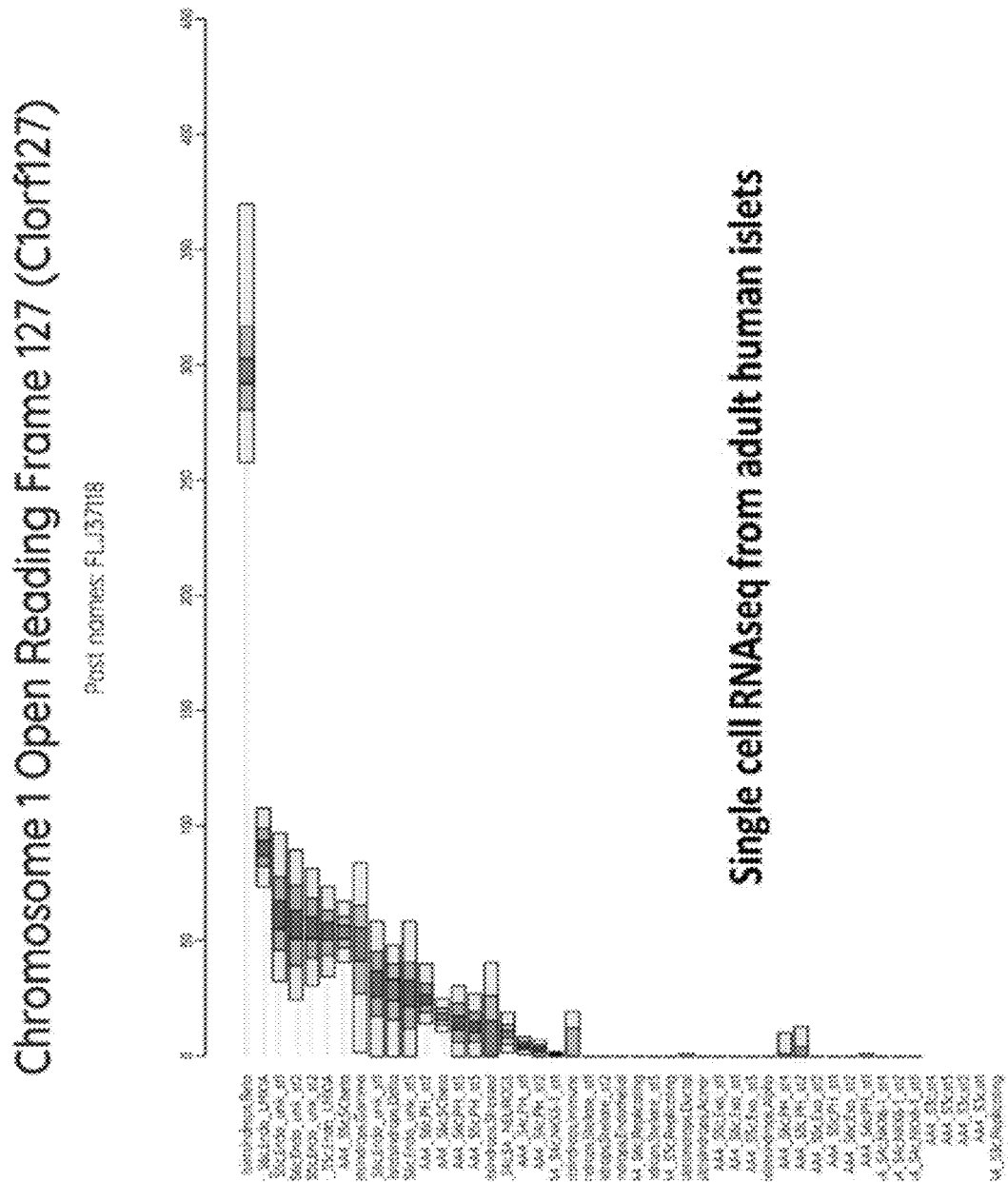
Figure 10A:
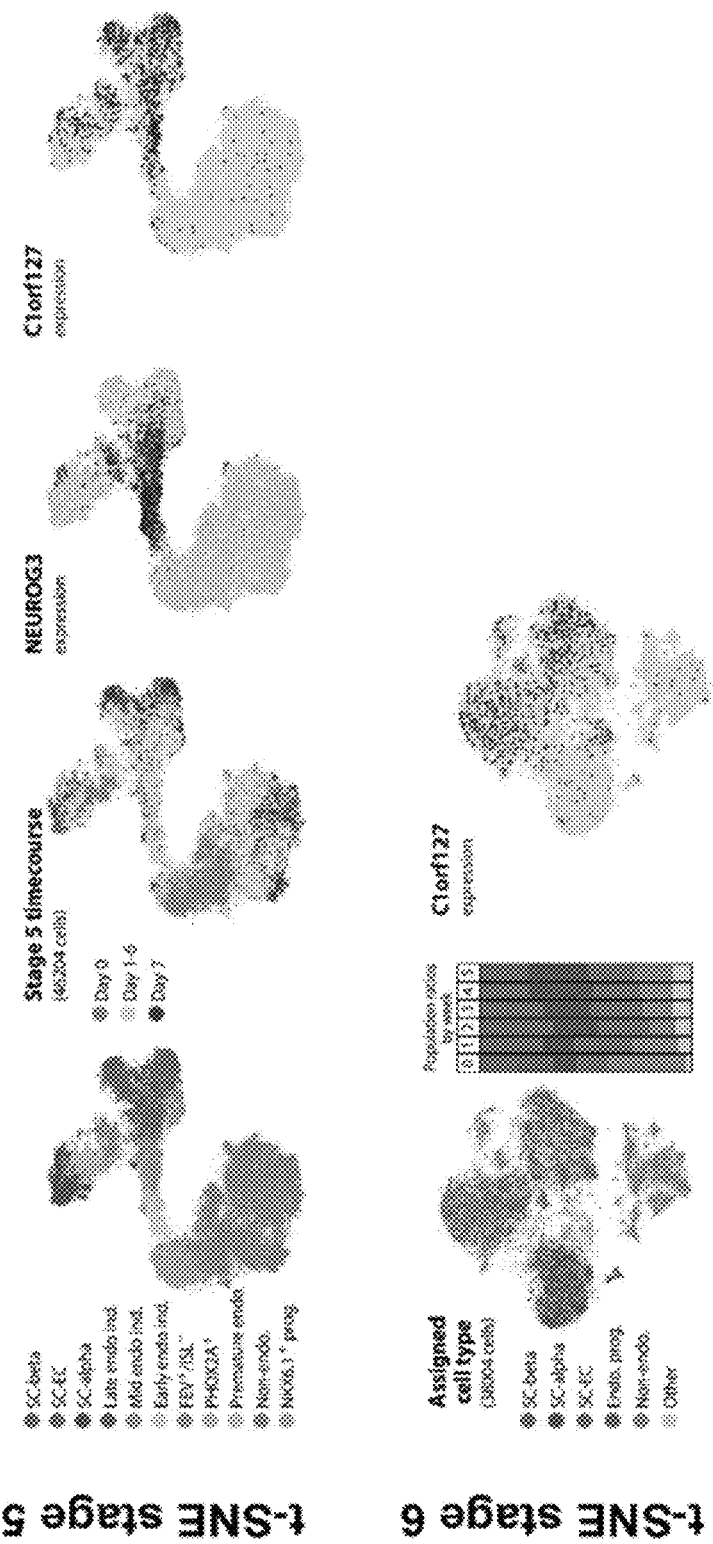
FIGS. 10A-10B show C1ORF127 gene expression.
Figure 10B:
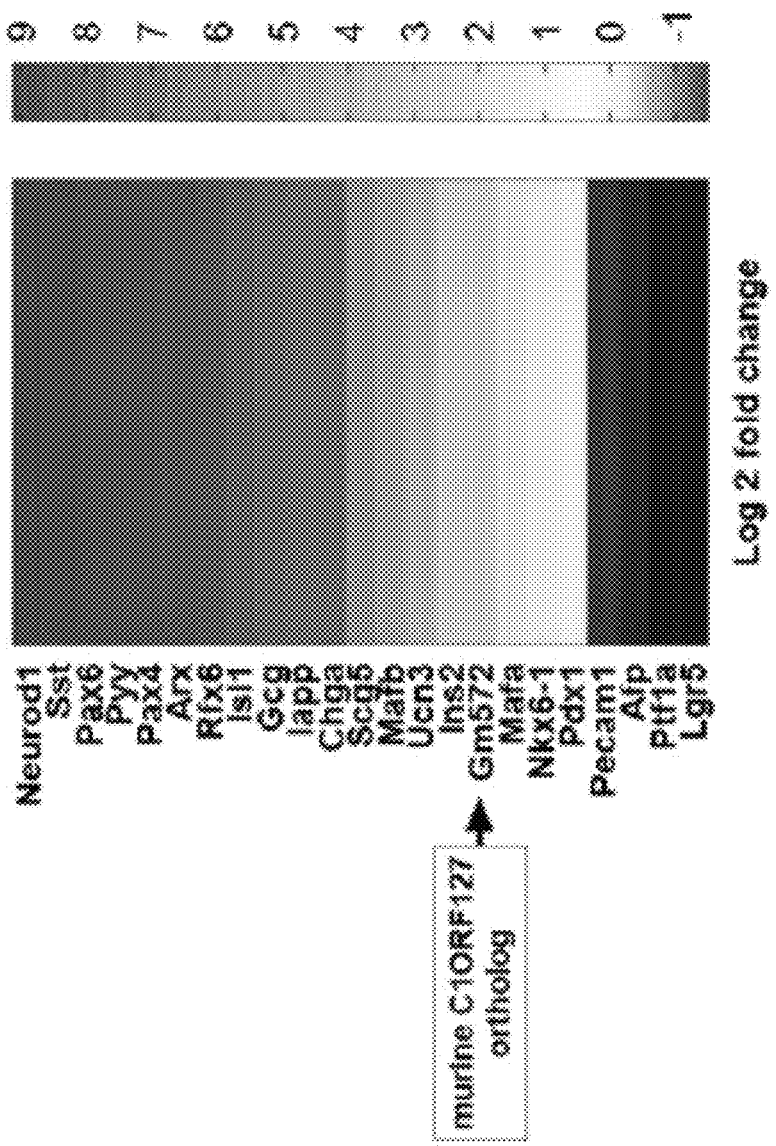
Figure 11:
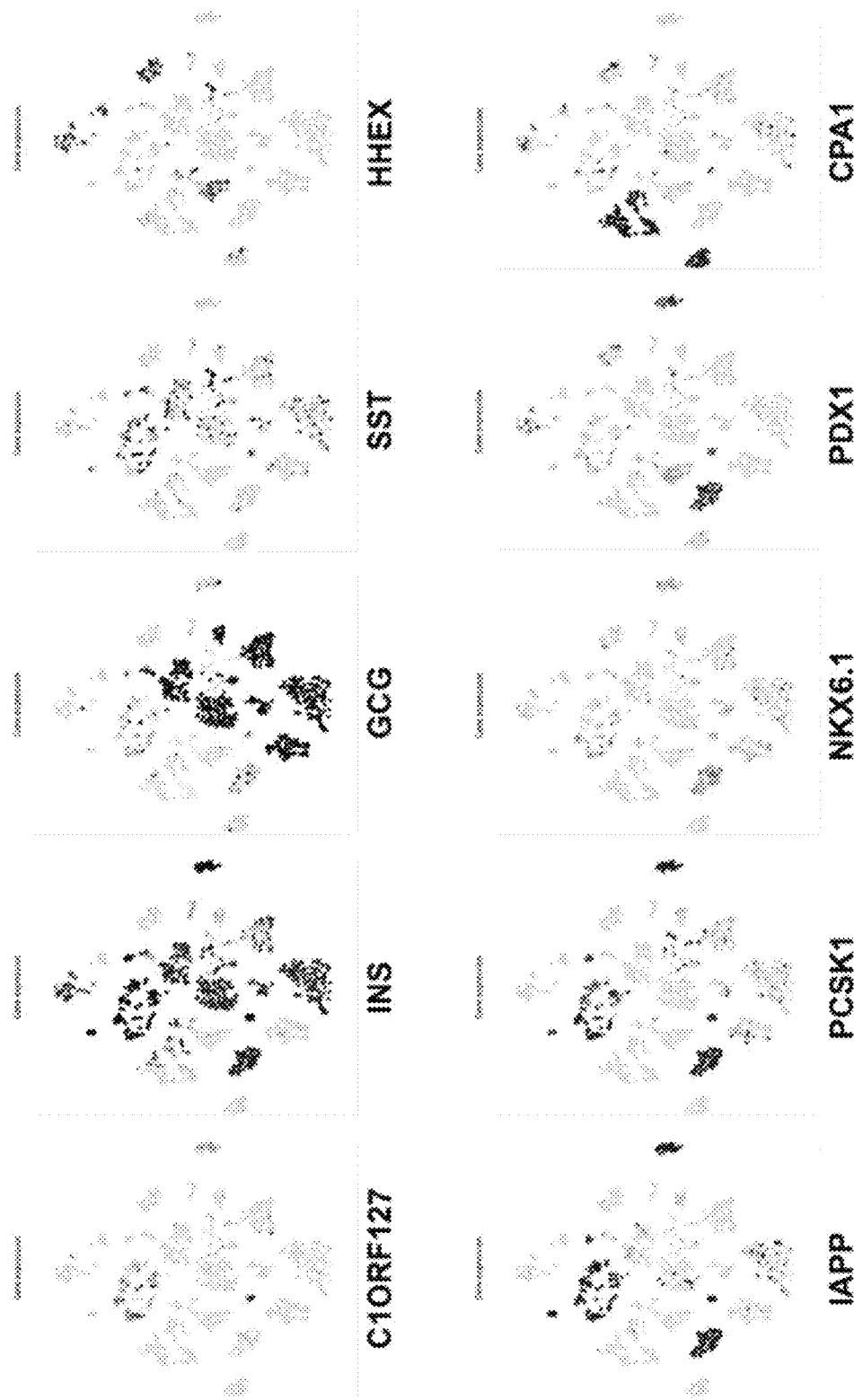
FIG. 11 shows C1ORF127 gene expression. Analysis of published single cell RNA seq data from human cadaveric islets demonstrates that C1ORF127 is predominantly expressed by beta-cells but it is also expressed by somatostatin-expressing cells. t-SNE plots.
Figure 13A:
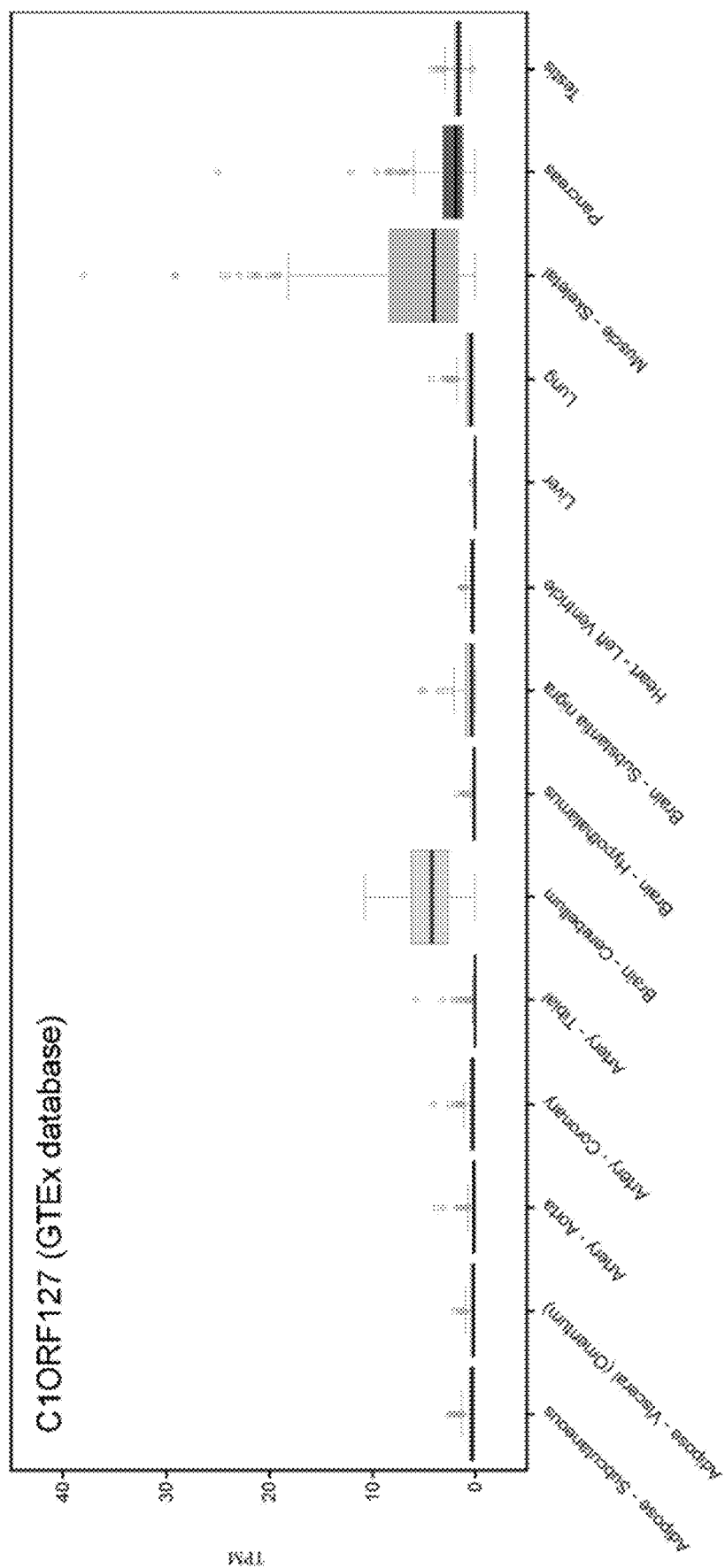
FIGS. 13A-13B show other human tissues expressing C1ORF127.
Figure 13B:
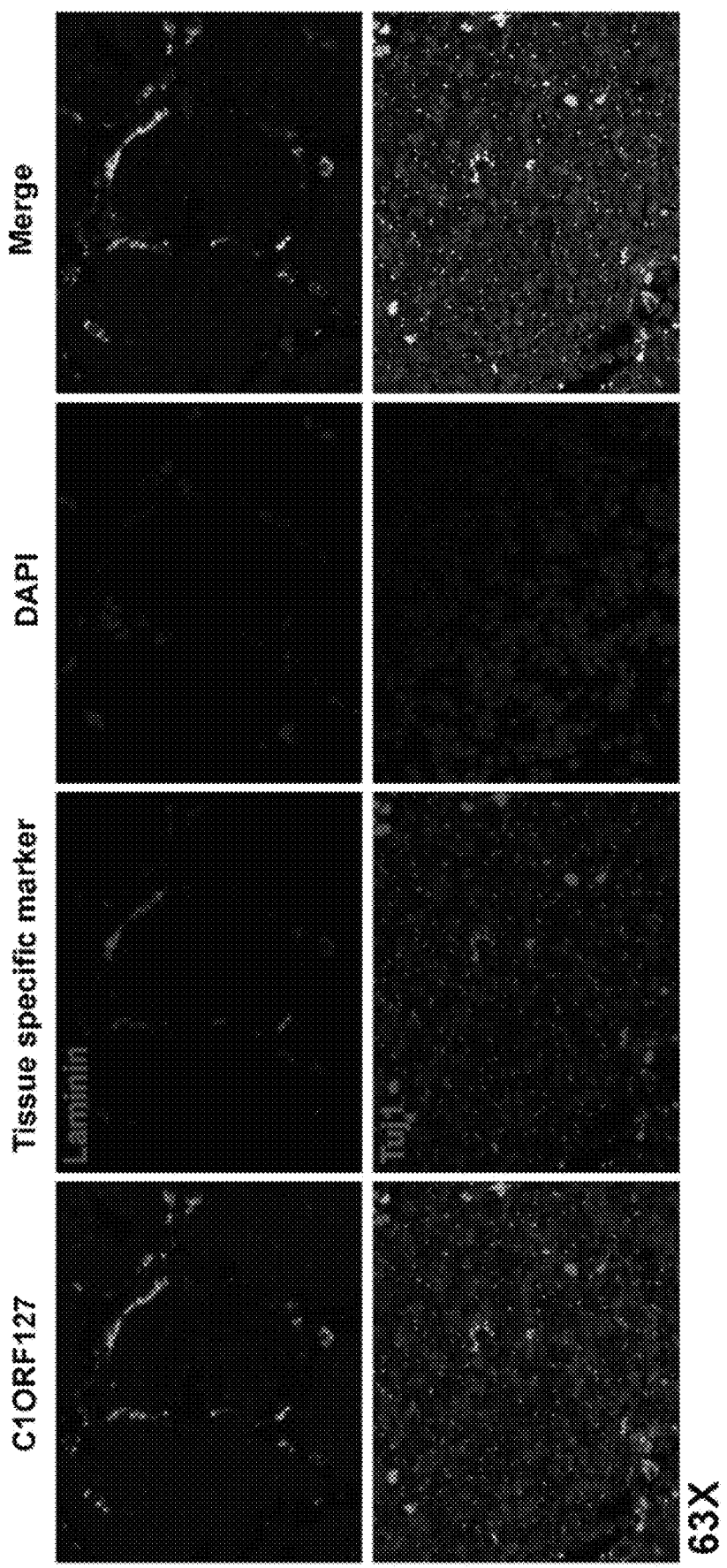
Figure 14:
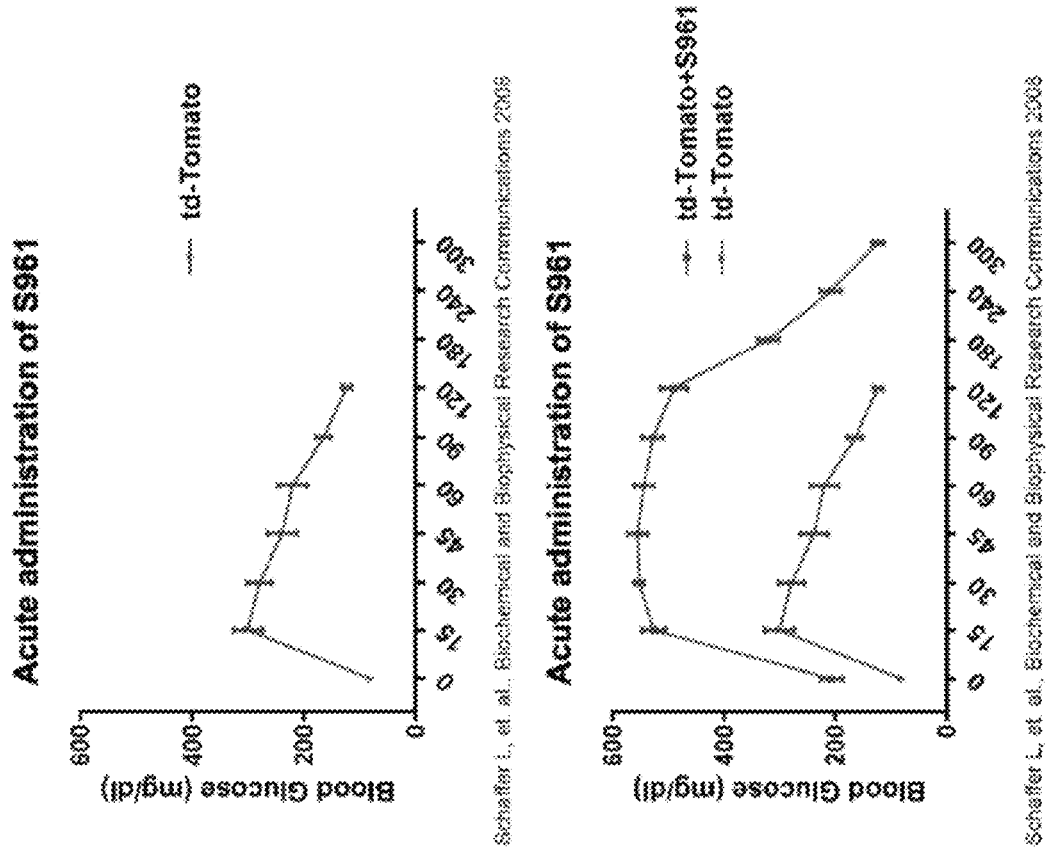
FIG. 14 shows S961 model validation. Acute administration of the insulin receptor antagonist S961 is sufficient to render mice hyperglycemic. Adapted from Schaffer L., et al., Biochemical and Biophysical Research Communications, 2008.
Figure 15:
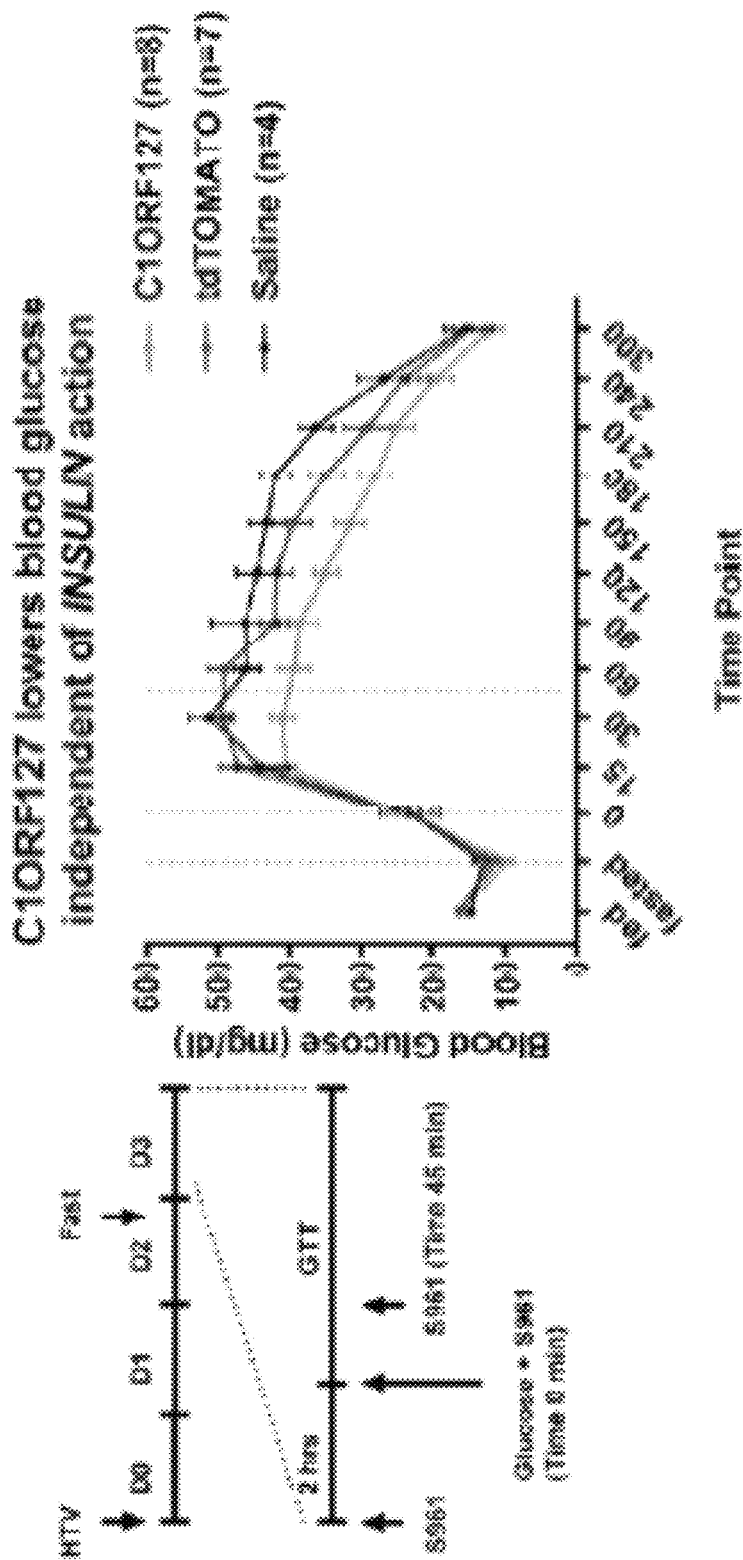
FIG. 15 shows C1ORF127 lowers blood glucose independent of insulin action. S961 injected 2 hours before, with glucose, and 45 minutes after glucose injection.. C1ORF127 cleared blood glucose even in the presence of S961. 1.5 mg/dl glucose bolus.
Figure 16:
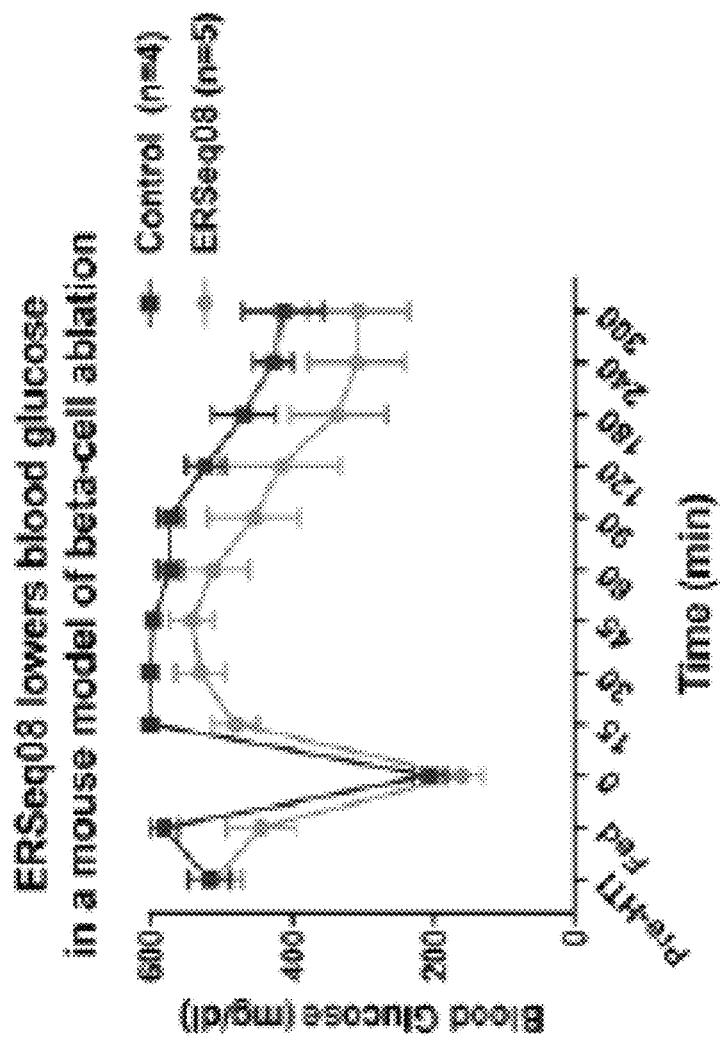
FIG. 16 shows C1ORF127 improves glucose clearance independent of insulin action as shown by the effect of ER-seq08 in Streptozotocin (STZ) induced diabetes model. Mice were rendered diabetic by the administration of STZ (Notice hyperglycemia pre-Hydrodynamic tail vein injection, HTI). Diabetic mice overexpressing C1ORF127 had a marked reduction in blood glucose levels compared to control.
Figure 17:
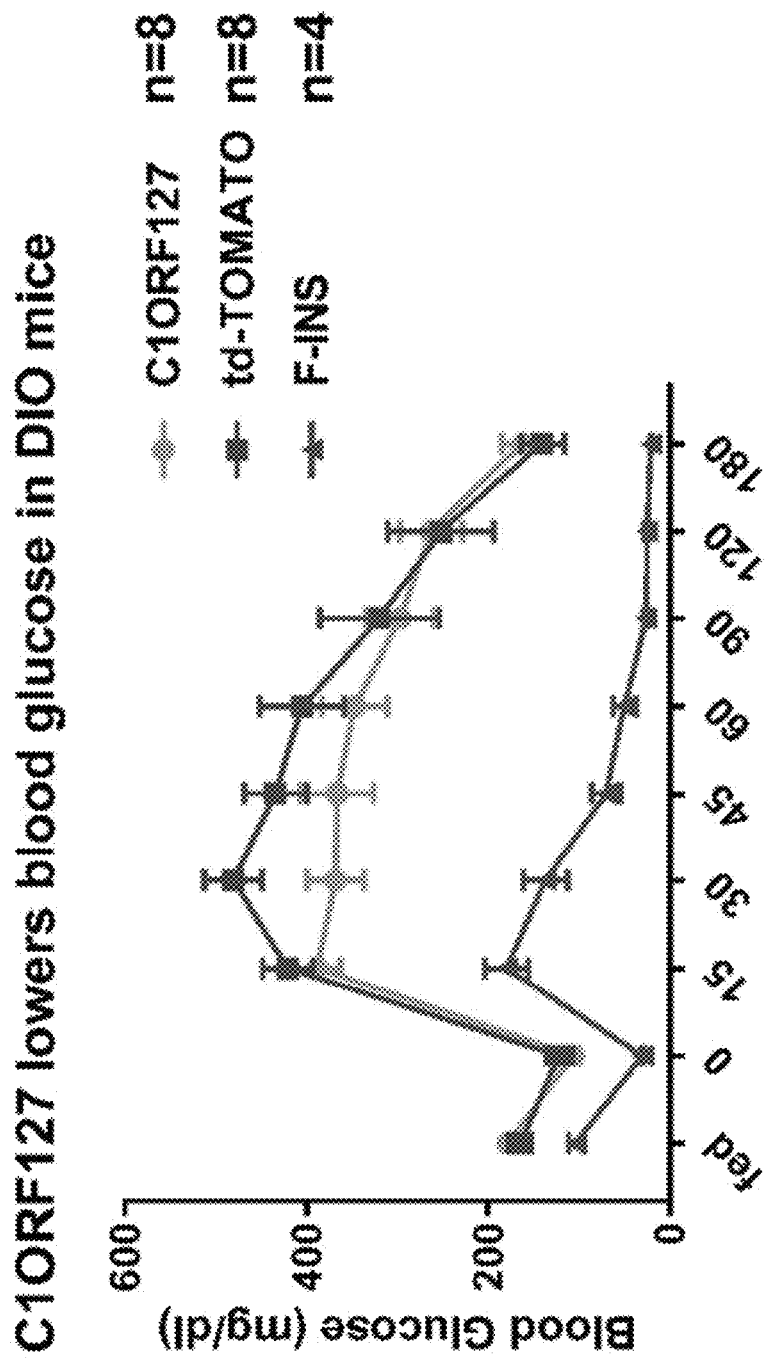
FIG. 17 shows C1ORF127 can lower blood glucose in a high-fat diet obesity model of Type 2 diabetes. DIO—Diet-induced Obesity mice. F-INS—DIO Mice transfected with F-INS—insulin having a Furin cleavage site. Insulin excreted by the liver.
Figure 18A:
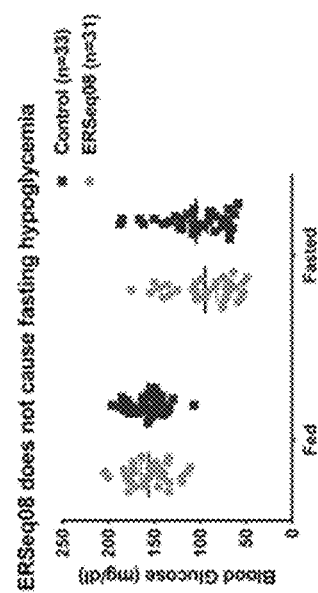
FIGS. 18A-18C show ER-seq08 improves glucose clearance and does not cause hypoglycemia.
Figure 18B:
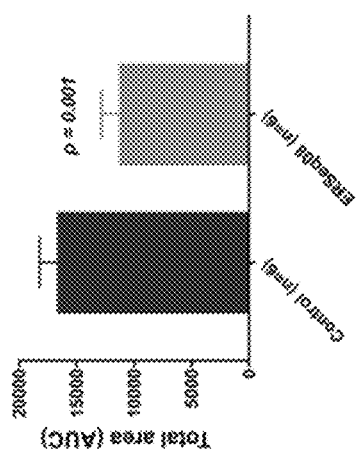
Figure 18C:
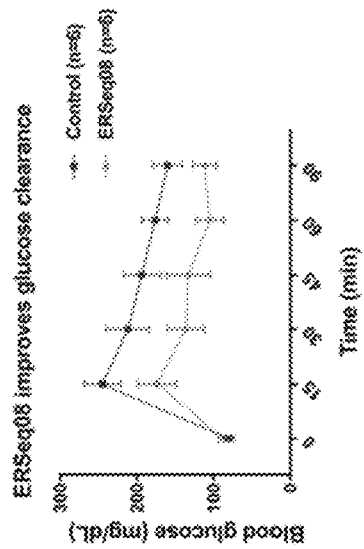
Figure 19A:
FIGS. 19A-19B show C1ORF127 has primary structure characteristics of a peptide hormone.
Figure 19B:
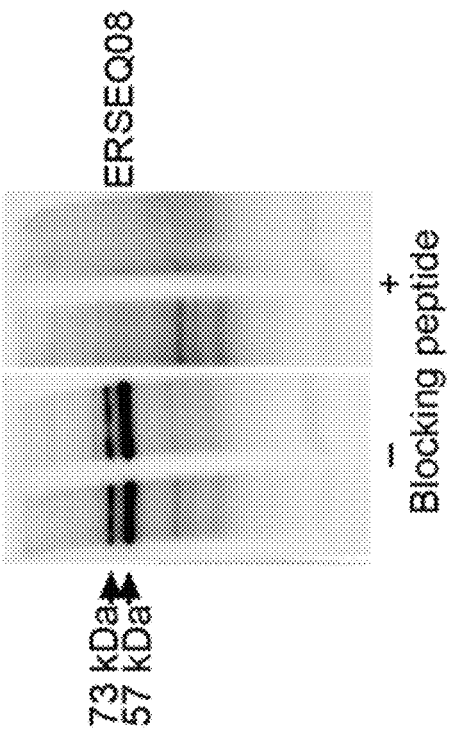
Figure 20:
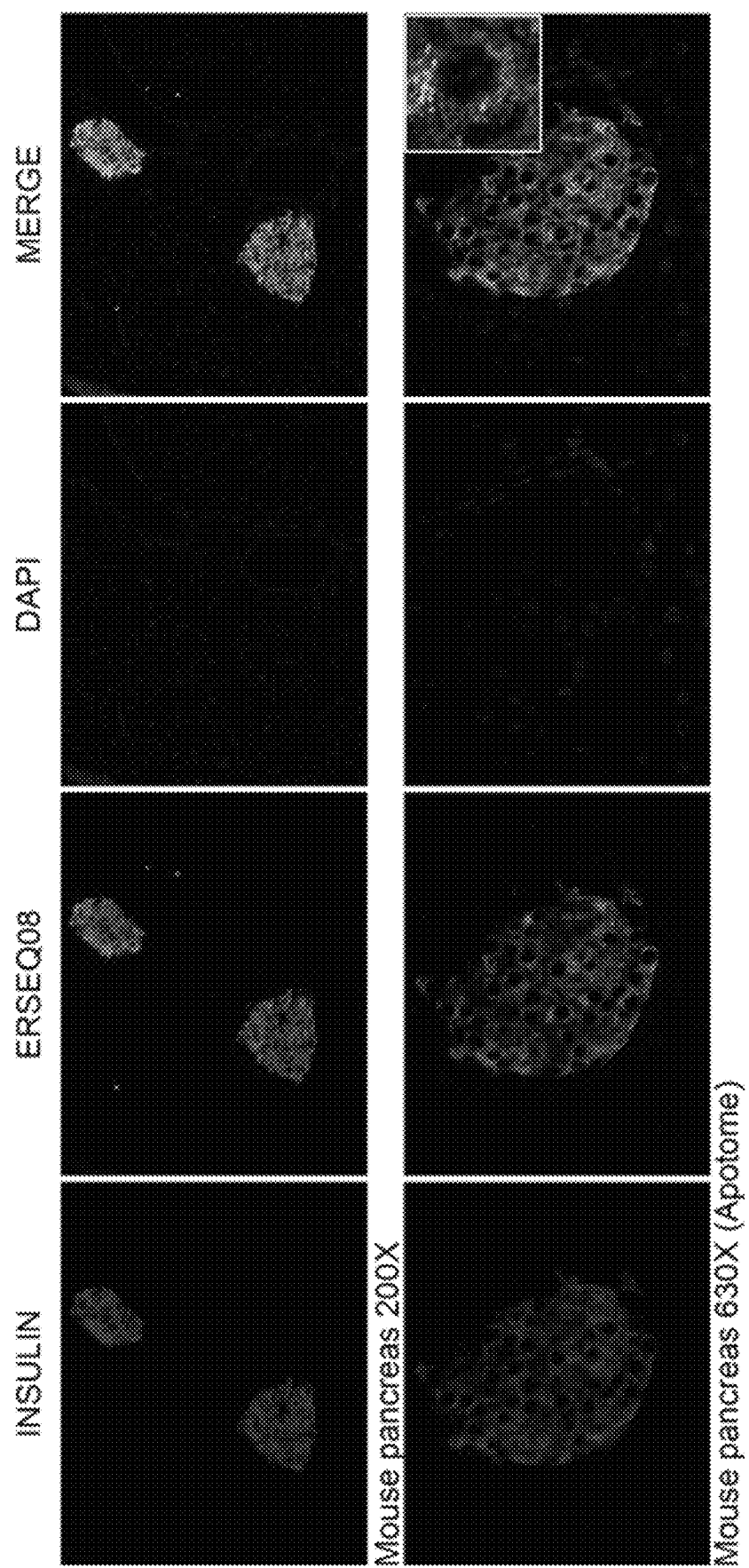
FIG. 20 shows immunofluorescence staining of adult mouse sections with INSULIN or C1ORF127 antibodies. To our surprise C1ORF127 seems to be expressed by vesicles not expressing INSULIN. Note the lack of overlap in the 630X inset. At this point we cannot rule out that C1ORF127 may also be expressed in some Insulin containing vesicles. This suggests that the secretion of C1ORF127 from beta-cells could be modulated independently from that of INSULIN and could lead to the discovery of a new class of drugs that exclusively promote C1ORF127 secretion.
Figure 21:
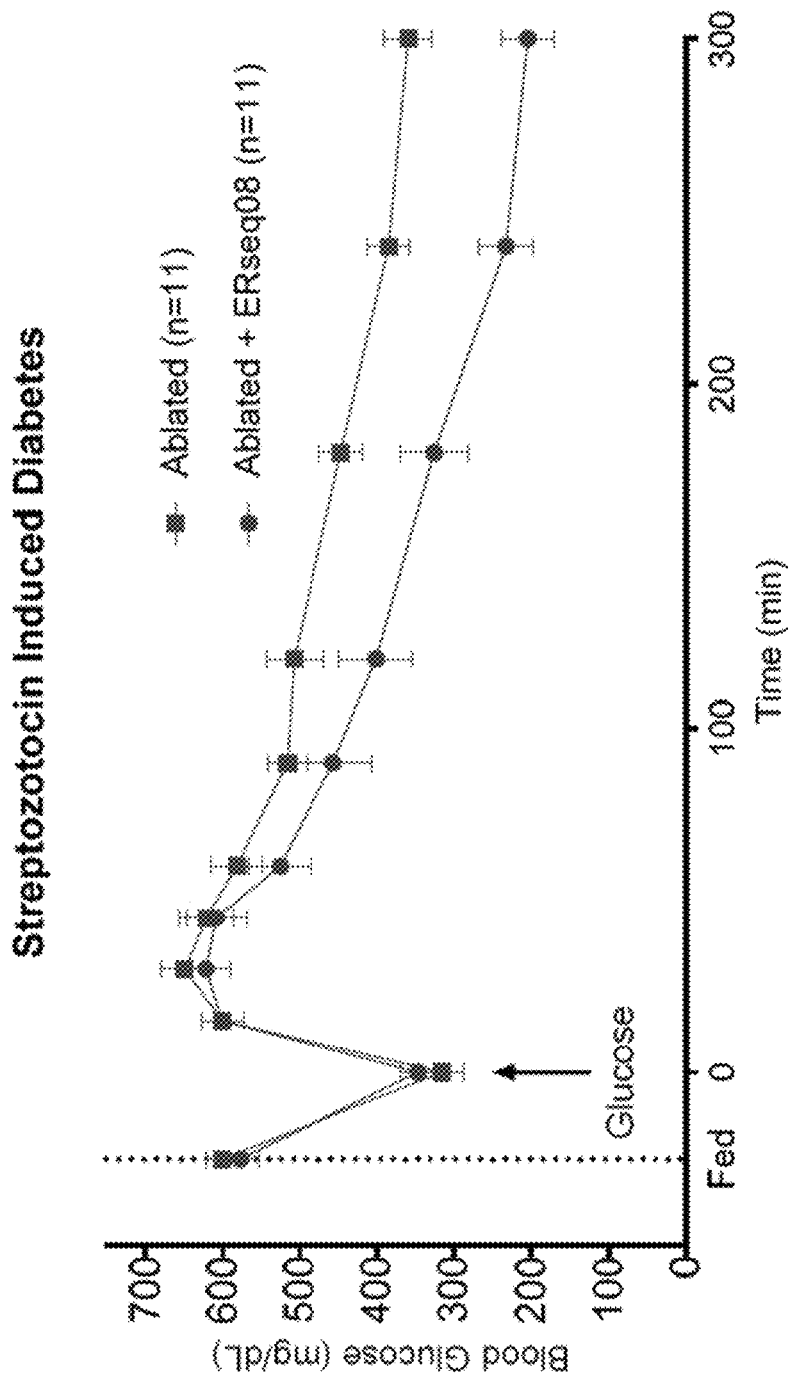
FIG. 21 shows C1ORF127 (i.e., ERseq08) is a potent modulator of glucose homeostasis in beta-cell ablated mice. Streptozotocin (STZ) induced diabetes is a common mouse model of Type 1 diabetes. All animals are diabetic when fed ad libitum (Fed). After O/N fasting the blood glucose levels drop. This is followed by an injection of glucose. C1ORF127 is able to clear glucose from the circulation faster than control animals (injected with a red fluorescent protein). Surprisingly, the effect of C1ORF127 brings animals into the normoglycemic range. These results suggest that C1ORF127 is working independent of insulin action. The results also suggests C1ORF127 has glucagon-like activity.
Figure 22:
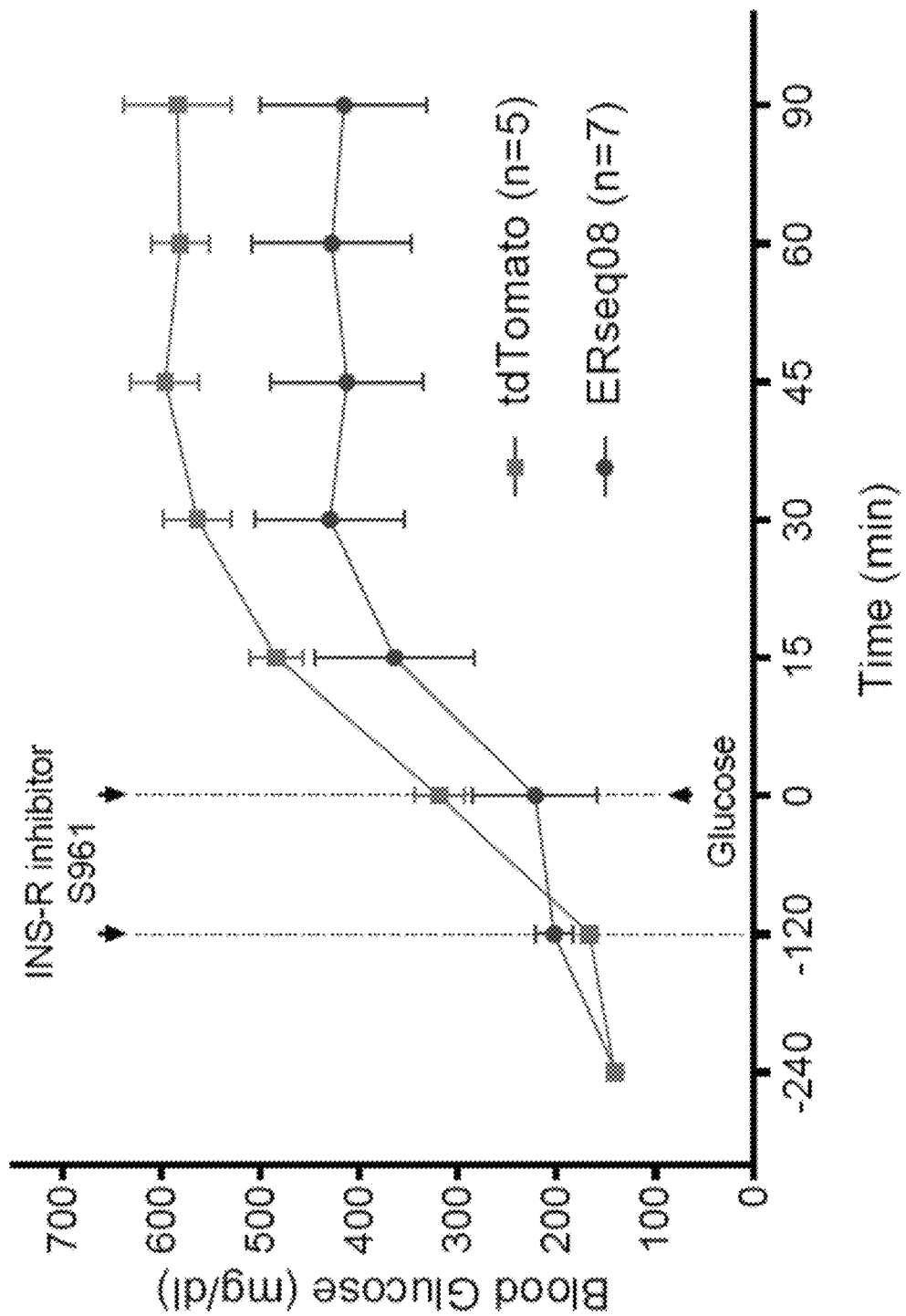
FIG. 22 shows Tumors expressing C1ORF127 suppress hyperglycemia independent of insulin action. Stably transfected HepG2 cell lines expressing C1ORF127 (ERseq80) or control fluorescent protein (tdTomato) were implanted under the kidney capsule of Scid/beige mice and tumors were allowed to grow for a month. A glucose tolerance test was performed after a four hour fast in the presence of the insulin receptor (INS-R) antagonist S961. Note that the control mice quickly become and stay hyperglycemic for the duration of the experiment. C1ORF127 suppresses this hyperglycemic excursion.
Figure 23:
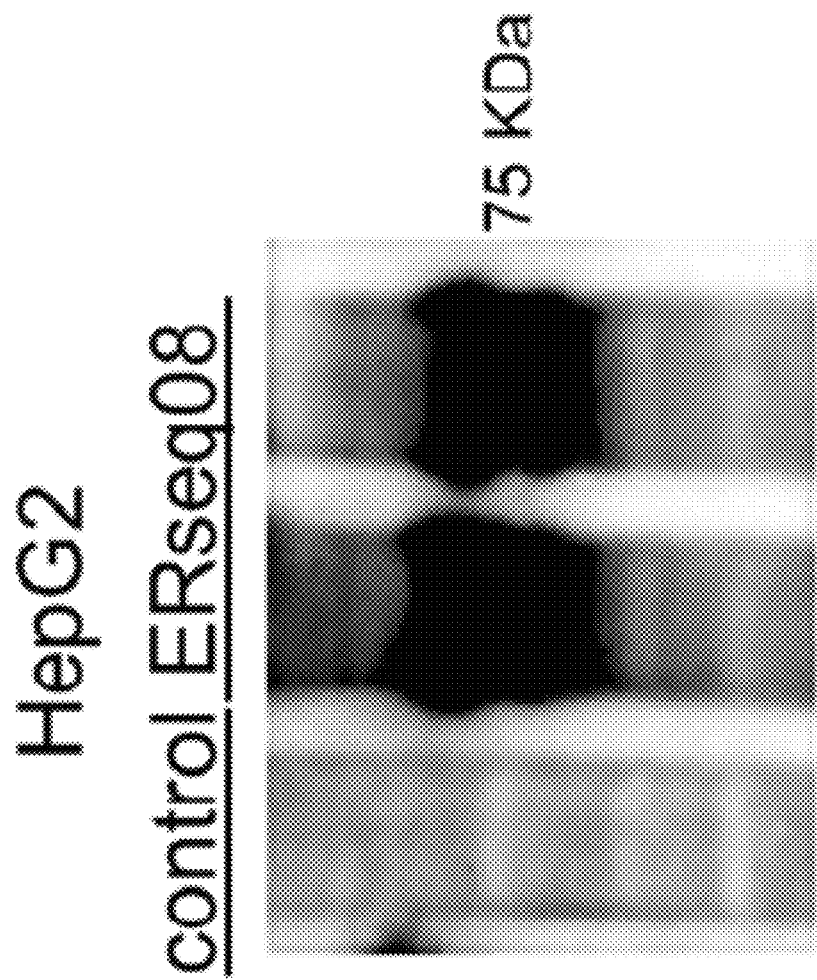
FIG. 23 shows HEPG2 cells express C1ORF127 protein. A commercially available C-terminal antibody was used to perform immunoblot analysis on extracts from stably transfected HEPG2 cells expressing C1ORF127 or control. The expected ~73 kDa product is readily detected.
Figure 24:
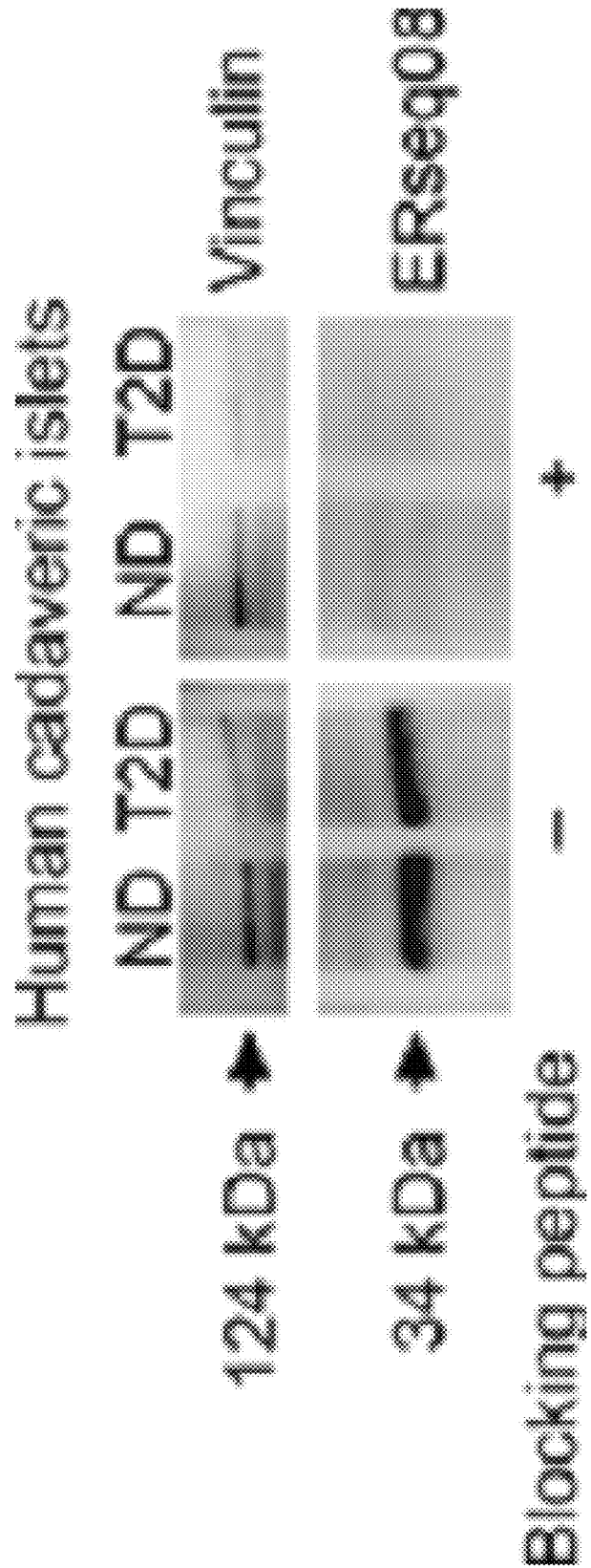
FIG. 24 shows an immunoblot with a rabbit polyclonal antibody raised against a peptide fragment recognizing C1ORF127 (red bar in schematic above). A specific protein band of approximately 34 kDa is seen in both healthy and type-2 diabetic islets and disappears when the antibody is incubated with blocking peptide. The housekeeping protein Vinculin is shown for comparison. This is consistent with RNA expression data. Type 2 diabetic islets appear to have more C1ORF127. Rabbit polyclonal antibody raised against a portion of the conserved domain of C1ORF127 located between the N-terminal and PC2 cleavage site.

Analysis of translocon-associated mRNAs in SC-β cells revealed an enrichment of a significant number of genes that may represent novel secreted factors expressed in SC-β cells. To identify translocon-associates genes that are preferentially expressed in p cells, the ER-seq protocol was applied to cells at multiple stages of the in vitro differentiation of β cells. To do that, the constitutive expression of GFP-SEC61β in the CAAGS::GFP-SEC61β cell line was relied upon to isolate translocon-associated mRNAs in hPSCs and their differentiated progeny during the early stages of differentiation (FIG. 6A). During the last stages of differentiation, the INS::GFP-SEC61β cell line was used to isolate translocon-associated mRNAs in insulin-expressing SC-β cells (FIG. 6A). Translocon-associated mRNAs was sequenced at all stages of differentiation and stage-specific gene expression signatures were identified (FIG. 6B). 601 genes that are differentially expressed across all stages of differentiation were identified. A gene expression signature was found that was specific to SC-β cells that include 139 genes, 44 of which are predicted secreted factors. Gene ontology analysis of SC-β cell-enriched genes showed a significant enrichment of factors involved in insulin secretion, glucose homeostasis, extracellular space, secretory granules, as well as other categories that correlate with secretion and membrane-targeting processes (FIG. 6C-D). Genes involved in insulin secretion and that are preferentially expressed in endocrine cells are significantly upregulated in SC-β cells compared to earlier stages of differentiation (FIG. 6E). Interestingly, 11 unannotated genes that also display an expression pattern specific to SC-β cells (FIG. 6F) were identified. In all, this analysis decodes gene expression signatures that correlate with the differentiation of SC-β cells in vitro and identified a set of genes that are preferentially expressed in this cell type.

Example 3

GreenER Reporter Mouse

A mouse Cre-dependent reporter transgene with the AcGFP-SEC61b fusion protein described above (ROSA-floxed-STOP-floxed-AcGFP-SEC61b) is developed herein and called the GreenER reporter. This mouse has been crossed to Insulin-Cre mice to generate ß-cells whose endoplasmic reticulum fluoresces green, enabling the application of the ER-seq technology described above. This ß-cell specific GreenER strain can be crossed into the NOD model of Type 1 diabetes, giving researchers the ability of finding secreted biomarkers during the course of disease.

Additionally, since some of the stressors common to Type 1 and Type 2 diabetes may be similar, this strain maybe crossed into models of Type 2 diabetes such as the ob/ob and the db/db models.

For mouse ER-seq, the genetic component is the targeting of Green Fluorescent Protein (GFP) fused to an integral component of the ER translocon, Sec61b, to the ROSA locus. Here, a GFP-Sec61b fusion protein was located behind a floxed-flanked transcriptional stop signal. Hence, only in the presence of CRE-recombinase, the transcriptional stop cassette is removed and GFP-Sec61b is expressed marking the ER of CRE-expressing cells with green fluorescence. The biochemical component involves the development of methods to perform subcellular fractionation to make ER-microsomes that preserve the mRNA-ribosome-translocon interaction. Immunoprecipitation using antibodies specific to GFP to precipitate this complex were then performed. The molecular biology component relies on extracting the translocon associated mRNA's from the complex and in performing transcriptional analysis of these mRNA's via RNA sequencing.

Figure 25A:
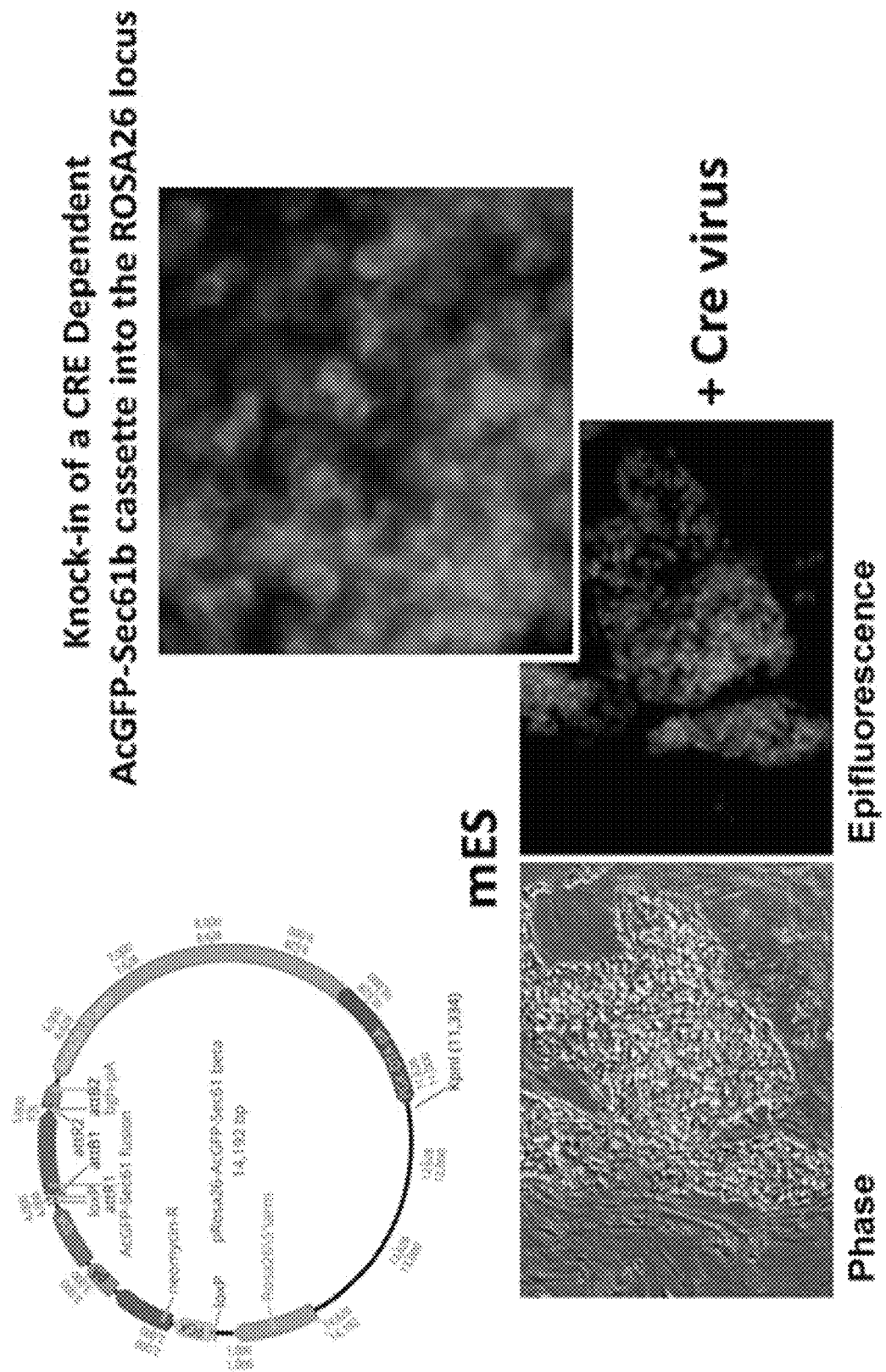
FIGS. 25A-25C show GreenER mouse reporter.

FIG. 25A shows the targeting vector and a positively targeted mouse embryonic stem cell (mESC) colony that was infected with CRE virus to show that the transgene can mark the ER with high fidelity. This colony was used to make our founder reporter mouse strain named Rosa-floxed-STOP-floxed:: Green-ER ("Green-ER" Reporter).

Figure 25B:
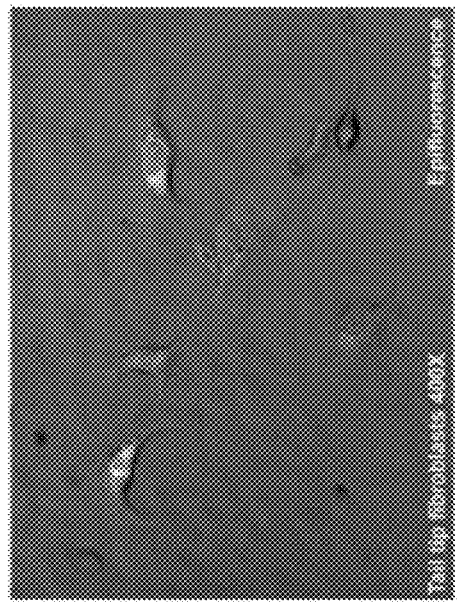

FIG. 25B shows the in vivo validation of the reporter strategy. The Green-ER reporter mouse strain was crossed with a ubiquitous CRE expressing mouse (CMV-Cre). Tail tip fibroblasts were generated from CMV-CRE/Green-ER progeny (Ubiquitous Green-ER mouse) and is shown that the GFP signal in all cells is specific to the ER (false colored yellow in this image).

Figure 25C:
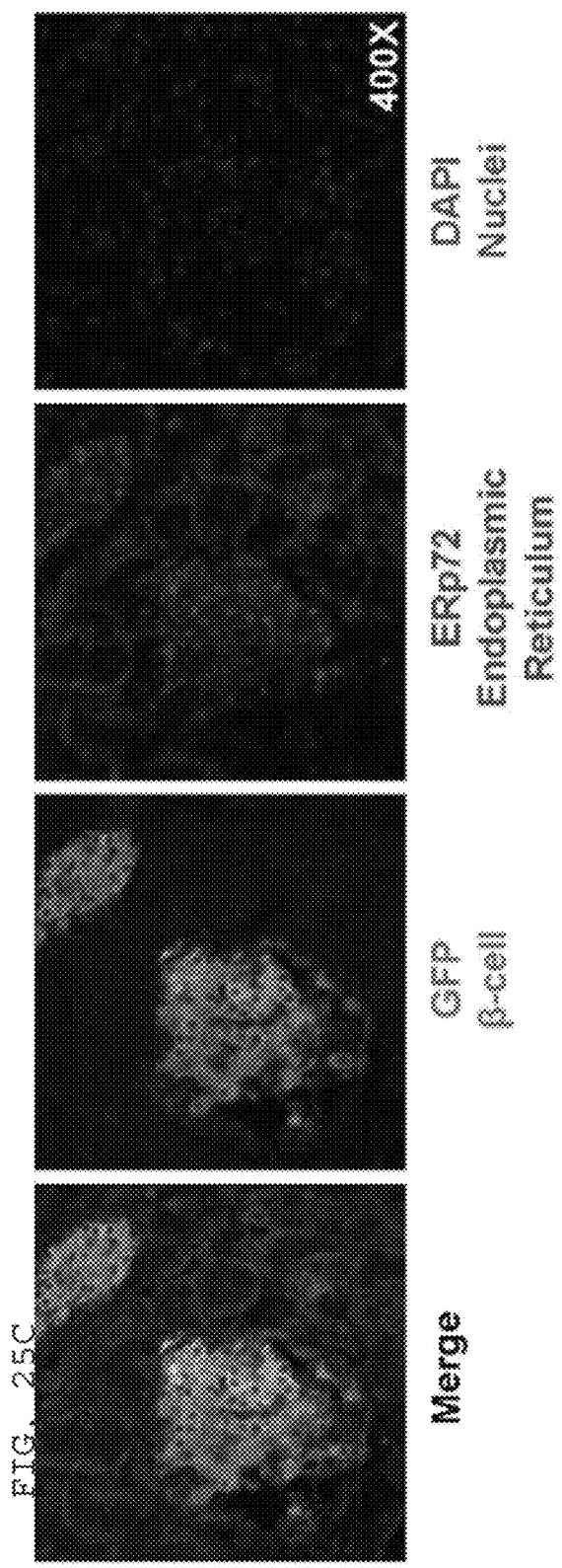
Figure 26:
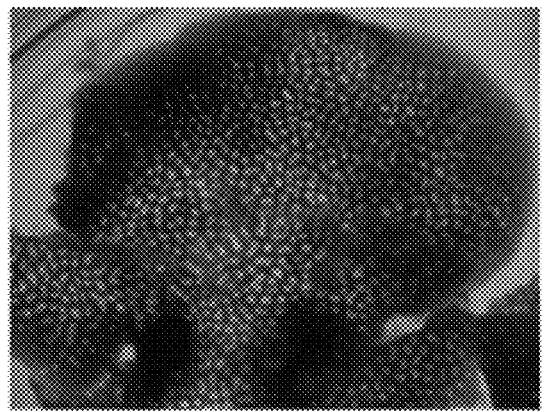
FIG. 26 shows a mouse liver transduced with GFP after HTVi.
Figure 27B:
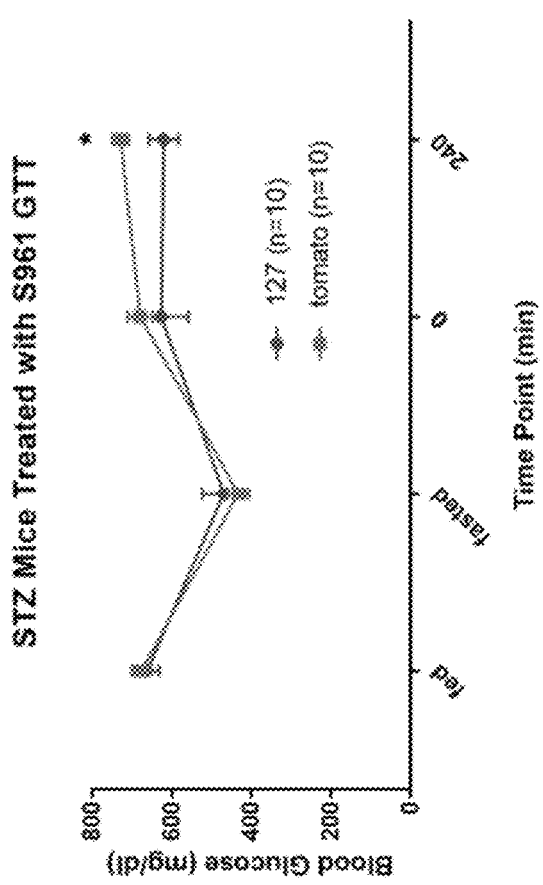
FIGS. 27A-27B show C1ORF127 lowers blood glucose in an ablation model independently of insulin action.
Figure 27A:
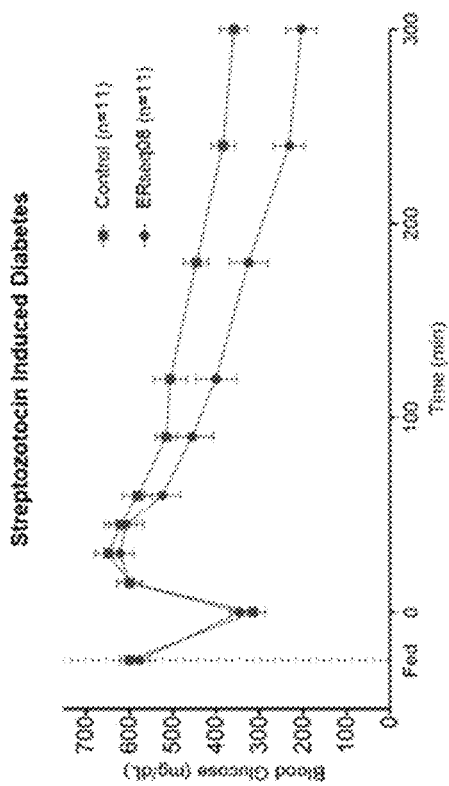

FIG. 25C shows pancreatic sections from progeny of crosses between the Green-ER reporter mouse strain to a beta-cell CRE expressing mouse (Ins2-Cre). This strain was named the beta-cell Green-ER mouse. The recombination is restricted to islet beta-cells and the reporter expression is specific to the ER.

Example 4—Methods

Generation of Transgenic Cell Lines

All the experiments were performed using the human embryonic stem cell line HUES8 obtained from the Human Embryonic Stem Cell Facility and iPS Core Facility of the Harvard Stem Cell Institute. gRNA sequences for the insulin genomic region were ligated into either eCas9 (Addgene 71814) or LbCpf1 (Addgene 84742) CRISPR plasmids. Homology arms flanking ~750 bp upstream and downstream of the stop codon in the last exon of the insulin gene were generated by PCR with primers flanking this region. 5' and 3' homology arms were ligated were ligated to 2A-Sec61β-GFP transgene and a puromycin antibiotic selection marker. For the generation of CAAGS::Sec610-GFP cell line, TALEN constructs were designed to target the safe-harbor AAVS1 locus. 5' and 3' homology arms were ligated were ligated to 2A-PURO (puromycing resistance gene), a linker and CAAGS promoter driving the expression of the Sec61β-GFP transgene. HUES8 cells were dispersed into single cells using TrypLE Express and transfected with targeting vectors using the Nucleofector kit (Invitrogen). 72 hr post-electroporation cells were treated with puromycin at a concentration of 1 g/mL for 7 days to obtain single colonies. Colonies were picked under a microscope around 18-21 days post electroporation into a 96 well plate and expanded. Genomic DNA (gDNA) from the 96 well plate was extracted using the Zymo Research Quick-DNA 96 Plus Kit and insertion of 5' and 3' homology arms was confirmed with PCR. Clones that were confirmed as karyotypically normal by karyotype analysis through Cell Line Genetics were used for directed differentiation towards beta cells.

Differentiation of SC-β Cells

Human pluripotent stem cells (hPSCs) were maintained in mTeSR1 (Stem Cell Technologies) in 500 mL spinner flaks on a stir plate (Chemglass) set to 70 rpm in a 37° C. incubator, 5% CO2, and 100% humidity. Differentiations into SC-β cells were performed following a protocol described previously (Pagliuca et al., 2014) as follows: HUES8 cells were seeded at $6 \times 10^5$ cells/mL in mTeSR1 media and 10 μm Y27632 (Sigma-Aldrich). The media was changed 48 h later and the differentiations were started 72 h after the cells were seeded. The media changes were as follows:

Stage 1 definitive endoderm: S1+100 ng/mL ActivinA (R&D Systems)+3 μM Chir99021 (Stemgent) in day 1 and S1+100 ng/mL ActivinA on day 2.

Stage 2 gut tube endoderm: days 4, 6: S2+50 ng/mL KGF (Peprotech).

Stage 3 pancreatic progenitor 1: days 7, 8: S3+50 ng/mL KGF+0.25 μM Sant1 (Sigma)+2 μM RA (Sigma)+200 nM LDN193189 (only Day 7) (Sigma)+500 nM PdBU (EMD Millipore).

Stage 4 pancreatic progenitor 2: days 9, 11, 13: S3+50 ng/mL KGF+0.25 μM Sant1+100 nM RA+10 μm Y27632+5 ng/mL Activin A.

Stage 5 endocrine progenitors: Days 14, 16: S5+0.25 μM Sant1+100 nM RA+1 μM XXI (EMD Millipore)+10 μM Alk5i II (Axxora)+1 μM T3 (EMD Millipore)+20 ng/mL Betacellulin (Thermo Fisher Scientific). Days 18, 20: S5+25 nM RA+1 μM XXI+10 μM Alk5i II+1 μM T3+20 ng/mL Betacellulin.

Stage 6 β cells: S3 media change every other day. In the final stage, cells were analyzed between 7 and 21 after stage 6 differentiation was started.

Biochemical Fractionation Protocol

Around $100 \times 10^6$ cells were collected from differentiation spinner flasks. To stall ribosomes, 100 μg/mL cycloheximide (CHX) was added and incubated for 10 mins. All the following steps of the fractionation were performed with solutions containing 100 μg/mL cycloheximide (Sigma-Aldrich). Cell clusters were washed in PBS/CHX. 4 mL of Accutase/CHX was added to suspension of cell clusters and incubated for 7 mins RT. Clusters were then dissociated by mechanical dissociation using pipettes, resuspended in PBS/CHX and cells were pelleted with centrifugation for 5 mins at 230 rcf at RT. Pellet was resuspended in 3 mL of cytoplasmic buffer containing 110 mM potassium acetate (Sigma-Aldrich), 25 mM K-HEPES (Sigma-Aldrich), 15 mM magnesium chloride (Sigma-Aldrich), 4 mM calcium chloride (Sigma-Aldrich), 0.015% digitonin, 1.0 mM dithiothreitol (Sigma-Aldrich), 100 μg/ml CHX, 1× cOmplete protease inhibitor cocktail (Millipore) and 500 U/ml RNasin ribonuclease inhibitors (Promega) and incubated for 20 mins at 4° C. Cell suspension was centrifuged for 5 mins at 845 rcf at 4° C. and supernatant (cytoplasmic fraction) and stored at −80° C. for subsequent analysis. The pellet was resuspended in 1 mL ER permeabilization hypotonic buffer containing 20 mM HEPES, 1.5 mM $MgCl_2$, 0.42M NaCl, 0.2 mM EDTA, 25% glycerol, 2% n-Dodecyl j-D-maltoside (DDM), 1.0 mM DTT, 100 μg/ml CHX and 1× cOmplete protease inhibitor cocktail (Millipore) and 500 U/ml RNasin ribonuclease inhibitors (Promega) and 50 uL magnetic agarose binding control beads (Chromotek) and incubated for 1 hour at 4° C. rotating head-to-tail. GFP-MA-TRAP beads (Chromotek) were blocked in 1% BSA-PBS solution for at least 30 mins on ice. Cell extract was homogenized using a Wheaton Glass Homogenizer by slowly moving pestle up and down 15 times. The extract was centrifuged for 5 min at 850 rcf at 4° C. Tube with blocked GFP-MA-TRAP beads was inserted into a DynaMag-2 magnetic stand (Thermo Fisher Scientific) and the solution was discarded. Supernatant was then added to GFP-MA-TRAP bead slurry and incubated for 30 mins at 4° C. with head to tail rotation. Samples were inserted into magnetic stand to collect the unbound fraction and beads were subsequently washed with 500 μL ER Permeabilization buffer twice. After the washes, 500 ul of Trizol was added to beads and stored at −80° C.

RNA Extraction, Library Preparation and Sequencing

Subcellular fractions stored in TRIzol reagent were combined with 0.2 mL chloroform per 1 mL TRIZol reagent used and incubated for 2-3 mins followed by centrifugation for 15 mins at 12,000 rcf at 4° C. The aqueous phase containing the RNA was combined with 0.5 mL isopropanol per 1 mL TRIZol reagent used. After incubating for 10 mins on ice, RNA was precipitated for 10 minutes at 12,000× g at 4° C. Pellet was washed in 1 mL 75% ethanol and air dried for 5-10 mins. RNA was stored at −80° C. in RNA storage solution (Invitrogen) for subsequent analysis.

Precipitated RNA was subjected to in vitro RNA amplification with reverse transcription following a published protocol (Hashimshony et al., 2012). Reverse-transcription primers were designed with an anchored polyT, the 5' Illumina adaptor of Illumina small RNA kit and a T7 promoter. The MessageAmp II RNA kit (Ambion) was used with the modified reverse-transcription primer (Hashimshony et al., 2012). The reaction was performed with 50 ng of RNA and 25 ng/uL amplification primers following MessageAmp II RNA kit's protocol. cDNA cleanup was performed with AMPure XP beads (Beckman coulter) by magnetic bead isolation, cleanup with 80% EtOH followed by in vitro transcription for 13 hours following MessageAmp II RNA kit's protocol. RNA was fragmented in 200 mM Tris-acetate [pH 8.1], 500 mM KOAc, 150 mM MgOAc and reaction was stopped by placing on ice and the addition of one-tenth the volume of 0.5M EDTA, followed by RNA cleanup. RNA quality and yield were assayed using a Bioanalyzer (Agilent). Illumina's directional RNA sequencing protocol was used and only the 3' Illumina adaptor was ligated. A total of 12 cycles of PCR with elongation time of 30 s was performed. Libraries were sequenced using the NextSeq 500 platform (Illumina) according to standard protocols. Paired-end sequencing was performed, reading at least 15 bases for read 1, and 50 bases for read 2, and Illumina barcodes.

Transcriptomic Analysis

Reads were trimmed for universal illumina adapters and polyA sequences with Cutadapt v1.8.1 and assessed for quality control using Fastqc v0.11.5. Reads were aligned to the human reference genome (hg38) with Tophat v2.1.1 using default parameters. Downstream transcript quantification and differential gene expression analysis was performed with Cufflinks v2.2.1 (Trapnell et al., 2013). Differentially expressed genes were defined as those with adjusted p-values below 0.05 using the cuffdiff algorithm.

Gene Ontology Analysis

Differentially expressed genes (adjusted p-value <0.05) were used for gene ontology analysis using WebGestalt GSAT (Wang et al., 2017) and ingenuity pathway analysis (IPA, QIAGEN Inc., www.qiagenbioinformatics.com/products/ingenuity-pathway-analysis)). Gene ontology terms and enriched pathways with P-value <0.05 were considered as enriched in differentially expressed genes.

Prediction of Secreted Factors

Translated protein sequences from candidate transcripts were submitted to the Phobius algorithm to predict signal peptide using a hidden Markov model (Kall et al., 2005). Transcripts with predicted signal peptide but no predicted transmembrane topology were classified as part of the secretome of the cell. Ingenuity pathway analysis (IPA, QIAGEN Inc., www.qiagenbioinformatics.com/products/ingenuity-pathway-analysis) was also used to classify candidate transcripts as cytoplasmic or nuclear.

Western Blot Analysis

After removing the aqueous phase for RNA extraction as described above, the phenol-ethanol was resuspended in 1.5 mL isopropanol per 1 mL TRIzol reagent used and incubated for 10 mins. After centrifugation for 10 mins at 12,000 g at 4° C., the pellet was washed in 2 mL of 0.3 M guanidine hydrochloride in 95% ethanol per 1 mL TRIzol reagent used, incubated for 20 min at RT followed by centrifugation for 5 mins at 7500 g at 4° C. This step was repeated twice. In the final, 2 mL of 100% ethanol per 1 mL TRIzol used was added and incubated for 20 mins. After centrifugation for 5 mins at 7500 g at 4° C., pellet was air dried for 5-10 mins and resuspended in 200 uL of 1% SDS buffer. Protein concentration was measured using the BCA Protein Assay kit (Thermo Scientific). 5-10 ug of protein extracts were separated by AnyKD Mini-Protein precast gels (Bio-Rad) and transferred to nitrocellulose membranes (Bio-Rad). Membranes were blocked in 3% BSA+0.1% Tween 20 TBS for 30 mins at RT and then incubated with the following primary antibodies overnight at 4° C.: mouse anti-Sec61β (Santa Cruz, sc-393633), chick anti-GFP (Aves, GFP1020), rabbit anti-ribosomal protein L13a (Cell signaling, 2765). After washing, the membranes were incubated with HRP-conjugated secondary antibodies for 1 h at RT, and then incubated in chemiluminescent ECL detection reagent (VWR) for signal detection and development.

4.5.9 Animals Studies

All animal treatment, husbandry, procedures were done in accordance with institutional animal care standards. All protocols were approved by Harvard University's Institutional Animal Care and Use Committee. Initial screening of ER-seq candidates by tail vein injection was performed using ICR mice obtained from Jackson Laboratory. Additional tail vein injections for characterization of c1orf127, including S961 experiments, were performed using C57BL/6 mice from Charles River Laboratory. Streptasatozin induced diabetic mice were C57BL/6 mice obtained from Jackson Laboratory, STZ injections were performed by Jackson Laboratory.

Candidate Cloning

Expression plasmids for screened ER-Seq candidates were obtained first by PCR amplification from cDNA libraries of stem cell derived beta-cells; primers were designed to add gateway cloning sites. Because of difficulty amplifying C1orf127, a clone of the ORF was purchased from Dharmacon and amplified to add gateway sites. PCR amplicons were added to PDonor gateway vector. The ORFs were then transferred into CaG high expression vectors (for tail vein injection) and into lentiviral production vectors (cell line production). In addition to ER-Seq candidates, controls including cytoplasmic GFP, nuclear TD-Tomato, furin-cleavable insulin, and a nanoluciferase were purchased as custom genes with gateways sites from Integrated DNA Technologies. Controls were then cloned into the same vectors.

Tail Vein Injections

Mice were first anaesthetized by intraperitoneal injection 23 ul/g bodyweight of a 1.25% Avertin solution. Tails of anaesthetized mice were warmed under a heat lamp to dilate the tail vein. Anaesthetized mice received an injection of 80 ul/g bodyweight of saline with 35 ug of expression vector DNA in the tail vein over approximately 7 seconds. For experiments involving tail vein injected mice, mice were tested 48-72 hrs after injections.

Standard Glucose Tolerance Tests

Mice were fasted overnight (5 pm to 9 am). Blood glucose measurements were taken before fasting and immediately before glucose injections. Mice received an intraperitoneal injection of glucose at 2 g/kg bodyweight. Blood glucose measurements were then taken at 15, 30, 45, 60 and 90 minutes post injection. Occasionally a 120 minute time point was collected if blood glucoses had not yet fallen below normal levels (<250 mg/dl).

S961 Glucose Tolerance Tests

Mice were fasted overnight (5 pm to 9 am). Blood glucose measurements were taken before fasting, immediately before initial S961 injection and before glucose injection. Mice received an intraperitoneal injection of 10 ul/g bodyweight of 45 uM S961. 2 hours after this initial injection, mice received an intraperitoneal injection of 10 ul/g bodyweight of 30 uM S961, 15% D-Glucose (1.5 g/kg glucose). Blood glucose measurements were then taken at 15, 30, 45, 60, 90, 120 minutes post injection, and then measures were taken hourly until values fell below normal (<250 mg/dl).

STZ Glucose Tolerance Tests

Blood glucose measurements were taken before tail vein injection, before fasting and immediately before glucose injection. Only mice with initially severe hyperglycemia (>400 mg/dl) were used. Mice were fasted overnight (5 pm to 9 am). Mice received an intraperitoneal injection of 1.5 g/kg glucose. Blood glucose measurements were then taken at 15, 30, 45, 60, 90, 120 minutes post injection, and then measures were taken hourly until values fell below normal (<250 mg/dl).

Statistical Analysis

Statistical analysis was performed using GraphPad Prism software. Glucose tolerance comparisons were made using t-tests for both individual time-points. ANOVA and Tukey's multiple comparison tests were used to compare areas under the curve.

REFERENCES

American Diabetes Association. (2018) 8. Pharmacologic approaches to glycemic treatment: Standards of Medical Care in Diabetes. 2018. Diabetes Care 41, S73-S85. Basic and Clinical Physiology and Pharmacology 27, 445-456.

Benni, J. & Patil, P. (2016). Non-diabetic clinical applications of insulin. Journal of Bergeonneau, C., Kassaï, B., Erpeldinger, S., Wright, J. M., Gueyffier, F., Cornu, C. (2011) Effect of intensive glucose lowering treatment on all cause mortality, cardiovascular death, and microvascular events in type 2 diabetes: meta-analysis of randomised controlled trials. BMJ 343, d4169.

Boussageon, R., Bejan-Angoulvant, T., Saadatian-Elahi, M., Lafont, S., Chen, C. A., Carolan, P. J., & Annes, J. P. (2012) In vivo screening for secreted proteins that modulate glucose handling identifies interleukin-6 family members as potent hypoglycemic agents. PLoS One 7, e44600.

Diehn, M., Eisen, M., Botstein, D., & Brown, P. (2000). Large-scale identification of secreted and membrane-associated gene products using DNA microarrays. Nat. Genetics 25, 58-62.

Emanuelsson, O., Brunak, S., von Heijne, G. et al. (2007) Locating proteins in the cell using TargetP, SignalP and related tools. Nat. Protoc., 2, 953-971.

Fazal, F. M., Han, S., Parker, K. R., Kaewsapsak, P., Xu, J., Boettiger, A. N., Chang, H. W., & Ting, A. Y. (2019) Atlas of Subcellular RNA Localization Revealed by APEX-Seq. Cell 178, 1-18.

Gepts, W. (1965) Pathologic anatomy of the pancreas in juvenile diabetes mellitus. Diabetes 14, 619-633.

Hashimshony, T., Wagner, F., Sher, N. & Yanai I. (2012) CEL-Seq: Single-Cell RNA-Seq by Multiplexed Linear Amplification. Cell Reports 2, 666-673.

Jan, C. H., Williams, C. C., & Weissman, J. S. (2014) Principles of ER cotranslational translocation revealed by proximity-specific ribosome profiling. Science 346, 1257521.

Kall, L., Krogh, A., & Sonnhammer, E. (2005) An HMM posterior decoder for sequence feature prediction that includes homology information. Bioinformatics 21, i251-i257.

Kall, L., Krogh, A., Sonnhammer, E. L. (2004) A combined transmembrane topology and signal peptide prediction method. J. Mol. Biol. 338, 1027-1036.

Mandon, E. C., Trueman, S. F., Gilmore, R. (2013) Protein translocation across the rough endoplasmic reticulum. Cold Spring Harb. Perspect. Biol. 5, a013342.

Meinken, J., Walker, G., Cooper, C., & Min, X. (2015). MetazSecKB: the human and animal secretome and subcellular proteome knowledgebase. Database, bav077.

Ogg, S. C., Walter, P. (1995) SRP samples nascent chains for the presence of signal sequences by interacting with ribosomes at a discrete step during translation elongation. Cell 81, 1075-1084.

Pagliuca, F., Millman, J. R., Gurtler, M., Segel, M., Van Dervort, A., Ryu, J. H., Peterson, Q. P., Greiner, D., and Melton D. A. (2014) Generation of functional human pancreatic β cells in vitro. Cell 159, 428-439.

Petersen, T. N., Brunak, S., von Heijne, G., & Nielsen, H. (2011) SignalP 4.0: Discriminating signal peptides from transmembrane regions. Nat. Methods 8, 785-786.

Rapoport, T. (2007) Protein translocation across the eukaryotic endoplasmic reticulum and bacterial plasma membranes. Nature 450, 663-669.

Pipeleers, D., Ling, Z. (1992) Pancreatic beta cells in insulin-dependent diabetes. Diabetes Metab Rev 8, 209-227.

Reid, D. W., Chen, Q., Tay, A. S. L., Shenolikar, S., & Nicchitta, C. V. (2014) The Unfolded Protein Response Triggers Selective mRNA Release from the Endoplasmic Reticulum. Cell 158, 1362-1374.

Schaffer, L, Brand, C. L., Hansen, B. F., Ribel, U., Shaw, A. C., Slaaby, R., & Sturis, J. (2008) A novel high-affinity peptide antagonist to the insulin receptor. Biochem Biophys Res Commun. 376, 380-3.

Uhlén, M., Fagerberg, L., Hallstrom, B. M., Lindskog, C., Oksvold, P., Mardinoglu, A., Sivertsson, Å., Kampf, C., Sjöstedt. E., Asplund, A., et al (2015) Tissue-based map of the human proteome. Science 347, 1260419.

Example 5

Alternative Sample ER-Seq Protocol

Permeabilization Buffer Stock (to Make Cytoplasmic Extraction Buffer)

|  | for 50 ml |
| --- | --- |
| 110 mM KOAc | 1.83 ml of 3M |
| 25 mM K-HEPES 7.2 | 2.5 ml of 0.5M |
| 15 mM MgCl2 | 750 µl of 1M |
| 4 mM CaCl2 | 200 µl of 1M |
| RNAse free water | 44.72 ml |

Hypotonic Buffer Stock (50 mL; to Make ER Permeabilization Buffer)

| Nuclease-free water | 32.2 mL |
|---|---|
| 20 mM HEPES | 1 mL of 1M |
| 1.5 mM MgCl2 | 75 uL of 1M |
| 0.42M NaCl | 4.2 mL of 5M |
| 0.2 mM EDTA | 20 uL of 0.5M |
| 25% (v/v) glycerol | 12.5 mL of 100% |

Cytoplasmic Buffer (2 mL)

| Permeabilization Stock | 951.5 µl × 2 |
|---|---|
| 0.015% Digitonin | 30 µl of 1% |
| 1.0 mM DTT | 20 µl of 100 mM |
| 100 µg/ml CHX | 2.0 µl of 100 mg/ml |
| 1X Protease Inh Cocktail | 20.0 µl of 10X |
| 500U/ml RNAsin | 25.0 µl of 40U/pl |

ER Permeabilization Buffer (4 mL)

| Hypotonic Buffer Stock | 3.066 mL |
|---|---|
| 2% DDM | 800 uL of 10% |
| 1.0 mM DTT | 40 µl of 100 mM |
| 100 µg/ml CHX | 4.0 µl of 100 mg/ml |
| Protease Inh Cocktail | 40.0 µl of 10X |
| 500U/ml RNAsin | 50.0 µl of 40U/µl |

CHX/PBS:100 µg/ml CHX (30 µl of 100 mg/ml CHX in 30 ml PBS w/o cations)

CHX/Accutase (8 ml): 8 µl CHX into 4 ml PBS+4 mL Accutase

GFP-MA TRAP magnetic beads (2×): 100 uL beads+100 uL BSA+400 uL permeabilization stock (we have used 50 uL beads for 60×10$^6$ cells)

10× Protease Inhibitor cocktail: 1 tablet in 1 ml DMSO

Modifications to the Protocol:

Collect 130 mL from 2 St5d7 spinner flasks (3×50 mL tubes)

Let clusters settle for 5 mins (remove all but 10 mL)

Add 10 uL CHX (100 ug/mL)

Incubate in rocker for 5 mins

Let clusters settle for 5 mins in 10 mL PBS/CHX

Add 4 mL CHX/Accutase and incubate for 7 mins gently shaking every 2 mins.

Centrifuge for 5 mins @ 200 rcf

Resuspend in 3 mL cytoplasmic buffer, split into 2 1.5 mL tubes, and incubate for 20 mins Centrifuge for 5 mins @ 845 g in cold room's centrifuge.

Add 1 mL ER permeabilization buffer and 50 uL GFP binding control beads to each sample Incubate for 1 hr and proceed to permeabilize and pull-down and described before Homogenize using Wheaton Glass Homogenizer (moving the pestle up and down 15 times slowly)

Transfer extract to a new 1.5 mL centrifuge tube and spin down for 5 min at 3000 rpm in the cold room's centrigue Add supernatant to pre-blocked GFP-MA-TRAP bead slurry (pellet is the nuclear fraction).

Incubate bead slurry with head to tail rotation in the cold room for 30 min.

Retrieve tube from cold room and apply magnet for at least 1 min. Your bound fraction should contain the translocon associated mRNAs. Collect the supernatant into a 15 ml conical tube. This is your translocon depleted membrane fraction. Save 2 µl from the translocon depleted membrane fraction for epifluorescence analysis. Add 2.5 ml of Trizol and freeze at −80 C.

Wash beads twice with 500 µl ER Permeabilization buffer. Transfer to a new tube. Save 2 µl from your Translocon enriched fraction for epifluorescence analysis. Apply magnet and discard supernatant. Add 500 ul of Trizol to beads. Vortex and freeze at −80° C.

We claim:

1. An agent comprising an isolated, non-naturally occurring polypeptide having an amino acid sequence having at least about 95% identity to SEQ ID NO: 5 and having at least one differently phosphorylated amino acid or at least one differently glycosylated amino acid compared to an amino acid sequence consisting of SEQ ID NO: 2.

2. The agent of claim 1, wherein the isolated, non-naturally occurring polypeptide has at least one differently phosphorylated amino acid compared to an amino acid sequence consisting of SEQ ID NO: 2.

3. The agent of claim 2, wherein the isolated, non-naturally occurring polypeptide has one less phosphorylated amino acid compared to an amino acid sequence consisting of SEQ ID NO: 2.

4. The agent of claim 2, wherein the isolated, non-naturally occurring polypeptide has one more phosphorylated amino acid compared to an amino acid sequence consisting of SEQ ID NO: 2.

5. The agent of claim 1, wherein the isolated, non-naturally occurring polypeptide has at least one differently glycosylated amino acid compared to an amino acid sequence consisting of SEQ ID NO: 2.

6. The agent of claim 5, wherein the isolated, non-naturally occurring polypeptide has one less glycosylated amino acid compared to an amino acid sequence consisting of SEQ ID NO: 2.

7. The agent of claim 5, wherein the isolated, non-naturally occurring polypeptide has two less glycosylated amino acid compared to an amino acid sequence consisting of SEQ ID NO: 2.

8. The agent of claim 5, wherein the isolated, non-naturally occurring polypeptide has one more glycosylated amino acid compared to an amino acid sequence consisting of SEQ ID NO: 2.

9. The agent of claim 5, wherein the isolated, non-naturally occurring polypeptide has two more glycosylated amino acids compared to an amino acid sequence consisting of SEQ ID NO: 2.

10. The agent of claim 1, wherein the isolated, non-naturally occurring polypeptide produces a protein having a molecular weight of approximately 57 kDa.

* * * * *

SEQUENCE LISTING

<160> NUMBER OF SEQ ID NOS: 5

<210> SEQ ID NO 1
<211> LENGTH: 2052
<212> TYPE: DNA
<213> ORGANISM: Homo sapiens

<400> SEQUENCE: 1

```
atggggttgg agcggagtga tcgctacata atgaagtgtc cgatgctaag gtcaaggctg      60
ggtcaggaaa gcgtccactg tgggcccatg ttcatccagg tctccggcc cctgcccctg     120 tggagggaca atagacagac tccatggctg ctgtcccttc gagggagct ggtggcttct     180 cttgaagacg ccagcctgat gggactgtat gtggacatga atgccaccac tgtcaccgtc     240
caaagcccga gacaaggcct tcttcagagg tgggaggtgc tgaacacctc tgctgagctc     300
ctgccactat ggctggtgag cggtcaccat gcctattctt tagaagctgc ttgcccaccg     360
gtgtcattcc agccagagtc ggaggtctta gttcacatcc ccaagcagag actgggtcta     420
gtcaaaagag gttcctacat tgaggaaacc ctgagcctca gattcctccg agtccaccag     480
tccaacatct ttatggtgac tgagaacaag gactttgtgg tggtcagcat tccggcggcc     540
ggggtgctcc aggtccagcg atgccaagaa gtcgaggaa ccccgggaac acaagctttc     600
tatagggtag acctgagcct ggaatttgcc gagatggctg ccccggtcct ctggacagtg     660
```

-continued

```
gagagcttct tccagtgtgt gggttcagga acagagtcgc ctgcctcaac tgctgcactg    720
aggaccactc cctccccacc atccccagga ccagagaccc ctccagcggg agtgccacct    780
gctgcttcct cccaggtgtg gctgcagga ccagctgccc aggaatggct ttctcgggac    840
ctcctgcacc ggccttccga cgcactggcc aaaaaggggc ttggaccatt cctgcaaaca    900
gccaaccggc gagaagagg ccagacatct gcctccattc tccccagagt ggtgcaagct    960
cagcgaggtc cccagcctcc cccaggggaa gcagggatcc ctggacaccc cacacctcca    1020
gccacgctcc cctcggagcc tgtagagggt gtccaggcta gtccctggcg ccacgtcca    1080 gtcttgccaa cgcacccggc tctgaccctg cccgtgtcct cagatgcctc ctctccttca    1140
ccgccagccc cgaggcctga acgacctgaa tcacttctgg tctcaggacc atctgtcacc    1200
ctgactgaag gtctaggaac tgtgaggcct gaacaggacc ccgccaagtc tccaggaagt    1260
cccctcctgc tgagaggctt gtcaagcggg gatgtggctg cacctgagcc catcatgggg    1320
gagcccggcc aagccagtga ggagttccag ccattggcga ggccctggcg ggccacactg    1380
gctgcagagg agctggtttc tcaccgttct cccggagagc cccaggaaac gtgctctgga    1440
acggaggtgg agaggccacg ccagacaggg cctggtctcc ccaggagggg ggccagggg    1500 cacatggacc tttcatcctc agaaccaagc caggacatag aggggccggg actctccatc    1560
ctgccagcga gggatgccac attctccacc ccaagtgtga ggcagccaga ccccagtgcc    1620
tggctgagtt caggacctga actcaccggg atgcccaggg tgaggctggc agcgcccctg    1680
gcagttcttc ctatggaacc tctgccacca gaacctgttc gcccagcagc tcttctgaca    1740
cccgaagcct catctgtggg agggccagac caggcccgat acctggagtc agcccctggc    1800
tggcctgtgg gccaggagga gtgggggtt gcacacacgt ccagccctcc atccacgcaa    1860
accctgagcc tgtgggctcc cacaggagtg ttgctaccca gcctggtgga gcttgaatac    1920
cccttccagg ctggccgggg ggcctcactc cagcaggagc tgacagagcc caccttggcc    1980
ctcagtgctg aaagccacag gcctcctgag cttcaagaca gtgtggaggg gctttctgag    2040
aggccctcac gc                                                        2052
```

<210> SEQ ID NO 2
<211> LENGTH: 684
<212> TYPE: PRT
<213> ORGANISM: Homo sapiens

<400> SEQUENCE: 2

```
Met Gly Leu Glu Arg Ser Asp Arg Tyr Ile Met Lys Cys Pro Met Leu
1               5                   10                  15

Arg Ser Arg Leu Gly Gln Glu Ser Val His Cys Gly Pro Met Phe Ile
            20                  25                  30

Gln Val Ser Arg Pro Leu Pro Leu Trp Arg Asp Asn Arg Gln Thr Pro
        35                  40                  45

Trp Leu Leu Ser Leu Arg Gly Glu Leu Val Ala Ser Leu Glu Asp Ala
    50                  55                  60

Ser Leu Met Gly Leu Tyr Val Asp Met Asn Ala Thr Thr Val Thr Val
65                  70                  75                  80

Gln Ser Pro Arg Gln Gly Leu Leu Gln Arg Trp Glu Val Leu Asn Thr
                85                  90                  95

Ser Ala Glu Leu Leu Pro Leu Trp Leu Val Ser Gly His His Ala Tyr
            100                 105                 110

Ser Leu Glu Ala Ala Cys Pro Pro Val Ser Phe Gln Pro Glu Ser Glu
        115                 120                 125
```

```
Val Leu Val His Ile Pro Lys Gln Arg Leu Gly Leu Val Lys Arg Gly
    130                 135                 140

Ser Tyr Ile Glu Glu Thr Leu Ser Leu Arg Phe Leu Arg Val His Gln
145                 150                 155                 160

Ser Asn Ile Phe Met Val Thr Glu Asn Lys Asp Phe Val Val Ser
                165                 170                 175

Ile Pro Ala Ala Gly Val Leu Gln Val Gln Arg Cys Gln Glu Val Gly
                180                 185                 190

Gly Thr Pro Gly Thr Gln Ala Phe Tyr Arg Val Asp Leu Ser Leu Glu
            195                 200                 205

Phe Ala Glu Met Ala Ala Pro Val Leu Trp Thr Val Glu Ser Phe Phe
    210                 215                 220

Gln Cys Val Gly Ser Gly Thr Glu Ser Pro Ala Ser Thr Ala Ala Leu
225                 230                 235                 240

Arg Thr Thr Pro Ser Pro Pro Ser Pro Gly Pro Glu Thr Pro Pro Ala
                245                 250                 255

Gly Val Pro Pro Ala Ala Ser Ser Gln Val Trp Ala Ala Gly Pro Ala
                260                 265                 270

Ala Gln Glu Trp Leu Ser Arg Asp Leu Leu His Arg Pro Ser Asp Ala
            275                 280                 285

Leu Ala Lys Lys Gly Leu Gly Pro Phe Leu Gln Thr Ala Lys Pro Ala
    290                 295                 300

Arg Arg Gly Gln Thr Ser Ala Ser Ile Leu Pro Arg Val Val Gln Ala
305                 310                 315                 320

Gln Arg Gly Pro Gln Pro Pro Gly Glu Ala Gly Ile Pro Gly His
                325                 330                 335

Pro Thr Pro Pro Ala Thr Leu Pro Ser Glu Pro Val Glu Gly Val Gln
                340                 345                 350

Ala Ser Pro Trp Arg Pro Arg Pro Val Leu Pro Thr His Pro Ala Leu
            355                 360                 365

Thr Leu Pro Val Ser Ser Asp Ala Ser Ser Pro Ser Pro Ala Pro
    370                 375                 380

Arg Pro Glu Arg Pro Glu Ser Leu Leu Val Ser Gly Pro Ser Val Thr
385                 390                 395                 400

Leu Thr Glu Gly Leu Gly Thr Val Arg Pro Glu Gln Asp Pro Ala Lys
                405                 410                 415

Ser Pro Gly Ser Pro Leu Leu Leu Arg Gly Leu Ser Ser Gly Asp Val
                420                 425                 430

Ala Ala Pro Glu Pro Ile Met Gly Glu Pro Gly Gln Ala Ser Glu Glu
            435                 440                 445

Phe Gln Pro Leu Ala Arg Pro Trp Arg Ala Thr Leu Ala Ala Glu Glu
    450                 455                 460

Leu Val Ser His Arg Ser Pro Gly Glu Pro Gln Glu Thr Cys Ser Gly
465                 470                 475                 480

Thr Glu Val Glu Arg Pro Arg Gln Thr Gly Pro Gly Leu Pro Arg Glu
                485                 490                 495

Gly Ala Arg Gly His Met Asp Leu Ser Ser Ser Glu Pro Ser Gln Asp
                500                 505                 510

Ile Glu Gly Pro Gly Leu Ser Ile Leu Pro Ala Arg Asp Ala Thr Phe
            515                 520                 525

Ser Thr Pro Ser Val Arg Gln Pro Asp Pro Ser Ala Trp Leu Ser Ser
    530                 535                 540
```

```
Gly Pro Glu Leu Thr Gly Met Pro Arg Val Arg Leu Ala Ala Pro Leu
545                 550                 555                 560

Ala Val Leu Pro Met Glu Pro Leu Pro Glu Pro Val Arg Pro Ala
            565                 570                 575

Ala Leu Leu Thr Pro Glu Ala Ser Ser Val Gly Gly Pro Asp Gln Ala
            580                 585                 590

Arg Tyr Leu Glu Ser Ala Pro Gly Trp Pro Val Gly Gln Glu Glu Trp
            595                 600                 605

Gly Val Ala His Thr Ser Ser Pro Pro Ser Thr Gln Thr Leu Ser Leu
            610                 615                 620

Trp Ala Pro Thr Gly Val Leu Leu Pro Ser Leu Val Glu Leu Glu Tyr
625                 630                 635                 640

Pro Phe Gln Ala Gly Arg Gly Ala Ser Leu Gln Gln Glu Leu Thr Glu
            645                 650                 655

Pro Thr Leu Ala Leu Ser Ala Glu Ser His Arg Pro Pro Glu Leu Gln
            660                 665                 670

Asp Ser Val Glu Gly Leu Ser Glu Arg Pro Ser Arg
            675                 680
```

<210> SEQ ID NO 3
<211> LENGTH: 215
<212> TYPE: PRT
<213> ORGANISM: Homo sapiens

<400> SEQUENCE: 3

```
Lys Cys Pro Met Leu Arg Ser Arg Leu Gly Gln Glu Ser Val His Cys
1               5                   10                  15

Gly Pro Met Phe Ile Gln Val Ser Arg Pro Leu Pro Leu Trp Arg Asp
            20                  25                  30

Asn Arg Gln Thr Pro Trp Leu Leu Ser Leu Arg Gly Glu Gly Leu Val Ala
            35                  40                  45

Ser Leu Glu Asp Ala Ser Leu Met Gly Leu Tyr Val Asp Met Asn Ala
50                  55                  60

Thr Thr Val Thr Val Gln Ser Pro Arg Gln Gly Leu Leu Gln Arg Trp
65                  70                  75                  80

Glu Val Leu Asn Thr Ser Ala Glu Leu Leu Pro Leu Trp Leu Val Ser
                85                  90                  95

Gly His His Ala Tyr Ser Leu Glu Ala Ala Cys Pro Pro Val Ser Phe
            100                 105                 110

Gln Pro Glu Ser Glu Val Leu Val His Ile Pro Lys Gln Arg Leu Gly
            115                 120                 125

Leu Val Lys Arg Gly Ser Tyr Ile Glu Glu Thr Leu Ser Leu Arg Phe
130                 135                 140

Leu Arg Val His Gln Ser Asn Ile Phe Met Val Thr Glu Asn Lys Asp
145                 150                 155                 160

Phe Val Val Val Ser Ile Pro Ala Ala Gly Val Leu Gln Val Gln Arg
                165                 170                 175

Cys Gln Glu Val Gly Gly Thr Pro Gly Thr Gln Ala Phe Tyr Arg Val
            180                 185                 190

Asp Leu Ser Leu Glu Phe Ala Glu Met Ala Ala Pro Val Leu Trp Thr
            195                 200                 205

Val Glu Ser Phe Phe Gln Cys
    210                 215
```

<210> SEQ ID NO 4

```
<211> LENGTH: 83
<212> TYPE: PRT
<213> ORGANISM: Homo sapiens

<400> SEQUENCE: 4

Gly Ser Tyr Ile Glu Glu Thr Leu Ser Leu Arg Phe Leu Arg Val His
1               5                   10                  15

Gln Ser Asn Ile Phe Met Val Thr Glu Asn Lys Asp Phe Val Val Val
                20                  25                  30

Ser Ile Pro Ala Ala Gly Val Leu Gln Val Gln Arg Cys Gln Glu Val
            35                  40                  45

Gly Gly Thr Pro Gly Thr Gln Ala Phe Tyr Arg Val Asp Leu Ser Leu
50                  55                  60

Glu Phe Ala Glu Met Ala Ala Pro Val Leu Trp Thr Val Glu Ser Phe
65                  70                  75                  80

Phe Gln Cys

<210> SEQ ID NO 5
<211> LENGTH: 541
<212> TYPE: PRT
<213> ORGANISM: Homo sapiens

<400> SEQUENCE: 5

Gly Ser Tyr Ile Glu Glu Thr Leu Ser Leu Arg Phe Leu Arg Val His
1               5                   10                  15

Gln Ser Asn Ile Phe Met Val Thr Glu Asn Lys Asp Phe Val Val Val
                20                  25                  30

Ser Ile Pro Ala Ala Gly Val Leu Gln Val Gln Arg Cys Gln Glu Val
            35                  40                  45

Gly Gly Thr Pro Gly Thr Gln Ala Phe Tyr Arg Val Asp Leu Ser Leu
50                  55                  60

Glu Phe Ala Glu Met Ala Ala Pro Val Leu Trp Thr Val Glu Ser Phe
65                  70                  75                  80

Phe Gln Cys Val Gly Ser Gly Thr Glu Ser Pro Ala Ser Thr Ala Ala
                85                  90                  95

Leu Arg Thr Thr Pro Ser Pro Ser Pro Gly Pro Glu Thr Pro Pro
            100                 105                 110

Ala Gly Val Pro Pro Ala Ala Ser Ser Gln Val Trp Ala Ala Gly Pro
        115                 120                 125

Ala Ala Gln Glu Trp Leu Ser Arg Asp Leu Leu His Arg Pro Ser Asp
130                 135                 140

Ala Leu Ala Lys Lys Gly Leu Gly Pro Phe Leu Gln Thr Ala Lys Pro
145                 150                 155                 160

Ala Arg Arg Gly Gln Thr Ser Ala Ser Ile Leu Pro Arg Val Val Gln
                165                 170                 175

Ala Gln Arg Gly Pro Gln Pro Pro Gly Glu Ala Gly Ile Pro Gly
            180                 185                 190

His Pro Thr Pro Pro Ala Thr Leu Pro Ser Glu Pro Val Glu Gly Val
        195                 200                 205

Gln Ala Ser Pro Trp Arg Pro Arg Pro Val Leu Pro Thr His Pro Ala
    210                 215                 220

Leu Thr Leu Pro Val Ser Ser Asp Ala Ser Ser Pro Ser Pro Pro Ala
225                 230                 235                 240

Pro Arg Pro Glu Arg Pro Glu Ser Leu Leu Val Ser Gly Pro Ser Val
                245                 250                 255
```

-continued

```
Thr Leu Thr Glu Gly Leu Gly Thr Val Arg Pro Glu Gln Asp Pro Ala
            260                 265                 270

Lys Ser Pro Gly Ser Pro Leu Leu Leu Arg Gly Leu Ser Ser Gly Asp
        275                 280                 285

Val Ala Ala Pro Glu Pro Ile Met Gly Glu Pro Gly Gln Ala Ser Glu
    290                 295                 300

Glu Phe Gln Pro Leu Ala Arg Pro Trp Arg Ala Thr Leu Ala Ala Glu
305                 310                 315                 320

Glu Leu Val Ser His Arg Ser Pro Gly Glu Pro Gln Glu Thr Cys Ser
                325                 330                 335

Gly Thr Glu Val Glu Arg Pro Arg Gln Thr Gly Pro Gly Leu Pro Arg
            340                 345                 350

Glu Gly Ala Arg Gly His Met Asp Leu Ser Ser Ser Glu Pro Ser Gln
            355                 360                 365

Asp Ile Glu Gly Pro Gly Leu Ser Ile Leu Pro Ala Arg Asp Ala Thr
370                 375                 380

Phe Ser Thr Pro Ser Val Arg Gln Pro Asp Pro Ser Ala Trp Leu Ser
385                 390                 395                 400

Ser Gly Pro Glu Leu Thr Gly Met Pro Arg Val Arg Leu Ala Ala Pro
            405                 410                 415

Leu Ala Val Leu Pro Met Glu Pro Leu Pro Pro Glu Pro Val Arg Pro
            420                 425                 430

Ala Ala Leu Leu Thr Pro Glu Ala Ser Ser Val Gly Gly Pro Asp Gln
            435                 440                 445

Ala Arg Tyr Leu Glu Ser Ala Pro Gly Trp Pro Val Gly Gln Glu Glu
    450                 455                 460

Trp Gly Val Ala His Thr Ser Ser Pro Pro Ser Thr Gln Thr Leu Ser
465                 470                 475                 480

Leu Trp Ala Pro Thr Gly Val Leu Leu Pro Ser Leu Val Glu Leu Glu
            485                 490                 495

Tyr Pro Phe Gln Ala Gly Arg Gly Ala Ser Leu Gln Gln Glu Leu Thr
        500                 505                 510

Glu Pro Thr Leu Ala Leu Ser Ala Glu Ser His Arg Pro Pro Glu Leu
        515                 520                 525

Gln Asp Ser Val Glu Gly Leu Ser Glu Arg Pro Ser Arg
        530                 535                 540
```